US012622718B2

(12) United States Patent
Batchelder et al.

(10) Patent No.: US 12,622,718 B2
(45) Date of Patent: May 12, 2026

(54) INTRAVASCULAR LITHOPLASTY BALLOON SYSTEMS, DEVICES AND METHODS

(71) Applicant: Cardiovascular Systems, Inc., Santa Clara, CA (US)

(72) Inventors: J. Samuel Batchelder, White Bear Township, MN (US); John R. Ballard, White Bear Township, MN (US); Michael P. Brenzel, White Bear Township, MN (US); Alexander P. Thome, White Bear Township, MN (US)

(73) Assignee: Cardiovascular Systems, Inc., Santa Clara, CA (US)

( * ) Notice: Subject to any disclaimer, the term of this patent is extended or adjusted under 35 U.S.C. 154(b) by 67 days.

(21) Appl. No.: 18/681,278

(22) PCT Filed: Aug. 5, 2022

(86) PCT No.: PCT/US2022/074607
§ 371 (c)(1),
(2) Date: Feb. 5, 2024

(87) PCT Pub. No.: WO2023/015295
PCT Pub. Date: Feb. 9, 2023

(65) Prior Publication Data
US 2024/0307081 A1 Sep. 19, 2024

Related U.S. Application Data

(63) Continuation-in-part of application No. 17/449,883, filed on Oct. 4, 2021, and a continuation-in-part of
(Continued)

(51) Int. Cl.
*A61B 17/22* (2006.01)
*A61M 25/10* (2013.01)

(52) U.S. Cl.
CPC .................. *A61B 17/22022* (2013.01); *A61B 2017/22062* (2013.01); *A61M 25/104* (2013.01)

(58) Field of Classification Search
CPC .............. A61B 17/22; A61B 17/22004; A61B 17/22012; A61B 17/2202;
(Continued)

(56) References Cited

U.S. PATENT DOCUMENTS

| 2,916,647 | A | 12/1959 | George |
| 3,412,288 | A | 11/1968 | Ostrander |
| (Continued) | | | |

FOREIGN PATENT DOCUMENTS

| AT | E482647 | T1 | 10/2010 |
| AU | 22933/88 | A | 4/1989 |
| (Continued) | | | |

OTHER PUBLICATIONS

Mohiuddin et al., "General principles of endovascular therapy" in Endovascular Therapy: Principles of Peripheral Interventions, pp. 1-19 (2006).
(Continued)

*Primary Examiner* — Robert A Lynch

(57) ABSTRACT

Various embodiments of the systems, methods and devices are provided for breaking up calcified lesions in an anatomical conduit. More specifically, an electrical arc is generated between two spaced-apart electrodes disposed within a fluid-filled balloon, creating flow and pressure waves. In some embodiments, the electrodes are spaced apart across relatively long distances to create a stronger shock. In some embodiments, the saline ionically conducting between the electrodes is confined to reduce parasitic heating. In some embodiments, the balloon is partially deflated during arc generation.

32 Claims, 28 Drawing Sheets

Related U.S. Application Data application No. 17/454,574, filed on Nov. 11, 2021, now Pat. No. 12,089,861, said application No. PCT/US2022/074607 is a continuation-in-part of application No. 17/454,587, filed on Nov. 11, 2021, now Pat. No. 11,896,248, which is a continuation of application No. 17/449,883, filed on Oct. 4, 2021, said application No. PCT/US2022/074607 is a continuation-in-part of application No. 17/454,667, filed on Nov. 12, 2021, which is a continuation of application No. 17/449,883, filed on Oct. 4, 2021, said application No. PCT/US2022/074607 is a continuation-in-part of application No. 17/454,668, filed on Nov. 12, 2021, now Pat. No. 11,957,369, which is a continuation of application No. 17/449,883, filed on Oct. 4, 2021, said application No. PCT/US2022/074607 is a continuation of application No. 17/454,718, filed on Nov. 12, 2021, now Pat. No. 11,801,066, which is a continuation of application No. 17/449,883, filed on Oct. 4, 2021, said application No. PCT/US2022/074607 is a continuation-in-part of application No. 17/454,721, filed on Nov. 12, 2021, now Pat. No. 11,877,761, which is a continuation of application No. 17/449,883, filed on Oct. 4, 2021, said application No. PCT/US2022/074607 is a continuation-in-part of application No. 17/644,173, filed on Dec. 14, 2021, now abandoned, which is a continuation of application No. 17/449,883, filed on Oct. 4, 2021.

(60) Provisional application No. 63/229,737, filed on Aug. 5, 2021.

(58) Field of Classification Search
CPC ............ A61B 17/22022; A61B 17/225; A61B 17/2256; A61B 2017/22021; A61B 2017/22025; A61B 2017/22051; A61B 2017/22062; A61M 25/1006; A61M 25/1011; A61M 25/104; A61M 2025/1013; A61M 2025/1015
See application file for complete search history.

(56) References Cited

U.S. PATENT DOCUMENTS

| | | |
|---|---|---|
| 3,413,976 A | 12/1968 | Voolfovich |
| 3,524,101 A | 8/1970 | Barbini |
| 3,583,766 A | 6/1971 | Padberg, Jr. |
| 3,785,382 A | 1/1974 | Schmidt et al. |
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,446,867 A | 5/1984 | Leveen et al. |
| 4,587,975 A | 5/1986 | Salo et al. |
| 4,608,983 A | 9/1986 | Mueller et al. |
| 4,643,186 A | 2/1987 | Rosen et al. |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,697,588 A | 10/1987 | Reichenberger |
| 4,702,248 A | 10/1987 | Mestas et al. |
| 4,715,375 A | 12/1987 | Nowacki et al. |
| 4,715,376 A | 12/1987 | Nowacki et al. |
| 4,741,405 A | 5/1988 | Moeny et al. |
| 4,766,608 A | 8/1988 | Cusick et al. |
| 4,781,677 A | 11/1988 | Wilcox |
| 4,793,329 A | 12/1988 | Mahler et al. |
| 4,799,482 A | 1/1989 | Takayama |
| 4,809,682 A | 3/1989 | Forssmann et al. |
| 4,813,934 A | 3/1989 | Engelson et al. |
| 4,878,495 A | 11/1989 | Grayzel |
| 4,890,603 A | 1/1990 | Filler |
| 4,900,303 A | 2/1990 | Lemelson |
| 4,901,709 A | 2/1990 | Rattner |
| 4,905,673 A | 3/1990 | Pimiskern |
| 4,905,675 A | 3/1990 | Oppelt |
| 4,909,252 A | 3/1990 | Goldberger |
| 4,915,094 A | 4/1990 | Lacruche et al. |
| 4,930,496 A | 6/1990 | Bosley, Jr. |
| 4,936,281 A | 6/1990 | Stasz |
| 4,955,143 A | 9/1990 | Hagelauer |
| 4,955,377 A | 9/1990 | Lennox et al. |
| 4,955,385 A | 9/1990 | Kvalo et al. |
| 4,961,738 A | 10/1990 | Mackin |
| 4,962,753 A | 10/1990 | Cathignol et al. |
| 4,966,132 A | 10/1990 | Nowacki et al. |
| 4,968,314 A | 11/1990 | Michaels |
| 4,990,134 A | 2/1991 | Auth |
| 4,994,032 A | 2/1991 | Sugiyama et al. |
| 4,998,932 A | 3/1991 | Rosen et al. |
| 5,002,085 A | 3/1991 | Fitzgerald |
| 5,009,232 A | 4/1991 | Hassler et al. |
| 5,040,548 A | 8/1991 | Yock |
| 5,046,503 A | 9/1991 | Schneiderman |
| 5,057,103 A | 10/1991 | Davis |
| 5,057,106 A | 10/1991 | Kasevich et al. |
| 5,057,107 A | 10/1991 | Parins et al. |
| 5,061,240 A | 10/1991 | Cherian |
| 5,072,723 A | 12/1991 | Viebach |
| 5,078,717 A | 1/1992 | Parins et al. |
| 5,102,402 A | 4/1992 | Dror et al. |
| 5,103,804 A | 4/1992 | Abele et al. |
| 5,116,227 A | 5/1992 | Levy |
| 5,146,912 A | 9/1992 | Eizenhoefer |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Mueller et al. |
| 5,211,683 A | 5/1993 | Maginot |
| 5,231,976 A | 8/1993 | Wiksell |
| 5,233,980 A | 8/1993 | Mestas et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,304,220 A | 4/1994 | Maginot |
| 5,308,354 A | 5/1994 | Zacca et al. |
| 5,320,634 A | 6/1994 | Vigil et al. |
| 5,321,715 A | 6/1994 | Trost |
| 5,324,255 A | 6/1994 | Passafaro et al. |
| 5,336,234 A | 8/1994 | Vigil et al. |
| 5,358,487 A | 10/1994 | Miller |
| 5,362,309 A | 11/1994 | Carter |
| 5,364,393 A | 11/1994 | Auth et al. |
| 5,366,443 A | 11/1994 | Eggers et al. |
| 5,368,591 A | 11/1994 | Lennox et al. |
| 5,395,335 A | 3/1995 | Jang |
| 5,395,361 A | 3/1995 | Fox et al. |
| 5,411,016 A | 5/1995 | Kume et al. |
| 5,417,208 A | 5/1995 | Winkler |
| 5,425,735 A | 6/1995 | Rosen et al. |
| 5,433,731 A | 7/1995 | Hoegnelid et al. |
| 5,454,809 A | 10/1995 | Janssen |
| 5,456,712 A | 10/1995 | Maginot |
| 5,458,652 A | 10/1995 | Uebelacker |
| 5,470,352 A | 11/1995 | Rappaport |
| 5,472,406 A | 12/1995 | Torre et al. |
| 5,474,080 A | 12/1995 | Hughes |
| 5,520,645 A | 5/1996 | Imran et al. |
| 5,571,167 A | 11/1996 | Maginot |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |

(56) References Cited

U.S. PATENT DOCUMENTS

| | | | |
|---|---|---|---|
| 5,611,807 A | 3/1997 | O'Boyle |
| 5,662,590 A | 9/1997 | Torre et al. |
| 5,681,336 A | 10/1997 | Clement et al. |
| 5,709,676 A | 1/1998 | Alt |
| 5,741,246 A | 4/1998 | Prescott |
| 5,749,375 A | 5/1998 | Maginot |
| 5,766,152 A | 6/1998 | Morley et al. |
| 5,836,874 A | 11/1998 | Swanson et al. |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 5,967,984 A | 10/1999 | Chu et al. |
| 5,979,455 A | 11/1999 | Maginot |
| 5,995,871 A | 11/1999 | Knisley |
| 6,007,530 A | 12/1999 | Doernhoefer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster, Jr. |
| 6,113,560 A | 9/2000 | Simnacher |
| 6,123,718 A | 9/2000 | Tu et al. |
| 6,132,444 A | 10/2000 | Shturman et al. |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,287,331 B1 | 9/2001 | Heath |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,375,651 B2 | 4/2002 | Grasso et al. |
| 6,390,995 B1 | 5/2002 | Ogden et al. |
| 6,398,792 B1 | 6/2002 | O'Connor |
| 6,401,721 B1 | 6/2002 | Maginot |
| 6,406,486 B1 | 6/2002 | Torre et al. |
| 6,440,124 B1 | 8/2002 | Esch et al. |
| 6,456,888 B1 | 9/2002 | Skinner et al. |
| 6,464,660 B2 | 10/2002 | Brisken et al. |
| 6,494,890 B1 | 12/2002 | Shturman et al. |
| 6,500,174 B1 | 12/2002 | Maguire et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,599,313 B1 | 7/2003 | Maginot |
| 6,607,003 B1 | 8/2003 | Wilson |
| 6,635,054 B2 | 10/2003 | Fjield et al. |
| 6,638,246 B1 | 10/2003 | Naimark et al. |
| 6,652,547 B2 | 11/2003 | Rabiner et al. |
| 6,666,828 B2 | 12/2003 | Greco et al. |
| 6,666,834 B2 | 12/2003 | Restle et al. |
| 6,669,655 B1 | 12/2003 | Acker et al. |
| 6,689,089 B1 | 2/2004 | Tiedtke et al. |
| 6,726,681 B2 | 4/2004 | Grasso et al. |
| 6,736,784 B1 | 5/2004 | Menne et al. |
| 6,736,811 B2 | 5/2004 | Panescu et al. |
| 6,740,081 B2 | 5/2004 | Hilal |
| 6,755,821 B1 | 6/2004 | Fry |
| 6,758,847 B2 | 7/2004 | Maguire |
| 6,800,080 B1 | 10/2004 | Bates |
| 6,939,320 B2 | 9/2005 | Lennox |
| 6,954,977 B2 | 10/2005 | Maguire et al. |
| 6,989,009 B2 | 1/2006 | Lafontaine |
| 7,033,383 B1 | 4/2006 | Maginot |
| 7,066,904 B2 | 6/2006 | Rosenthal et al. |
| 7,087,061 B2 | 8/2006 | Chernenko et al. |
| 7,104,983 B2 | 9/2006 | Grasso et al. |
| 7,153,315 B2 | 12/2006 | Miller |
| 7,175,605 B2 | 2/2007 | Tiedtke et al. |
| 7,241,295 B2 | 7/2007 | Maguire |
| 7,247,269 B2 | 7/2007 | Keidar |
| 7,309,324 B2 | 12/2007 | Hayes et al. |
| 7,379,767 B2 | 5/2008 | Rea |
| 7,389,148 B1 | 6/2008 | Morgan |
| 7,390,308 B2 | 6/2008 | Schultheiss |
| 7,410,486 B2 | 8/2008 | Fuimaono et al. |
| 7,505,812 B1 | 3/2009 | Eggers et al. |
| 7,540,846 B2 | 6/2009 | Harhen et al. |
| 7,569,032 B2 | 8/2009 | Naimark et al. |
| 7,597,697 B1 | 10/2009 | Maginot |
| 7,628,785 B2 | 12/2009 | Hadjicostis et al. |
| 7,651,492 B2 | 1/2010 | Wham |
| 7,720,521 B2 | 5/2010 | Chang et al. |
| 7,736,362 B2 | 6/2010 | Eberl et al. |
| 7,744,595 B2 | 6/2010 | Truckai et al. |
| 7,744,620 B2 | 6/2010 | Pedersen et al. |
| 7,753,946 B2 | 7/2010 | Maginot |
| 7,754,047 B2 | 7/2010 | Kelley |
| 7,829,029 B2 | 11/2010 | Zumeris et al. |
| 7,837,672 B2 | 11/2010 | Intoccia |
| 7,850,685 B2 | 12/2010 | Kunis et al. |
| 7,853,332 B2 | 12/2010 | Olsen et al. |
| 7,855,904 B2 | 12/2010 | Kirbie et al. |
| 7,873,404 B1 | 1/2011 | Patton |
| 7,914,525 B2 | 3/2011 | Abboud et al. |
| 7,920,921 B2 | 4/2011 | Syed et al. |
| 7,942,850 B2 | 5/2011 | Levit et al. |
| 7,951,111 B2 | 5/2011 | Drasler et al. |
| 7,959,602 B2 | 6/2011 | Tiedtke et al. |
| 8,025,661 B2 | 9/2011 | Arnold et al. |
| 8,133,199 B2 | 3/2012 | Weber et al. |
| 8,162,859 B2 | 4/2012 | Schultheiss et al. |
| 8,177,801 B2 | 5/2012 | Kallok et al. |
| 8,182,530 B2 | 5/2012 | Huber |
| 8,197,463 B2 | 6/2012 | Intoccia |
| 8,241,272 B2 | 8/2012 | Arnold et al. |
| 8,277,444 B2 | 10/2012 | Arnold et al. |
| 8,333,763 B2 | 12/2012 | Truckai et al. |
| 8,343,170 B2 | 1/2013 | Massicotte et al. |
| 8,353,923 B2 | 1/2013 | Shturman |
| 8,366,705 B2 | 2/2013 | Arnold et al. |
| 8,382,771 B2 | 2/2013 | Gellman et al. |
| 8,444,639 B2 | 5/2013 | Arnold et al. |
| 8,518,038 B2 | 8/2013 | Swanson |
| 8,529,581 B2 | 9/2013 | Massicotte et al. |
| 8,556,813 B2 | 10/2013 | Cioanta et al. |
| 8,556,890 B2 | 10/2013 | Wham |
| 8,574,247 B2 | 11/2013 | Adams et al. |
| 8,632,461 B2 | 1/2014 | Glossop |
| 8,685,201 B2 | 4/2014 | O'Rourke et al. |
| 8,709,075 B2 | 4/2014 | Adams et al. |
| 8,728,091 B2 | 5/2014 | Hakala et al. |
| 8,747,416 B2 | 6/2014 | Hakala et al. |
| 8,790,359 B2 | 7/2014 | Rabiner et al. |
| 8,805,466 B2 | 8/2014 | Salahieh et al. |
| 8,888,788 B2 | 11/2014 | Hakala et al. |
| 8,897,869 B2 | 11/2014 | Kassab |
| 8,900,166 B2 | 12/2014 | Spector |
| 8,900,264 B2 | 12/2014 | Drasler et al. |
| 8,926,630 B2 | 1/2015 | Diamant et al. |
| 8,956,371 B2 | 2/2015 | Hawkins et al. |
| 8,956,374 B2 | 2/2015 | Hawkins et al. |
| 9,005,198 B2 | 4/2015 | Long et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Hawkins et al. |
| 9,119,624 B2 | 9/2015 | Wham |
| 9,138,249 B2 | 9/2015 | Adams et al. |
| 9,161,768 B2 | 10/2015 | Cioanta et al. |
| 9,180,280 B2 | 11/2015 | Hawkins et al. |
| 9,198,825 B2 | 12/2015 | Katragadda et al. |
| 9,220,521 B2 | 12/2015 | Hawkins et al. |
| 9,277,955 B2 | 3/2016 | Herscher et al. |
| 9,289,258 B2 | 3/2016 | Cohen |
| 9,333,000 B2 | 5/2016 | Hakala et al. |

(56) References Cited

U.S. PATENT DOCUMENTS

| | | | |
|---|---|---|---|
| 9,375,533 B2 | 6/2016 | Ducharme et al. |
| 9,421,025 B2 | 8/2016 | Hawkins et al. |
| 9,431,428 B2 | 8/2016 | Yamazaki |
| 9,433,428 B2 | 9/2016 | Hakala et al. |
| 9,504,807 B2 | 11/2016 | Drasler et al. |
| 9,522,012 B2 | 12/2016 | Adams |
| 9,579,114 B2 | 2/2017 | Mantell et al. |
| 9,610,006 B2 | 4/2017 | Salahieh et al. |
| 9,636,124 B2 | 5/2017 | Mantell |
| 9,642,673 B2 | 5/2017 | Adams et al. |
| 9,717,513 B2 | 8/2017 | Golan |
| 9,730,715 B2 | 8/2017 | Adams |
| 9,743,980 B2 | 8/2017 | Diamant et al. |
| 9,757,194 B2 | 9/2017 | Werneth et al. |
| 9,763,624 B2 | 9/2017 | Stanislaus et al. |
| 9,808,167 B2 | 11/2017 | Kassab |
| 9,814,476 B2 | 11/2017 | Adams et al. |
| 9,833,373 B2 | 12/2017 | Brouillette et al. |
| 9,861,377 B2 | 1/2018 | Mantell |
| 9,867,629 B2 | 1/2018 | Hawkins |
| 9,913,594 B2 | 3/2018 | Li et al. |
| 9,974,607 B2 | 5/2018 | Stone et al. |
| 9,993,292 B2 | 6/2018 | Adams et al. |
| 10,010,666 B2 | 7/2018 | Rubinsky et al. |
| 10,039,561 B2 | 8/2018 | Adams et al. |
| 10,058,340 B2 | 8/2018 | Cioanta et al. |
| 10,118,015 B2 | 11/2018 | De et al. |
| 10,149,690 B2 | 12/2018 | Hawkins et al. |
| 10,154,799 B2 | 12/2018 | Van et al. |
| 10,159,505 B2 | 12/2018 | Hakala et al. |
| 10,194,930 B2 | 2/2019 | Du |
| 10,206,698 B2 | 2/2019 | Hakala et al. |
| 10,219,720 B2 | 3/2019 | Kassab |
| 10,226,265 B2 | 3/2019 | Ku et al. |
| 10,238,405 B2 | 3/2019 | Cioanta et al. |
| 10,364,981 B2 | 7/2019 | Wang et al. |
| 10,426,500 B2 | 10/2019 | Lipowski et al. |
| 10,478,202 B2 | 11/2019 | Adams et al. |
| 10,500,128 B2 | 12/2019 | Engles et al. |
| 10,517,620 B2 | 12/2019 | Adams |
| 10,517,621 B1 | 12/2019 | Adams |
| 10,555,744 B2 | 2/2020 | Nguyen et al. |
| 10,603,058 B2 | 3/2020 | Mantell |
| 10,639,051 B2 | 5/2020 | Cioanta et al. |
| 10,646,240 B2 | 5/2020 | Betelia et al. |
| 10,661,034 B2 | 5/2020 | Mantell et al. |
| 10,668,208 B2 | 6/2020 | Rubinsky et al. |
| 10,682,178 B2 | 6/2020 | Adams et al. |
| 10,702,293 B2 | 7/2020 | Hawkins et al. |
| 10,709,462 B2 | 7/2020 | Nguyen et al. |
| 10,751,000 B2 | 8/2020 | Hacker |
| 10,765,440 B2 | 9/2020 | Tozzi |
| 10,806,504 B2 | 10/2020 | Hubelbank |
| 10,849,637 B1 | 12/2020 | Mantell |
| 10,849,879 B1 | 12/2020 | Seward |
| 10,850,078 B2 | 12/2020 | Grace et al. |
| 10,888,373 B2 | 1/2021 | Koblish et al. |
| 10,893,903 B2 | 1/2021 | Koblish et al. |
| 10,959,743 B2 | 3/2021 | Adams et al. |
| 10,966,737 B2 | 4/2021 | Nguyen |
| 10,973,538 B2 | 4/2021 | Hakala et al. |
| 11,000,299 B2 | 5/2021 | Hawkins et al. |
| 11,020,135 B1 | 6/2021 | Hawkins |
| 11,076,874 B2 | 8/2021 | Hakala et al. |
| 11,160,467 B2 | 11/2021 | Kassab et al. |
| 11,219,388 B2 | 1/2022 | Kassab |
| 11,266,817 B2 | 3/2022 | Cope et al. |
| 11,337,713 B2 | 5/2022 | Nguyen et al. |
| 11,432,834 B2 | 9/2022 | Adams |
| 11,478,261 B2 | 10/2022 | Nguyen |
| 11,484,327 B2 | 11/2022 | Anderson et al. |
| 11,534,187 B2 | 12/2022 | Bonutti |
| 11,559,318 B2 | 1/2023 | Lipowski et al. |
| 11,559,319 B2 | 1/2023 | Mantell |
| 11,596,424 B2 | 3/2023 | Hakala et al. |
| 11,602,363 B2 | 3/2023 | Nguyen |
| 11,617,618 B2 | 4/2023 | Koblish et al. |
| 11,622,780 B2 | 4/2023 | Nguyen et al. |
| 11,666,348 B2 | 6/2023 | Cioanta et al. |
| 11,672,554 B1 | 6/2023 | Mantell |
| 11,696,799 B2 | 7/2023 | Adams et al. |
| 11,771,449 B2 | 10/2023 | Adams et al. |
| 11,779,363 B2 | 10/2023 | Vo |
| 11,839,391 B2 | 12/2023 | Schultheis et al. |
| 11,857,212 B2 | 1/2024 | Capelli et al. |
| 11,911,056 B2 | 2/2024 | Anderson et al. |
| 11,925,366 B2 | 3/2024 | Cioanta et al. |
| 11,944,331 B2 | 4/2024 | Anderson et al. |
| 11,996,649 B1 | 5/2024 | Carpenter |
| 12,004,759 B2 | 6/2024 | Cioanta |
| 12,004,760 B2 | 6/2024 | Cioanta |
| 12,016,610 B2 | 6/2024 | Flores et al. |
| 12,016,817 B2 | 6/2024 | Engles et al. |
| 12,035,932 B1 | 7/2024 | Nunes et al. |
| 12,048,445 B2 | 7/2024 | Mantell |
| 12,114,923 B2 | 10/2024 | Adams et al. |
| 12,178,458 B1 | 12/2024 | Betelia et al. |
| 12,214,147 B2 | 2/2025 | Gianotti et al. |
| 12,426,904 B2 | 9/2025 | Nguyen et al. |
| 2001/0044596 A1 | 11/2001 | Jaafar |
| 2002/0045890 A1 | 4/2002 | Celliers et al. |
| 2002/0082553 A1 | 6/2002 | Duchamp |
| 2002/0169458 A1 | 11/2002 | Connors |
| 2002/0177889 A1 | 11/2002 | Brisken et al. |
| 2003/0004434 A1 | 1/2003 | Greco et al. |
| 2003/0014047 A1 | 1/2003 | Woloszko et al. |
| 2003/0065371 A1 | 4/2003 | Satake |
| 2003/0135223 A1 | 7/2003 | Teague et al. |
| 2003/0176873 A1 | 9/2003 | Chernenko et al. |
| 2003/0191492 A1 | 10/2003 | Gellman et al. |
| 2003/0229370 A1 | 12/2003 | Miller |
| 2004/0006288 A1 | 1/2004 | Spector et al. |
| 2004/0006307 A1 | 1/2004 | Qureshi et al. |
| 2004/0010249 A1 | 1/2004 | Truckai et al. |
| 2004/0024347 A1 | 2/2004 | Wilson et al. |
| 2004/0044308 A1 | 3/2004 | Naimark et al. |
| 2004/0054367 A1 | 3/2004 | Jimenez et al. |
| 2004/0073251 A1 | 4/2004 | Weber |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0167466 A1 | 8/2004 | Drasler et al. |
| 2004/0172110 A1 | 9/2004 | Satake |
| 2004/0215139 A1 | 10/2004 | Cohen |
| 2004/0249401 A1 | 12/2004 | Rabiner et al. |
| 2004/0254570 A1 | 12/2004 | Hadjicostis et al. |
| 2005/0010140 A1 | 1/2005 | Forssmann |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0096669 A1 | 5/2005 | Rabiner et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0194583 A1 | 9/2005 | Taylor et al. |
| 2005/0197667 A1 | 9/2005 | Chan et al. |
| 2005/0228372 A1 | 10/2005 | Truckai et al. |
| 2005/0228428 A1 | 10/2005 | Ali et al. |
| 2005/0245866 A1 | 11/2005 | Azizi |
| 2005/0251131 A1 | 11/2005 | Lesh |
| 2005/0256410 A1 | 11/2005 | Rabiner et al. |
| 2005/0267467 A1 | 12/2005 | Paul et al. |
| 2005/0267488 A1 | 12/2005 | Hare et al. |
| 2005/0273130 A1 | 12/2005 | Sell |
| 2006/0004286 A1 | 1/2006 | Chang et al. |
| 2006/0041304 A1 | 2/2006 | Jang et al. |
| 2006/0064081 A1 | 3/2006 | Rosinko |
| 2006/0069424 A1 | 3/2006 | Acosta et al. |
| 2006/0074484 A1 | 4/2006 | Huber |
| 2006/0178685 A1 | 8/2006 | Melsheimer |
| 2006/0184076 A1 | 8/2006 | Gill et al. |
| 2006/0190022 A1 | 8/2006 | Beyar et al. |

(56)            References Cited

U.S. PATENT DOCUMENTS

| | | |
|---|---|---|
| 2006/0200191 A1 | 9/2006 | Zadno-Azizi |
| 2006/0221528 A1 | 10/2006 | Li et al. |
| 2006/0235269 A1 | 10/2006 | Waxman |
| 2006/0241524 A1 | 10/2006 | Lee et al. |
| 2006/0282153 A1 | 12/2006 | Jang |
| 2007/0005053 A1 | 1/2007 | Dando |
| 2007/0016112 A1 | 1/2007 | Schultheiss et al. |
| 2007/0032723 A1 | 2/2007 | Glossop |
| 2007/0038227 A1 | 2/2007 | Massicotte et al. |
| 2007/0078500 A1 | 4/2007 | Ryan et al. |
| 2007/0088380 A1 | 4/2007 | Hirszowicz et al. |
| 2007/0106320 A1 | 5/2007 | Blix et al. |
| 2007/0123851 A1 | 5/2007 | Alejandro et al. |
| 2007/0129667 A1 | 6/2007 | Tiedtke et al. |
| 2007/0156129 A1 | 7/2007 | Kovalcheck |
| 2007/0198047 A1 | 8/2007 | Schon et al. |
| 2007/0201031 A1 | 8/2007 | Axelrod et al. |
| 2007/0225677 A1 | 9/2007 | Rowe et al. |
| 2007/0232964 A1 | 10/2007 | Voss |
| 2007/0239082 A1 | 10/2007 | Schultheiss et al. |
| 2007/0239182 A1 | 10/2007 | Glines et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0270897 A1 | 11/2007 | Skerven et al. |
| 2007/0282301 A1 | 12/2007 | Segalescu et al. |
| 2007/0299392 A1 | 12/2007 | Beyar et al. |
| 2007/0299481 A1 | 12/2007 | Syed et al. |
| 2008/0027464 A1 | 1/2008 | Moll et al. |
| 2008/0039790 A1 | 2/2008 | Hasebe |
| 2008/0058836 A1 | 3/2008 | Moll et al. |
| 2008/0065013 A1 | 3/2008 | Goodin |
| 2008/0065014 A1 | 3/2008 | Von et al. |
| 2008/0097251 A1 | 4/2008 | Babaev |
| 2008/0183111 A1 | 7/2008 | Voss |
| 2008/0188803 A1 | 8/2008 | Jang |
| 2008/0188866 A1 | 8/2008 | Karpiel et al. |
| 2008/0188913 A1 | 8/2008 | Stone et al. |
| 2008/0200896 A1 | 8/2008 | Shmulewitz et al. |
| 2008/0249595 A1 | 10/2008 | McDaniel |
| 2008/0300610 A1 | 12/2008 | Chambers |
| 2009/0036829 A1 | 2/2009 | Pagel et al. |
| 2009/0036831 A1 | 2/2009 | Howat |
| 2009/0041833 A1 | 2/2009 | Bettinger et al. |
| 2009/0054875 A1 | 2/2009 | Strauss et al. |
| 2009/0069748 A1 | 3/2009 | Schaeffer |
| 2009/0143651 A1 | 6/2009 | Kallback et al. |
| 2009/0157066 A1 | 6/2009 | Satake |
| 2009/0227992 A1 | 9/2009 | Nir et al. |
| 2009/0234282 A1 | 9/2009 | Mcandrew et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0082059 A1 | 4/2010 | Gellman et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0229792 A1 | 9/2010 | Yamasaki et al. |
| 2010/0274271 A1 | 10/2010 | Kelley |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0092957 A1 | 4/2011 | Intoccia |
| 2011/0196412 A1 | 8/2011 | Levit et al. |
| 2011/0208185 A1 | 8/2011 | Diamant et al. |
| 2011/0257523 A1 | 10/2011 | Hastings et al. |
| 2011/0270273 A1 | 11/2011 | Moll et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall |
| 2012/0157991 A1 | 6/2012 | Christian |
| 2012/0172696 A1 | 7/2012 | Kaellbaeck et al. |
| 2012/0203255 A1 | 8/2012 | Hawkins et al. |
| 2012/0221013 A1 | 8/2012 | Hawkins |
| 2012/0253358 A1 | 10/2012 | Golan |
| 2013/0030431 A1 | 1/2013 | Adams |
| 2013/0030447 A1 | 1/2013 | Adams |
| 2013/0041355 A1 | 2/2013 | Heeren et al. |
| 2013/0096571 A1 | 4/2013 | Massicotte et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0253622 A1 | 9/2013 | Hooven |
| 2014/0005576 A1 | 1/2014 | Adams et al. |
| 2014/0039513 A1 | 2/2014 | Hakala et al. |
| 2014/0039514 A1 | 2/2014 | Adams et al. |
| 2014/0046229 A1 | 2/2014 | Hawkins et al. |
| 2014/0046353 A1 | 2/2014 | Adams |
| 2014/0052145 A1 | 2/2014 | Adams et al. |
| 2014/0052146 A1 | 2/2014 | Curtis et al. |
| 2014/0052147 A1* | 2/2014 | Hakala ............. A61B 17/22022 |
| | | 606/128 |
| 2014/0074111 A1 | 3/2014 | Hakala et al. |
| 2014/0074113 A1 | 3/2014 | Hakala et al. |
| 2014/0163592 A1 | 6/2014 | Hawkins et al. |
| 2014/0214061 A1 | 7/2014 | Adams et al. |
| 2014/0243820 A1 | 8/2014 | Adams et al. |
| 2014/0243846 A1 | 8/2014 | Aggerholm et al. |
| 2014/0243847 A1 | 8/2014 | Hakala et al. |
| 2014/0257323 A1 | 9/2014 | Mantell |
| 2014/0288570 A1 | 9/2014 | Adams |
| 2015/0039002 A1 | 2/2015 | Hawkins |
| 2015/0073430 A1 | 3/2015 | Hakala et al. |
| 2015/0080995 A1 | 3/2015 | Seeley et al. |
| 2015/0238208 A1 | 8/2015 | Adams et al. |
| 2015/0238209 A1 | 8/2015 | Hawkins et al. |
| 2015/0320432 A1 | 11/2015 | Adams |
| 2016/0022295 A1 | 1/2016 | Mantell |
| 2016/0095610 A1 | 4/2016 | Lipowski et al. |
| 2016/0101280 A1 | 4/2016 | Thakkar et al. |
| 2016/0113674 A1 | 4/2016 | Kelley |
| 2016/0135828 A1 | 5/2016 | Hawkins et al. |
| 2016/0151081 A1 | 6/2016 | Adams et al. |
| 2016/0183957 A1 | 6/2016 | Hakala et al. |
| 2016/0324534 A1 | 11/2016 | Hawkins et al. |
| 2016/0331389 A1 | 11/2016 | Hakala et al. |
| 2016/0354144 A1 | 12/2016 | Caplan et al. |
| 2017/0000959 A1 | 1/2017 | Mantell et al. |
| 2017/0056035 A1 | 3/2017 | Adams |
| 2017/0086867 A1 | 3/2017 | Adams |
| 2017/0135709 A1* | 5/2017 | Nguyen ........... A61B 17/22004 |
| 2017/0258523 A1 | 9/2017 | Adams et al. |
| 2017/0274160 A1 | 9/2017 | Mantell et al. |
| 2017/0303946 A1 | 10/2017 | Ku et al. |
| 2017/0311965 A1 | 11/2017 | Adams |
| 2018/0028208 A1 | 2/2018 | Adams et al. |
| 2018/0098779 A1 | 4/2018 | Betelia et al. |
| 2018/0153568 A1 | 6/2018 | Kat-Kuoy |
| 2018/0214166 A1 | 8/2018 | Mantell |
| 2018/0256250 A1 | 9/2018 | Adams et al. |
| 2018/0303501 A1 | 10/2018 | Hawkins |
| 2018/0304053 A1 | 10/2018 | Eggert et al. |
| 2018/0317946 A1 | 11/2018 | Adams et al. |
| 2018/0360482 A1 | 12/2018 | Nguyen et al. |
| 2019/0000491 A1 | 1/2019 | Schoenle |
| 2019/0069916 A1 | 3/2019 | Hawkins et al. |
| 2019/0150960 A1 | 5/2019 | Nguyen et al. |
| 2019/0175198 A1 | 6/2019 | Ku et al. |
| 2019/0254607 A1 | 8/2019 | Kllbck et al. |
| 2019/0254692 A1 | 8/2019 | Hakala et al. |
| 2019/0269426 A1 | 9/2019 | Hakala et al. |
| 2019/0365400 A1 | 12/2019 | Adams et al. |
| 2019/0388110 A1 | 12/2019 | Nguyen et al. |
| 2020/0000484 A1 | 1/2020 | Hawkins |
| 2020/0022716 A1 | 1/2020 | Hakala et al. |
| 2020/0038044 A1 | 2/2020 | Lipowski et al. |
| 2020/0085458 A1 | 3/2020 | Nguyen et al. |

(56) References Cited

U.S. PATENT DOCUMENTS

| | | |
|---|---|---|
| 2020/0085459 A1 | 3/2020 | Adams |
| 2020/0100803 A1 | 4/2020 | Mantell |
| 2020/0129741 A1 | 4/2020 | Kawwas et al. |
| 2020/0129742 A1 | 4/2020 | Cope et al. |
| 2020/0246032 A1 | 8/2020 | Betella et al. |
| 2020/0281505 A1 | 9/2020 | Kassab et al. |
| 2020/0289767 A1 | 9/2020 | Mantell et al. |
| 2020/0297280 A1 | 9/2020 | Kllbck et al. |
| 2020/0297366 A1 | 9/2020 | Nguyen et al. |
| 2020/0383724 A1 | 12/2020 | Adams et al. |
| 2020/0397453 A1 | 12/2020 | Mcgowan et al. |
| 2020/0398033 A1 | 12/2020 | Mcgowan et al. |
| 2020/0406010 A1 | 12/2020 | Massimini et al. |
| 2021/0038237 A1 | 2/2021 | Adams |
| 2021/0059751 A1 | 3/2021 | Zhang et al. |
| 2021/0085347 A1 | 3/2021 | Phan et al. |
| 2021/0085348 A1 | 3/2021 | Nguyen |
| 2021/0085349 A1 | 3/2021 | Cioanta et al. |
| 2021/0085350 A1 | 3/2021 | Cioanta et al. |
| 2021/0085383 A1 | 3/2021 | Vo et al. |
| 2021/0093342 A1 | 4/2021 | Cioanta et al. |
| 2021/0128241 A1 | 5/2021 | Schultheis |
| 2021/0177445 A1 | 6/2021 | Nguyen |
| 2021/0186613 A1 | 6/2021 | Cook et al. |
| 2021/0220052 A1 | 7/2021 | Cook |
| 2021/0228137 A1 | 7/2021 | Aujla |
| 2021/0267615 A1 | 9/2021 | Cioanta et al. |
| 2021/0267685 A1 | 9/2021 | Schultheis et al. |
| 2021/0275247 A1 | 9/2021 | Schultheis et al. |
| 2021/0282792 A1 | 9/2021 | Adams et al. |
| 2021/0290259 A1 | 9/2021 | Hakala et al. |
| 2021/0290305 A1 | 9/2021 | Cook et al. |
| 2021/0308001 A1 | 10/2021 | Cioanta |
| 2021/0310786 A1 | 10/2021 | Zhang et al. |
| 2021/0338258 A1 | 11/2021 | Hawkins et al. |
| 2021/0378743 A1 | 12/2021 | Massimini et al. |
| 2022/0008129 A1 | 1/2022 | Hancock et al. |
| 2022/0015785 A1 | 1/2022 | Hakala et al. |
| 2022/0054194 A1 | 2/2022 | Bacher et al. |
| 2022/0071692 A1 | 3/2022 | Govari et al. |
| 2022/0104875 A1 | 4/2022 | Gleiman et al. |
| 2022/0125453 A1 | 4/2022 | Nguyen |
| 2022/0152321 A1 | 5/2022 | Haber et al. |
| 2022/0183708 A1 | 6/2022 | Phan et al. |
| 2022/0240958 A1 | 8/2022 | Nguyen et al. |
| 2022/0273324 A1 | 9/2022 | Schultheis |
| 2022/0280765 A1 | 9/2022 | Tabiliran et al. |
| 2022/0287732 A1 | 9/2022 | Anderson et al. |
| 2022/0291442 A1 | 9/2022 | De et al. |
| 2022/0313359 A1 | 10/2022 | Schultheis et al. |
| 2022/0331012 A1 | 10/2022 | Bumpus |
| 2022/0338890 A1 | 10/2022 | Anderson et al. |
| 2022/0339428 A1 | 10/2022 | Porterfield et al. |
| 2022/0354578 A1 | 11/2022 | Cook et al. |
| 2023/0028890 A1 | 1/2023 | Cioanta |
| 2023/0043475 A1 | 2/2023 | Adams |
| 2023/0044926 A1 | 2/2023 | Batchelder et al. |
| 2023/0064371 A1 | 3/2023 | Cook et al. |
| 2023/0107690 A1 | 4/2023 | Nguyen |
| 2023/0110647 A1 | 4/2023 | Buscaglia et al. |
| 2023/0111554 A1 | 4/2023 | Lulian |
| 2023/0165598 A1 | 6/2023 | Nguyen et al. |
| 2023/0293195 A1 | 9/2023 | Lipowski et al. |
| 2023/0293196 A1 | 9/2023 | Mantell |
| 2023/0293197 A1 | 9/2023 | Nguyen et al. |
| 2023/0310073 A1 | 10/2023 | Adams et al. |
| 2023/0329731 A1 | 10/2023 | Hakala et al. |
| 2023/0363774 A1 | 11/2023 | Cioanta et al. |
| 2023/0380849 A1 | 11/2023 | Adams et al. |
| 2023/0414234 A1 | 12/2023 | Anderson et al. |
| 2024/0099734 A1 | 3/2024 | Capelli et al. |
| 2024/0188973 A1 | 6/2024 | Cioanta et al. |
| 2024/0188975 A1 | 6/2024 | Nguyen |
| 2024/0189030 A1 | 6/2024 | Cook et al. |
| 2024/0189543 A1 | 6/2024 | Salinas et al. |
| 2024/0206896 A1 | 6/2024 | Ingersoll et al. |
| 2024/0206972 A1 | 6/2024 | Sun et al. |
| 2024/0216062 A1 | 7/2024 | Cook et al. |
| 2024/0252191 A1 | 8/2024 | Cioanta et al. |
| 2024/0252192 A1 | 8/2024 | Anderson et al. |
| 2024/0277374 A1 | 8/2024 | Varilla et al. |
| 2024/0277410 A1 | 8/2024 | Cook |
| 2024/0285295 A1 | 8/2024 | Cioanta |
| 2024/0293282 A1 | 9/2024 | Engles et al. |
| 2024/0335206 A1 | 10/2024 | Liu et al. |
| 2024/0423654 A1 | 12/2024 | Ji et al. |
| 2025/0064471 A1 | 2/2025 | Hasenberg et al. |
| 2025/0160862 A1 | 5/2025 | Betelia et al. |
| 2025/0176984 A1 | 6/2025 | Hasenberg et al. |
| 2025/0303109 A1 | 10/2025 | Johnson et al. |

FOREIGN PATENT DOCUMENTS

| | | |
|---|---|---|
| AU | 2007254353 A1 | 11/2007 |
| AU | 2009257368 A1 | 12/2009 |
| AU | 2009313507 B2 | 11/2014 |
| AU | 2013284490 U | 5/2018 |
| CA | 2104414 A1 | 2/1995 |
| CA | 2613360 A1 | 1/2007 |
| CA | 2652381 A1 | 11/2007 |
| CA | 2727429 A1 | 12/2009 |
| CA | 2779600 A1 | 5/2010 |
| CN | 1204242 A | 1/1999 |
| CN | 1269708 A | 10/2000 |
| CN | 1161081 C | 8/2004 |
| CN | 1942145 A | 4/2007 |
| CN | 101043914 A | 9/2007 |
| CN | 101495023 A | 7/2009 |
| CN | 201629723 U | 11/2010 |
| CN | 102057422 A | 5/2011 |
| CN | 102271748 A | 12/2011 |
| CN | 102355856 A | 2/2012 |
| CN | 102765785 A | 11/2012 |
| CN | 203564304 A | 4/2014 |
| CN | 208694015 U | 4/2019 |
| CN | 109965922 A | 7/2019 |
| CN | 209548049 U | 10/2019 |
| CN | 110811761 A | 2/2020 |
| CN | 111067591 A | 4/2020 |
| CN | 111184553 A | 5/2020 |
| CN | 211094481 U | 7/2020 |
| CN | 211094508 U | 7/2020 |
| CN | 111388086 B | 8/2020 |
| CN | 111568500 A | 8/2020 |
| CN | 111568539 A | 8/2020 |
| CN | 111969882 A | 11/2020 |
| CN | 212491104 U | 2/2021 |
| CN | 112516439 A | 3/2021 |
| CN | 112618922 A | 4/2021 |
| CN | 112674838 A | 4/2021 |
| CN | 112754645 A | 5/2021 |
| CN | 112842460 A | 5/2021 |
| CN | 112869825 A | 6/2021 |
| CN | 112869826 A | 6/2021 |
| CN | 112869827 A | 6/2021 |
| CN | 112932609 A | 6/2021 |
| CN | 113117220 A | 7/2021 |
| CN | 113244506 A | 8/2021 |
| CN | 113288335 A | 8/2021 |
| CN | 113289212 A | 8/2021 |
| CN | 113289216 A | 8/2021 |
| CN | 306761244 S | 8/2021 |
| CN | 113332568 A | 9/2021 |
| CN | 113332569 A | 9/2021 |
| CN | 113332570 A | 9/2021 |
| CN | 113349882 A | 9/2021 |
| CN | 113349982 A | 9/2021 |
| CN | 113398444 A | 9/2021 |
| CN | 113558715 A | 10/2021 |
| CN | 113598878 A | 11/2021 |
| CN | 113730768 A | 12/2021 |
| CN | 113842190 A | 12/2021 |
| CN | 113855153 A | 12/2021 |
| CN | 215228131 U | 12/2021 |

(56) References Cited

FOREIGN PATENT DOCUMENTS

| | | | |
|---|---|---|---|
| CN | 215384399 | U | 1/2022 |
| CN | 215384400 | U | 1/2022 |
| CN | 215386905 | U | 1/2022 |
| CN | 215458400 | U | 1/2022 |
| CN | 215458401 | U | 1/2022 |
| CN | 215505065 | U | 1/2022 |
| CN | 215537694 | U | 1/2022 |
| CN | 215584286 | U | 1/2022 |
| CN | 215606068 | U | 1/2022 |
| CN | 215651394 | U | 1/2022 |
| CN | 215653328 | U | 1/2022 |
| CN | 215688241 | U | 2/2022 |
| CN | 215739273 | U | 2/2022 |
| CN | 215900676 | U | 2/2022 |
| CN | 114098896 | A | 3/2022 |
| CN | 114098897 | A | 3/2022 |
| CN | 114098898 | A | 3/2022 |
| CN | 114209960 | A | 3/2022 |
| CN | 215960130 | U | 3/2022 |
| CN | 216495498 | U | 5/2022 |
| CN | 307361122 | S | 5/2022 |
| CN | 217040236 | U | 7/2022 |
| CN | 217066519 | U | 7/2022 |
| CN | 307436397 | S | 7/2022 |
| CN | 112971914 | B | 8/2022 |
| CN | 114831697 | A | 8/2022 |
| CN | 217138101 | U | 8/2022 |
| CN | 217162846 | U | 8/2022 |
| CN | 115051691 | A | 9/2022 |
| CN | 115149929 | A | 10/2022 |
| CN | 115153753 | A | 10/2022 |
| CN | 115154852 | A | 10/2022 |
| CN | 115192872 | A | 10/2022 |
| CN | 217611283 | U | 10/2022 |
| CN | 115252050 | A | 11/2022 |
| CN | 115389852 | A | 11/2022 |
| CN | 115463317 | A | 12/2022 |
| CN | 218391846 | U | 1/2023 |
| CN | 115737062 | A | 3/2023 |
| CN | 218899599 | U | 4/2023 |
| CN | 115944355 | B | 6/2023 |
| DE | 2635635 | A1 | 2/1978 |
| DE | 3038445 | A1 | 5/1982 |
| DE | 3536073 | A1 | 4/1987 |
| DE | 3900433 | A1 | 7/1990 |
| DE | 3930600 | A1 | 4/1991 |
| DE | 4005743 | A1 | 8/1991 |
| DE | 4007295 | A1 | 9/1991 |
| DE | 4012642 | A1 | 10/1991 |
| DE | 4120259 | A1 | 12/1992 |
| DE | 29724174 | U1 | 4/2000 |
| DE | 10010467 | A1 | 9/2001 |
| DE | 102004053549 | A1 | 5/2006 |
| DE | 202006014285 | A1 | 12/2006 |
| DE | 102006002412 | A1 | 7/2007 |
| EP | 0249338 | A2 | 12/1987 |
| EP | 0311295 | A2 | 4/1989 |
| EP | 0313836 | A2 | 5/1989 |
| EP | 0351240 | A2 | 1/1990 |
| EP | 0382392 | A1 | 8/1990 |
| EP | 0442199 | A1 | 8/1991 |
| EP | 0547146 | A1 | 6/1993 |
| EP | 0558297 | A2 | 9/1993 |
| EP | 0571306 | A1 | 11/1993 |
| EP | 623360 | A1 | 11/1994 |
| EP | 0647435 | A1 | 4/1995 |
| EP | 0704226 | A1 | 4/1996 |
| EP | 1898775 | A2 | 3/2008 |
| EP | 2023796 | A2 | 2/2009 |
| EP | 2043501 | A2 | 4/2009 |
| EP | 2046227 | A2 | 4/2009 |
| EP | 2120736 | A1 | 11/2009 |
| EP | 2253884 | A1 | 11/2010 |
| EP | 2300091 | A2 | 3/2011 |
| EP | 2032201 | B1 | 4/2013 |
| EP | 2362798 | A1 | 4/2014 |
| EP | 2866689 | A1 | 5/2015 |
| EP | 2879607 | A1 | 6/2015 |
| EP | 3487414 | A2 | 5/2019 |
| EP | 3641672 | A1 | 4/2020 |
| EP | 4110213 | A1 | 1/2023 |
| EP | 4199849 | A1 | 6/2023 |
| EP | 4387540 | A1 | 6/2024 |
| EP | 4391946 | A1 | 7/2024 |
| EP | 4406496 | A1 | 7/2024 |
| EP | 4423863 | A1 | 9/2024 |
| EP | 4431032 | A1 | 9/2024 |
| FR | 2412301 | A1 | 7/1979 |
| FR | 2593382 | A1 | 7/1987 |
| FR | 2738381 | A1 | 3/1997 |
| JP | 58-032755 | A | 2/1983 |
| JP | 60-191353 | U | 12/1985 |
| JP | 61-146251 | A | 7/1986 |
| JP | 62-009921 | U | 1/1987 |
| JP | 62-060547 | A | 3/1987 |
| JP | S62-099210 | U | 6/1987 |
| JP | 62-275446 | | 11/1987 |
| JP | S62-275446 | A | 11/1987 |
| JP | H03-63059 | A | 3/1991 |
| JP | 06-070984 | A | 3/1994 |
| JP | H06-125915 | A | 5/1994 |
| JP | H07-47135 | A | 2/1995 |
| JP | H08-89511 | A | 4/1996 |
| JP | H10-99444 | A | 4/1998 |
| JP | H10-314177 | A | 12/1998 |
| JP | H10-513379 | A | 12/1998 |
| JP | 2002538932 | A | 11/2002 |
| JP | 2003-102850 | A | 4/2003 |
| JP | 2004081374 | A | 3/2004 |
| JP | 2004-223080 | A | 8/2004 |
| JP | 2004357792 | A | 12/2004 |
| JP | 2005501597 | A | 1/2005 |
| JP | 2005095410 | A | 4/2005 |
| JP | 2005515825 | A | 6/2005 |
| JP | 2006516465 | A | 7/2006 |
| JP | 2007-054480 | A | 3/2007 |
| JP | 2007289707 | A | 11/2007 |
| JP | 2007532182 | A | 11/2007 |
| JP | 2008506447 | A | 3/2008 |
| JP | 4072580 | B2 | 4/2008 |
| JP | 2009-537222 | A | 10/2009 |
| JP | 4491149 | B2 | 6/2010 |
| JP | 2011513694 | A | 4/2011 |
| JP | 2011520248 | A | 7/2011 |
| JP | 2011524203 | A | 9/2011 |
| JP | 2011528963 | A | 12/2011 |
| JP | 2012505050 | A | 3/2012 |
| JP | 2012508042 | A | 4/2012 |
| JP | 2014-208305 | A | 11/2014 |
| JP | 5636363 | B2 | 12/2014 |
| JP | 2015525657 | A | 9/2015 |
| JP | 2015528327 | A | 9/2015 |
| JP | 6029828 | B2 | 11/2016 |
| JP | 6081510 | B2 | 2/2017 |
| WO | 1989011307 | A1 | 11/1989 |
| WO | 91/10228 | A1 | 7/1991 |
| WO | 91/10403 | A1 | 7/1991 |
| WO | 92/03975 | A1 | 3/1992 |
| WO | 95/10232 | A1 | 4/1995 |
| WO | 1996024297 | A1 | 8/1996 |
| WO | 97/21460 | A1 | 6/1997 |
| WO | 98/33171 | A2 | 7/1998 |
| WO | 1999000060 | A1 | 1/1999 |
| WO | 1999002096 | A1 | 1/1999 |
| WO | 99/21611 | A1 | 5/1999 |
| WO | 00/33913 | A2 | 6/2000 |
| WO | 00/50115 | A2 | 8/2000 |
| WO | 00/51511 | A1 | 9/2000 |
| WO | 2000056237 | A2 | 9/2000 |
| WO | 01/24712 | A1 | 4/2001 |
| WO | 03/51450 | A1 | 6/2003 |
| WO | 03/86236 | A2 | 10/2003 |
| WO | 03/86525 | A1 | 10/2003 |
| WO | 2004069072 | A2 | 8/2004 |

(56) References Cited

FOREIGN PATENT DOCUMENTS

| WO | 2005/053532 A1 | 6/2005 | | |
| WO | 2005099594 A1 | 10/2005 | | |
| WO | 2005102199 A1 | 11/2005 | | |
| WO | 2006006169 A2 | 1/2006 | | |
| WO | 2006/060492 A2 | 6/2006 | | |
| WO | 2006127158 A2 | 11/2006 | | |
| WO | 2007/002079 A2 | 1/2007 | | |
| WO | 2007/022055 A1 | 2/2007 | | |
| WO | 2007/052341 A1 | 5/2007 | | |
| WO | 2007/053967 A1 | 5/2007 | | |
| WO | 2007/086965 A2 | 8/2007 | | |
| WO | 2007088546 A2 | 8/2007 | | |
| WO | 2007/136599 A2 | 11/2007 | | |
| WO | 2007149905 A2 | 12/2007 | | |
| WO | 2008/014425 A2 | 1/2008 | | |
| WO | 2008/017080 A2 | 2/2008 | | |
| WO | 2008/097833 A1 | 8/2008 | | |
| WO | 2009/128061 A2 | 10/2009 | | |
| WO | 2009121017 A1 | 10/2009 | | |
| WO | 2009126544 A1 | 10/2009 | | |
| WO | 2009136268 A2 | 11/2009 | | |
| WO | 2009152352 A2 | 12/2009 | | |
| WO | 2010014515 A2 | 2/2010 | | |
| WO | 2010054048 A2 | 5/2010 | | |
| WO | 2011006017 A1 | 1/2011 | | |
| WO | 2011094111 A2 | 8/2011 | | |
| WO | 2011143468 A2 | 11/2011 | | |
| WO | 2012025833 A2 | 3/2012 | | |
| WO | 2012/064404 A1 | 5/2012 | | |
| WO | 2012/106259 A2 | 8/2012 | | |
| WO | 2013059735 A2 | 4/2013 | | |
| WO | 2013/070750 A1 | 5/2013 | | |
| WO | 2013/169807 A1 | 11/2013 | | |
| WO | 2014/004887 A1 | 1/2014 | | |
| WO | 2014/025981 A1 | 2/2014 | | |
| WO | 2014/028885 A1 | 2/2014 | | |
| WO | 2014025397 A1 | 2/2014 | | |
| WO | 2014025620 A1 | 2/2014 | | |
| WO | 2014/043400 A1 | 3/2014 | | |
| WO | 2015017499 A1 | 2/2015 | | |
| WO | 2015/167360 A1 | 11/2015 | | |
| WO | 2016/130713 A1 | 8/2016 | | |
| WO | 2018200865 A1 | 11/2018 | | |
| WO | 2019099218 A1 | 5/2019 | | |
| WO | 2019174625 A1 | 9/2019 | | |
| WO | 2020/048274 A1 | 3/2020 | | |
| WO | 2020/192146 A1 | 10/2020 | | |
| WO | WO-2021022849 A1 * | 2/2021 | ....... | A61B 17/22022 |
| WO | WO-2021025624 A1 * | 2/2021 | ........ | A61M 25/1011 |
| WO | 2022/127506 A1 | 6/2022 | | |
| WO | 2022/127507 A1 | 6/2022 | | |
| WO | 2022/127509 A1 | 6/2022 | | |
| WO | 2022/166883 A1 | 8/2022 | | |
| WO | 2022/186783 A1 | 9/2022 | | |
| WO | 2022/217917 A1 | 10/2022 | | |
| WO | 2023/015047 A1 | 2/2023 | | |
| WO | 2023/015295 A1 | 2/2023 | | |
| WO | 2023/029191 A1 | 3/2023 | | |
| WO | 2023/083084 A1 | 5/2023 | | |
| WO | 2024/081361 A1 | 4/2024 | | |
| WO | 2024/102896 A2 | 5/2024 | | |
| WO | 2024/107418 A1 | 5/2024 | | |
| WO | 2024/107470 A1 | 5/2024 | | |
| WO | 2024/138037 A2 | 6/2024 | | |
| WO | 2024/138212 A1 | 6/2024 | | |
| WO | 2024/206827 A2 | 10/2024 | | |
| WO | 2024/216050 A2 | 10/2024 | | |

OTHER PUBLICATIONS

Müller-Leisse. et al., "Effectiveness and safety of ultrasonic atherosclerotic plaque ablation: In vitro investigation," Cardiovascular and interventional radiology, vol. 16, 1993, pp. 303-307.

Neuzil, P., et al., "TCT-61 Optimized external focused ultrasound for renal sympathetic denervation—Wave II trial.", Journal of the American College of Cardiology, vol. 62, No. 18S1, 2013.

Nimgaonkar, A., et al., "Gastroenterology and biodesign: contributing to the future of our specialty.", Gastroenterology, vol. 144, No. 2, 2013, pp. 258-262.

Northgate Technologies, Northgate Autolith pulse generator in 2007, at the Wayback Machine, https://web.archive.org/web/20070704002225/http://www.northgate-tech.com:80/Products/stonemanagement.asp.

Notification Concerning Transmittal of International Preliminary Report on Patentability (Chapter I of the Patent Cooperation Treaty) mailed Feb. 15, 2024 for PCT Application Serial No. PCT/US2022/071341, Filed Mar. 25, 2022.

Notification Concerning Transmittal of International Preliminary Report on Patentability (Chapter I of the Patent Cooperation Treaty) mailed Feb. 15, 2024 for PCT Application Serial No. PCT/US2022/074607, Filed Aug. 5, 2022.

Ormiston, J. A., et al., "TCT-412 non-invasive renal denervation using externally delivered focused ultrasound: early experience using Doppler based imaging tracking and targeting for treatment.", Journal of the American College of Cardiology, vol. 64, No. 11, 2014.

Park. et al., "Percutaneous Nephrolithotomy Technical Aspects," The Practical Guide to Medical and Surgical Management, 2007, pp. 621-638.

Payne., "Charles Theodore Dotter: the father of intervention," Texas Heart Institute Journal, vol. 28, Issue 1, 2001, pp. 28-38.

Rassweiler et al. "Efficacy of in situ Extracorporeal Shock Wave Lithotripsy for Upper Ureteral Calculi" Uropean Urology, vol. 12 No. 6, 1986, pp. 377-386.

Rosenschein. et al., "Experimental Ultrasonic Angioplasty: Disruption of Atherosclerotic Plaques and Thrombi in Vitro and Arterial Recanalization in Vivo," Journal of the American College of Cardiology, vol. 15, Issue 3, 1990, pp. 711-717.

Sasportas, L. S., et al., "Cost-effectiveness landscape analysis of treatments addressing xerostomia in patients receiving head and neck radiation therapy.", Oral surgery, oral medicine, oral pathology and oral radiology, vol. 116, No. 1, 2013, pp. e37-e51.

Siegel et al., "Ultrasonic plaque ablation. A new method for recanalization of partially or totally occluded arteries", Circulation, vol. 78, No. 6, Dec. 1988, pp. 1443-1448.

Sista, A. K., et al., "Applying a structured innovation process to interventional radiology: a single-center experience.", Journal of Vascular and Interventional Radiology, vol. 23, No. 4, 2012, 488-494.

Stoller et al., "Urinary Stone Disease: The Practical Guide to Medical and Surgical Management", 2007, 685 Pages.

Svendsen et al., "Conductance sizing balloon for measurement of peripheral artery minimal stent area," Journal of Vascular Surgery, vol. 60, No. 3, Sep. 2014, pp. 759-766.

Welch et al. "Laser Physics and Laser-Tissue Interaction", The Texas Heart Institute Journal, vol. 16 No. 3, 1989, pp. 141-149.

Willmann, J. K., et al., "Imaging gene expression in human mesenchymal stem cells: from small to large animals.", Radiology, vol. 252, No. 1, 2009, pp. 117-127.

Worley. et al., "Electrohydraulic Shock Wave Decalcification of Stenotic Aortic Valves : Postmortem and Intraoperative Studies" Journal of the American College of Cardiology, vol. 12, Issue 2, 1988, pp. 458-462.

Yock, P. G., et al., "Teaching biomedical technology innovation as a discipline.", Science translational medicine, vol. 3, No. 92, 2011, 5 pages.

Zhong et al., "Transient Oscillation of Cavitation Bubbles Near Stone Surface During Electrohydraulic Lithotripsy," Journal of Endourology, vol. 11, No. 1, pp. 55-61 (Feb. 1997).

International Search Report issued in PCT/US2022/74607, mailed Oct. 25, 2022.

International Search Report and Written Opinion, mailed May 28, 2024 for PCT Application Serial No. PCT/US2023/085868, filed Dec. 23, 2023.

International Search Report and Written Opinion, mailed Apr. 12, 2024 for PCT Application Serial No. PCT/US2023/079209, filed Nov. 9, 2023.

(56)          References Cited

OTHER PUBLICATIONS

International Preliminary Report on Patentability for PCT Application Serial No. PCT/US2022/071341, Filed Mar. 25, 2022.
Notification Concerning Transmittal of International Preliminary Report on Patentability (Chapter I of the Patent Cooperation Treaty) for PCT Application Serial No. PCT/US2022/071341, Filed Mar. 25, 2022.
International Preliminary Report on Patentability for PCT Application Serial No. PCT/US2022/074607, Filed Aug. 5, 2022.
Notification Concerning Transmittal of International Preliminary Report on Patentability (Chapter I of the Patent Cooperation Treaty) for PCT Application Serial No. PCT/US2022/074607, Filed Aug. 5, 2022.
International Search Report and Written Opinion, mailed Feb. 22, 2024, for PCT Application Serial No. PCT/US23/73648, filed Sep. 7, 2023.
International Search Report and Written Opinion Issued in PCT/US2021/71726, dated Feb. 7, 2022.
Petition for Inter Partes Review of U.S. Pat. No. 9,642,673 Under 35 U.S.C. Section 312 and 37 C.F.R. Section 42.104, filed Dec. 7, 2018.
Petition for Inter Partes Review of U.S. Pat. No. 8,728,091, filed Dec. 7, 2018.
Petition for Inter Partes Review of U.S. Pat. No. 8,956,371 Under 35 U.S.C. Section 312 and 37 C.F.R. Section 42.104, filed Dec. 7, 2018.
Judgment, Final Written Decision Determining All Challenged Claims Unpatentable Denying Petitioner's Motion to Exclude Denying Petitioner's Motion to Exclude Denying Patent Owner's Motion to Exclude 35 U.S.C. Section 318(a), 37 C.F.R. Section 42.64, Paper 70, IPR2019-00408, in U.S. Pat. No. 9,642,673 B2, Entered Jul. 20, 2020.
Judgment, Final Written Decision Determining Some Challenged Claims Unpatentable Denying Petitioner's Motion to Exclude 35 U.S.C. Section 318(a), 37 C.F.R. Section 42.64, Paper 75, IPR2019-00405, in U.S. Pat. No. 8,956,371 B2, dated Jul. 8, 2020.
Judgment, Final Written Decision Determining All Challenged Claims Unpatentable Denying Petitioner's Motion to Exclude Denying Patent Owner's Motion to Exclude, 35 U.S.C. Section 318(a); 37 C.F.R. Section 42.64, Paper 75, IPR2019-00409, in U.S. Pat. No. 8,728,091 B2, dated Jul. 8, 2020.
Touya, G., et al., "Development of subsonic electrical discharges in water and measurements of the associated pressure waves", Journal of Physics D: Applied Physics, 39 (2006), pp. 5236-5244.
Extended European Search Report dated Jul. 25, 2022 in European Patent Application No. 22168984.7.
International Search Report and Written Opinion issued in PCT application No. PCT/US2022/71341, dated Aug. 11, 2022.
International Search Report and Written Opinion received for International Patent Application No. PCT/US2022/078216, mailed on Feb. 1, 2023, 6 pages.
Cleveland, R.O.; McAteer, J.A. Physics of Shock-Wave Lithotripsy. In Smith's Textbook of Endourology; Wiley: Hoboken, NJ, USA, 2012; pp. 527-558.
Partial Filing History for U.S. Appl. No. 63/193,469, filed May 26, 2021.
Partial File History for U.S. Appl. No. 63/176,156, filed Apr. 16, 2021.
Partial File History for U.S. Appl. No. 63/169,091, filed Mar. 31, 2021.
Partial File History for U.S. Appl. No. 63/154,603, filed Feb. 26, 2021.
Baim., "Grossman's Cardiac Catheterization, Angiography, and Intervention," Seventh Edition, 2005, 6 pages.
Baim., "Percutaneous Balloon Angioplasty and General Coronary Intervention," Chapter 22, 2005, pp. 433-466.
Bertrand et al., "Percutaneous Transluminal Coronary Rotary Ablation with Rotablator (European Experience)", The American Journal of Cardiology, vol. 69, Feb. 15, 1992, pp. 470-474.

Brinton, T. D., et al., "Abstract 12272: Ultrasound Mediated Renal Sympathetic Denervation", Circulation, vol. 124, No. 21, Nov. 22, 2011.
Brinton, T. J., et al., "Current use of imaging in cardiac stem cell clinical trials.", Current Cardiovascular Imaging Reports, vol. 2, No. 1, 2009, pp. 1-2.
Brinton, T. J., et al., "Outcomes from a postgraduate biomedical technology innovation training program: the first 12 years of Stanford Biodesign.", Annals of biomedical engineering, vol. 41, 2013, pp. 1803-1810.
Chan et al., "A Perspective on Laser Lithotripsy: The Fragmentation Processes", Journal of Endourology, vol. 15, No. 3, Apr. 2001, pp. 257-273.
Choi. et al., "Low Power Ultrasound Delivered Through a PTCA-Like Guidewire: Preclinical Feasibility and Safety of a Novel Technology for Intracoronary Thrombolysis," Journal of Interventional Cardiology, vol. 19, Issue 1, 2006, pp. 87-92.
Compare Materials, from MatWeb, retrieved from https://www.matweb.com, accessed on Feb. 26, 2024, 5 pp.
Dash R., et al., "Abstract 12435: Detection of Injured Border Zone Myocardium Using Manganese-Enhanced and Delayed-Enhanced MRI in a Pig Ischemia-Reperfusion Model", Circulation, vol. 122, Supp. 21, Nov. 23, 2010.
Dash, R., et al., "Dual manganese-enhanced and delayed gadolinium-enhanced MRI detects myocardial border zone injury in a pig ischemia-reperfusion model.", Circulation: Cardiovascular Imaging, vol. 4, No. 5, 2011, pp. 574-582.
Dervan et al., "Transluminal angioplasty of occluded coronary arteries: use of a movable guide wire system", Circulation 68, No. 4, 1983, pp. 776-784.
Ernst. et al., "Ability of High-Intensity Ultrasound to Ablate Human Atherosclerotic Plaques and Minimize Debris Size," The American journal of cardiology, vol. 68, Issue 2, 1991, pp. 242-246.
Extended European Search Report dated Jul. 22, 2022 in European Patent Application No. 22168972.2.
Extended European Search Report dated Jul. 25, 2022 in European Patent Application No. 22167795.8.
Extended European Search Report dated Jul. 25, 2022 in European Patent Application No. 22167806.3.
Extended European Search Report dated Jul. 15, 2022 in European Patent Application No. 22167569.7.
Extended European Search Report dated Jul. 19, 2022 in European Patent Application No. 22168990.4.
Extended European Search Report dated Jul. 22, 2022 in European Patent Application No. 22169681.8.
Extended European Search Report dated Jul. 25, 2022 in European Patent Application No. 22167815.4.
Fuh, E., et al., "Bone marrow stem cells for the treatment of ischemic heart disease: a clinical trial review.", Journal of Cardiovascular Translational Research, vol. 2, 2009, pp. 202-218.
Gavin. et al., "An acoustic fluid-structure simulation of a therapeutic ultrasound wire waveguide apparatus," 11th International Conference on Computational Biogengineering, 2005, 14 pages.
Gerdesmeyer. et al., "Physical and technical basics of extracorporeal shock wave therapy (ESWT)," The orthopedist, vol. 7, Issue 31, 2002, pp. 610-617. (English abstract).
Gravenstein D., "Extracorporeal shock wave lithotripsy and percutaneous nephrolithotomy", Anesthesia and Renal Considerations, vol. 18, No. 4, Dec. 2000, pp. 953-971.
Grech., "Percutaneous coronary intervention. I: History and development," Bmj, vol. 326, Issue 7398, 2003, pp. 1080-1082.
Gunn. et al., "New developments in percutaneous coronary intervention," BMJ, vol. 327, Issue 7407, 2003, pp. 150-153.
Harston et al., "Safety and Success of the Beginning Percutaneous Transluminal Coronary Angioplasty Program Using the Steerable Guidewire System", Coronary Angioplasty With Steerable Guidewire, vol. 57, Apr. 1, 1986, pp. 717-720.
Hong, S. J., et al., "Intracoronary and retrograde coronary venous myocardial delivery of adipose-derived stem cells in swine infarction lead to transient myocardial trapping with predominant pulmonary redistribution.", Catheterization and Cardiovascular Interventions, vol. 83, No. 1, 2014, pp. E17-E25.

(56)                References Cited

OTHER PUBLICATIONS

International Application No. PCT/US2024/022239, filed Mar. 29, 2014.
International Application No. PCT/US2024/024296, filed Apr. 12, 2024.
International Application No. PCT/US2024/025362, filed Apr. 19, 2024.
International Application No. PCT/US2024/025369, filed Apr. 19, 2024.
International Search Report and Written Opinion of International Application No. PCT/US2023/85515, mailed Jun. 13, 2024, 10 pp.
International Search Report and Written Opinion of International Application No. PCT/US2024/022239, mailed Jul. 26, 2024, 8 pp.
International Search Report and Written Opinion of International Application No. PCT/US2024/024296, mailed Aug. 21, 2024, 14 pp.
International Search Report and Written Opinion of International Application No. PCT/US2024/025362, mailed Jul. 23, 2024, 12 pp.
International Search Report and Written Opinion of International Application No. PCT/US2024/025369, mailed Jul. 23, 2024, 11 pp.
International Search Report and Written Opinion of International Application No. PCT/US2023/035025, mailed Jan. 18, 2024, 11 pp.
International Search Report and Written Opinion of International Application No. PCT/US2023/037234, mailed Mar. 12, 2024, 8 pp.
Kaltenbach, "The long wire technique—a new technique for steerable balloon catheter dilatation of coronary artery stenoses", European Heart Journal, vol. 5, 1984, pp. 1004-1009.
Kodama et al. "Innovative technology for tissue disruption by explosive-induced shock waves", Ultrasound in Medicine & Biology vol. 24, No. 9, 1998, pp. 1459-1460.
Lee. et al., "Intravascular steerable guidewire for fiberoptic laser-heated metal cautery cap in dissolution of human atherosclerotic coronary disease," American Heart Journal, vol. 110, Issue 6, 1985, pp. 1304-1306.
Levin. et al., "Percutaneous Transluminal Coronary Angioplasty with an Over-the-Wire System," Radiology, vol. 155, Issue 2, 1985, pp. 323-326.
Litvack. et al., "Percutaneous excimer laser coronary angioplasty: results in the first consecutive 3,000 patients," Journal of the American College of Cardiology, vol. 23, Issue 2, 1994, pp. 323-329.
Lumsden. et al., "Endovascular Therapy Principles of Peripheral Interventions," Blackwell Futura, 2006, 310 pages.
Mariani., "Combined Electrohydraulic and Holmium:Yag Laser Ureteroscopic Nephrolithotripsy for 20 to 40 MM Renal Calculi," The Journal of urology, vol. 172, Issue 1, 2004, pp. 170-174.

McAuley. et al., "Advances in guidewire technology," The American Journal of Cardiology, vol. 53, Issue 12, 1984, pp. C94-C96.
Miller et al., "Electrohydraulic Nephrolithotripsy: a Preferable Alternative to Ultrasound?", British Journal of Urology, vol. 56, 1984, pp. 589-593.
Miller., "Endoscopic application of shock wave technology for the destruction of renal calculi" World Journal of Urology, vol. 3, 1985, pp. 36-40.
Mishra, A., et al., "RevaTen platelet-rich plasma improves cardiac function after myocardial injury.", Cardiovascular Revascularization Medicine, vol. 12, No. 3, 2011, pp. 158-163.
Ali, Z. "The Sound Science Behind Shockwave IVL's Mechanism of Action", Transcatheter Cardiovascular Therapeutics, Peripheral IVL Speaker Deck, believed to be presented Oct. 29, 2024.
Begun, Frank P., "Modes of Intracorporeal Lithotripsy: Ultrasound Versus Electrohydraulic Lithotripsy Versus Laser Lithotripsy", Seminars in Urology, vol. 12, No. 1, Feb. 1994, pp. 39-50.
Grocela et al., "Intracorporeal Lithotripsy: Instrumentation and Development", Urologic Clinics of North America, vol. 24, No. 1, Feb. 1997, pp. 13-23.
Kereiakes et al., "Principles of Intravascular Lithotripsy for Calcific Plaque Modification", JACC: Cardiovascular Interventions, vol. 14, No. 12, Jun. 28, 2021, pp. 1275-1292.
Lee et al., "Intravascular Lithotripsy for Calcified Left Main Artery Disease", Journal of the Society for Cardiovascular Angiography and Interventions, vol. 2, 2023, pp. 1-6.
Papatsoris et al., "Update on Intracorporeal Laser Lithotripsy", Minerva Medica, vol. 104, No. 1, 2013, pp. 55-60.
Scotland et al., "Stone Technology: Intracorporeal Lithotripters", World Journal of Urology, vol. 35, 2017, pp. 1347-1351.
Seshiah et al., "Novel Lithotripsy-Assisted Transcatheter Aortic Valve Replacement May Reduce Risk of Aortic Root Rupture", Journal of the Society for Cardiovascular Angiography and Interventions, vol. 2, 2023, pp. 1-4.
Shockwave C2. "Coronary IVL System Step-by-Step Setup", Shockwave Medical, Inc., Exhibit 2163, Provided as part of case IPR2019-00405, U.S. Pat. No. 8,956,371.
Shockwave Medical, Investor Presentation, Slides 7-23 (Nov. 2022).
Vorreuther et al., "Impact of Shock Wave Pattern and Cavitation Bubble Size on Tissue Damage During Ureteroscopic Electrohydraulic Lithotripsy", The Journal of Urology, vol. 153, Mar. 1995, pp. 849-853.
Zheng et al., "Intracorporeal Lithotripsy: Update on Technology", Urologic Clinics of North America, vol. 27, No. 2, May 2000, pp. 301-313.

* cited by examiner

Fluid Reservoir

Fluid Supply Line

Fluid Channel

Fluid Aperture

600

600

300

302

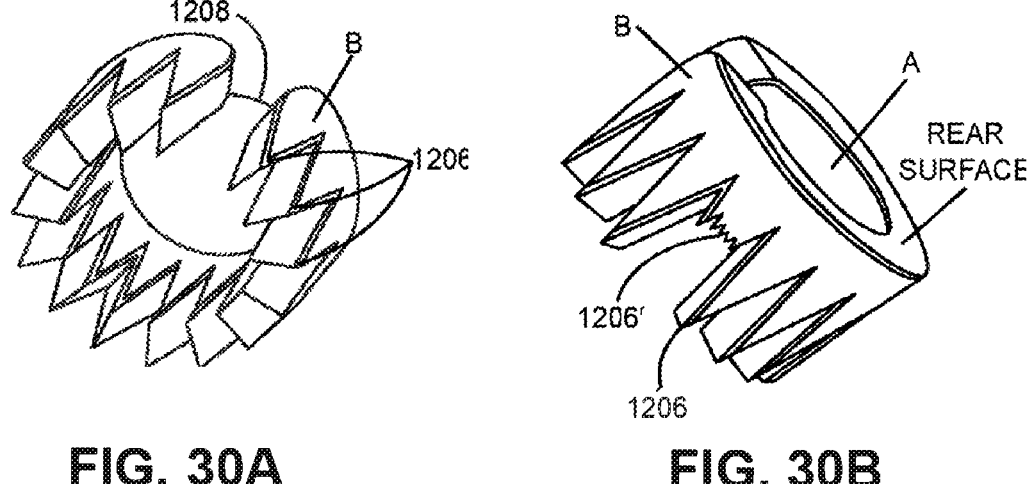
FIG. 30A            FIG. 30B
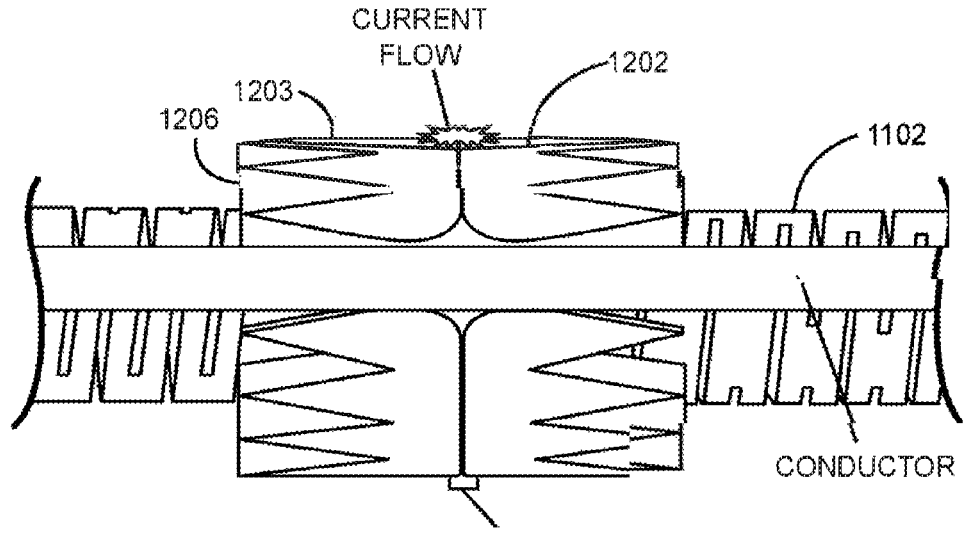
FIG. 31

INTRAVASCULAR LITHOPLASTY BALLOON SYSTEMS, DEVICES AND METHODS

CROSS-REFERENCE TO RELATED APPLICATIONS

This is a 371 application based on PCT/US2022074607, filed Aug. 22, 2022, entitled INTRAVASCULAR LITHO-PLASTY BALLOON SYSTEMS, DEVICES AND METH-ODS and claims the benefit of U.S. Provisional Patent Application Ser. No. 63/229,737, filed Aug. 5, 2021, entitled SYSTEMS, DEVICES AND METHODS FOR GENERAT-ING SUBSONIC PRESSURE WAVES IN INTRAVASCU-LAR LITHOTRIPSY, U.S. Utility patent application Ser. No. 17/449,883, filed Oct. 4, 2021, entitled SYSTEMS, DEVICES AND METHODS FOR GENERATING SUB-SONIC PRESSURE WAVES IN INTRAVASCULAR LITHOTRIPSY, U.S. Utility patent application Ser. No. 17/454,574, filed Nov. 11, 2021, entitled SYSTEMS, DEVICES AND METHODS FOR GENERATING SUB-SONIC PRESSURE WAVES IN INTRAVASCULAR LITHOTRIPSY, U.S. Utility patent application Ser. No. 17/454,587, filed Nov. 11, 2021, entitled SYSTEMS, DEVICES AND METHODS FOR GENERATING SUB-SONIC PRESSURE WAVES IN INTRAVASCULAR LITHOTRIPSY, U.S. Utility patent application Ser. No. 17/454,667, filed Nov. 12, 2021, entitled METHODS, SYS-TEMS AND DEVICES FOR GENERATING SUBSONIC PRESSURE WAVES IN INTRAVASCULAR LITHO-TRIPSY, U.S. Utility patent application Ser. No. 17/454,668, filed Nov. 12, 2021, entitled METHODS FOR GEN-ERATING SUBSONIC PRESSURE WAVES IN INTRAVASCULAR LITHOTRIPSY WITH MORE THAN SPARK GAP, U.S. Utility patent application Ser. No. 17/454,718, filed Nov. 12, 2021, entitled SYSTEMS, DEVICES AND METHODS FOR SELECTION OF ARC LOCATION WITHIN A LITHOPLASTY BALLOON SPARK GAP, U.S. Utility patent application Ser. No. 17/454,721, filed Nov. 12, 2021, entitled SYSTEMS, DEVICES AND METHODS FOR MONITORING VOLT-AGE AND CURRENT AND CONTROLLING VOLTAGE OF INTRAVASCULAR SUBSONIC LITHOTRIPSY SYS-TEMS, and U.S. Utility patent application Ser. No. 17/644,173, filed Dec. 14, 2021, entitled LITHOPLASTY BAL-LOON SYSTEMS, DEVICES AND METHODS WITH ELECTRODE PAIRS HAVING MULTIPLE SPARK GAPS, the entire contents of which are incorporated herein by reference.

STATEMENT REGARDING FEDERALLY SPONSORED RESEARCH OR DEVELOPMENT

None

BACKGROUND OF THE INVENTION

Field of the Invention

The invention relates to systems, devices and methods for breaking up calcified lesions in an anatomical conduit. More specifically, an electrical arc is generated between two spaced-apart electrodes disposed within a fluid-filled mem-ber, creating flow and pressure waves.

Description of the Related Art

A variety of techniques and instruments have been devel-oped for use in the removal or repair of tissue in arteries and similar body passageways, including removal and/or crack-ing of calcified lesions within the passageway and/or formed within the wall defining the passageway. A frequent objec-tive of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque, often within the vessel wall. Such atheromas restrict the flow of blood, cause the vessel to be less compliant than normal, and therefore often are referred to as stenotic lesions or stenoses, the blocking material being referred to as stenotic material. If left untreated, such stenoses can cause angina, hypertension, myocardial infarction, strokes and the like.

Angioplasty, or balloon angioplasty, is an endovascular procedure to treat by widening narrowed or obstructed arteries or veins, typically to treat arterial atherosclerosis. A collapsed balloon is typically passed through a pre-posi-tioned catheter and over a guide wire into the narrowed occlusion and then inflated to a fixed pressure. The balloon forces expansion of the occlusion within the vessel and the surrounding muscular wall until the occlusion yields from the radial force applied by the expanding balloon, opening up the blood vessel with a lumen inner diameter that is similar to the native vessel in the occlusion area and, thereby, improving blood flow.

The angioplasty procedure presents some risks and com-plications, including but not limited to: arterial rupture or other damage to the vessel wall tissue from over-inflation of the balloon catheter, the use of an inappropriately large or stiff balloon, the presence of a calcified target vessel; and/or hematoma or pseudoaneurysm formation at the access site. Generally, the pressures produced by traditional balloon angioplasty systems is in the range of 10-15 atm, but pressures may at times be higher. As described above, the primary problem with known angioplasty systems and meth-ods is that the occlusion yields over a relatively short time period at high stress and strain rate, often resulting in damage or dissection of the conduit, e.g., blood vessel, wall tissue.

Shockwave Medical, Inc., markets an alternative to tra-ditional relatively high pressure balloon angioplasty. An exemplary prior art intravascular lithotripsy system 20 is illustrated in FIG. 1, an image taken from U.S. Pat. No. 9,072,534 to Shockwave Medical, Inc. FIG. 1 illustrates a pulse generator 30 with 2 insulated conductors, each having a distal-most end stripped of insulation to form electrodes 22 and 24. As shown, the electrodes 22 and 24 are spaced apart to form an electrode pair with a gap therebetween. An arc occurs between the electrodes when sufficient voltage is applied to one of the insulated conductors. Electrodes 22 and 24 are placed within a fluid-filled balloon 26 and a shock wave is generated which passes through the balloon 26.

Known systems developed and marketed by Shockwave Medical, Inc., systems require a relatively close spacing between electrodes in an electrode pair and produce the desired arc between the relatively closely spaced-apart elec-trodes using the relatively large volume of fluid in an inflatable angioplasty balloon while the balloon is in an inflated state producing, e.g., 4 atm of pressure. For these, among other, reasons Shockwave Medical's currently known systems provides relatively small axial coverage of lesions with a single shock wave generator comprising two spaced-apart electrodes. Typical distances between spaced-apart electrodes in known systems are approximately 0.004 in +/−0.001 in, or 0.1 mm. Thus, to cover an elongated lesion, the structure of Shockwave Medical's electrode pairs thus requires additional electrode pairs (all of which have relatively short spacing between the electrodes in a pair of electrodes) to be disposed along an elongate carrier and/or a translatable, slidable electrode pair carrier that may be used to translate the electrode pair(s).

It would be advantageous to provide, inter alia, a system capable of producing longer arcs in order to generate more energy during an arcing event than the energy generated with relatively shorter gaps between electrodes. It would be further advantageous to provide a system that maintains a safe temperature of the balloon fluid as a result of energizing the electrodes to form a longer current arc across a relatively longer gap.

Various embodiments of the present invention address these issues, among others, discussed above.

BRIEF DESCRIPTION OF THE SEVERAL VIEWS OF THE DRAWINGS

These drawings are exemplary illustrations of certain embodiments and, as such, are not intended to limit the disclosure.

FIG. 30A illustrates a front perspective view of one embodiment of the present invention.

FIG. 30B illustrates a side perspective view of the embodiment of FIG. 32A following corrosion or erosion of part of the structure during arcing.

FIG. 31 illustrates a side cutaway view of one embodiment of the present invention.

DETAILED DESCRIPTION OF THE INVENTION

Typical and known balloon angioplasty applies hydrostatic pressure (and associated tensile force) in the range of 1 atm to 20 atm for a time period of 0.1 s to 100 s, which acts to expand the flow channel diameter of a blood vessel adjacent to or partially surrounded by a plaque. If the plaque is compliant (e.g. not calcified, or only partially calcified), this nearly-static pressure cycling is sufficient for treatment. If the plaque is not compliant (e.g. calcified) and the plaque extends nearly circumferentially around the vessel, the hoop stress in the plaque created by this nearly-static pressure cycling can fracture the calcifications, again being sufficient for treatment.

Plaques that do not respond to the known angioplasty pressure cycling may be treated by pressure cycling on other time scales with alternative mechanisms.

Figure 1:
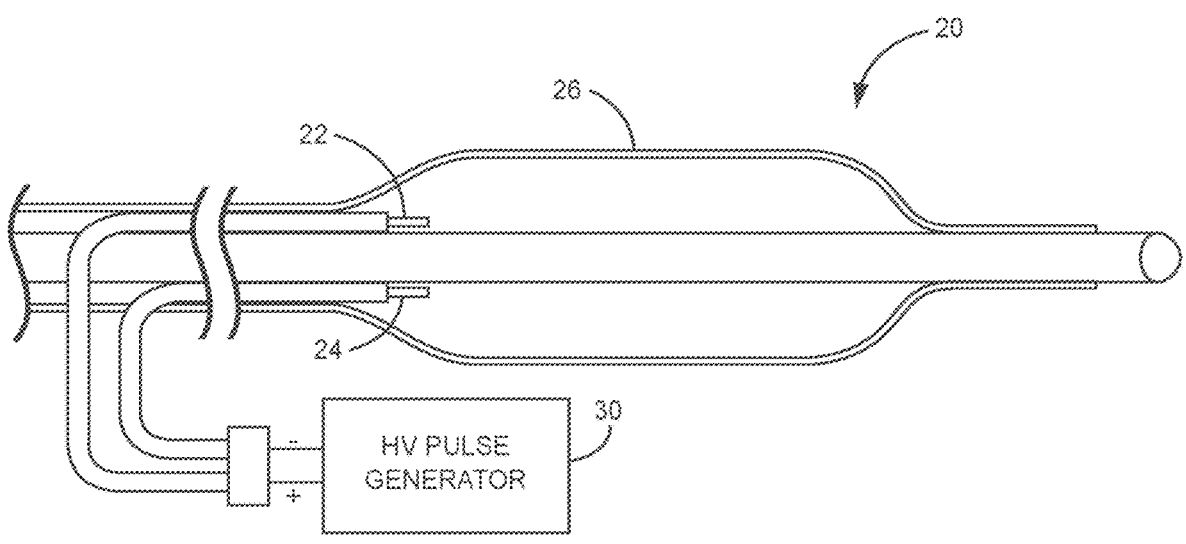
FIG. 1 illustrates a prior art system.
Figure 2:
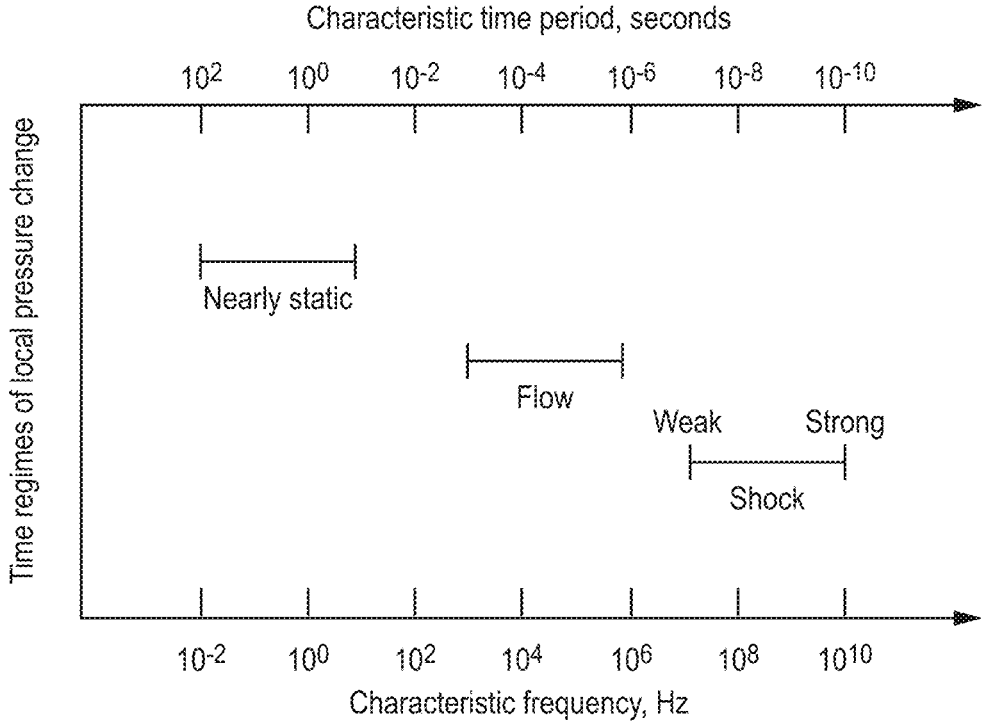
FIG. 2 illustrates regimes of plaque treatment in terms of the time variability of pressure.

Two regimes are of importance: pressure (and tensile forces) at the plaque that change on the timescale of 10 usec to 10 ms, herein defined as flow pulses or flow waves or flow which travel at subsonic speed; and pressure (and tensile forces) at the plaque that change on the timescale of 1 ns to 1 usec, hereby defined as pressure waves or shock waves or blast waves or shock which travel at least at the speed of sound. FIG. 2 provides an exemplary graph of time regimes related to local pressure change. The plaque treatment improvements described below are mostly associated with the flow and shock regimes.

An example of a flow wave or pulse is a displacement wave produced in the tissue by the flexing of the surface of the balloon following a boiling or arcing event inside the balloon as is known in the art. As a portion of the liquid inside the balloon is turned to gas, its density drops by on the order of a factor of a thousand, increasing the volume that the balloon is inclined to occupy. Generally a bubble generated by ohmic heating using intense ionic currents is a steam pocket that expands and contracts again in tens to hundreds of microseconds, performing a faster version of the nearly-static balloon inflation.

An example of the pressure or shock wave is the pressure wave created when the blast from the initial arc discharge between the electrodes in the balloon impacts the saline in the balloon.

Figure 3:
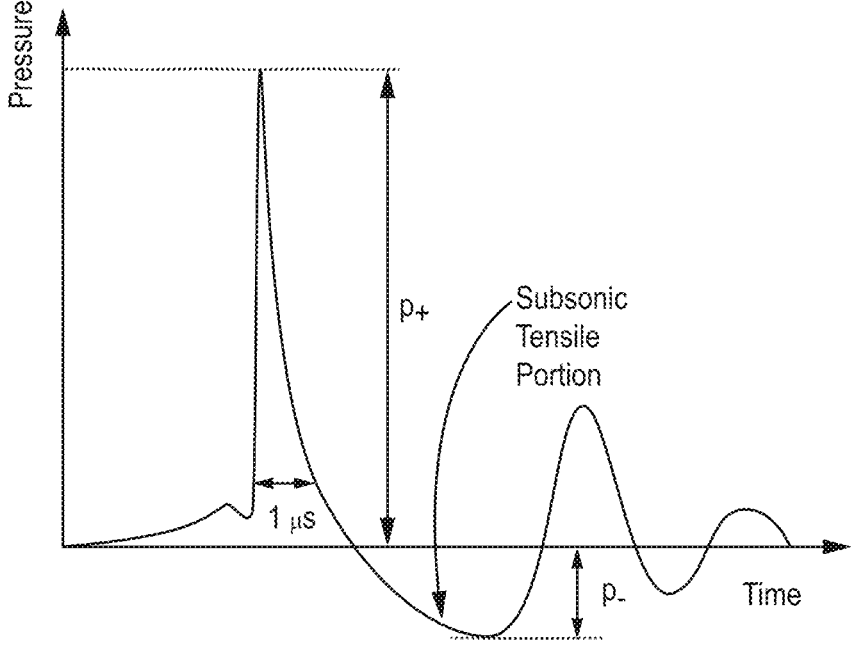
FIG. 3 illustrates the time dependent pressure at a plaque due to an incident shock wave.

FIG. 3 shows a typical example of the local pressure experienced by a region of the tissue near that discharge. The abrupt rise to pressure p+ (the pressure phase) followed by a drop below the steady state pressure to p− (the tensile phase) is indicative of a shock wave. The velocity of a shock wave is faster than the speed of sound immediately adjacent to the blast or arc, and asymptotes to the speed of sound at larger distances. The tensile phase lags the pressure phase by an increasing amount of time for larger distances from the discharge, so that when the pressure phase asymptotes to the speed of sound, the tensile wave is traveling slightly slower than the speed of sound. Accordingly, subsonic and sonic wave speeds are produced during balloon lithoplasty procedures.

Figure 4:
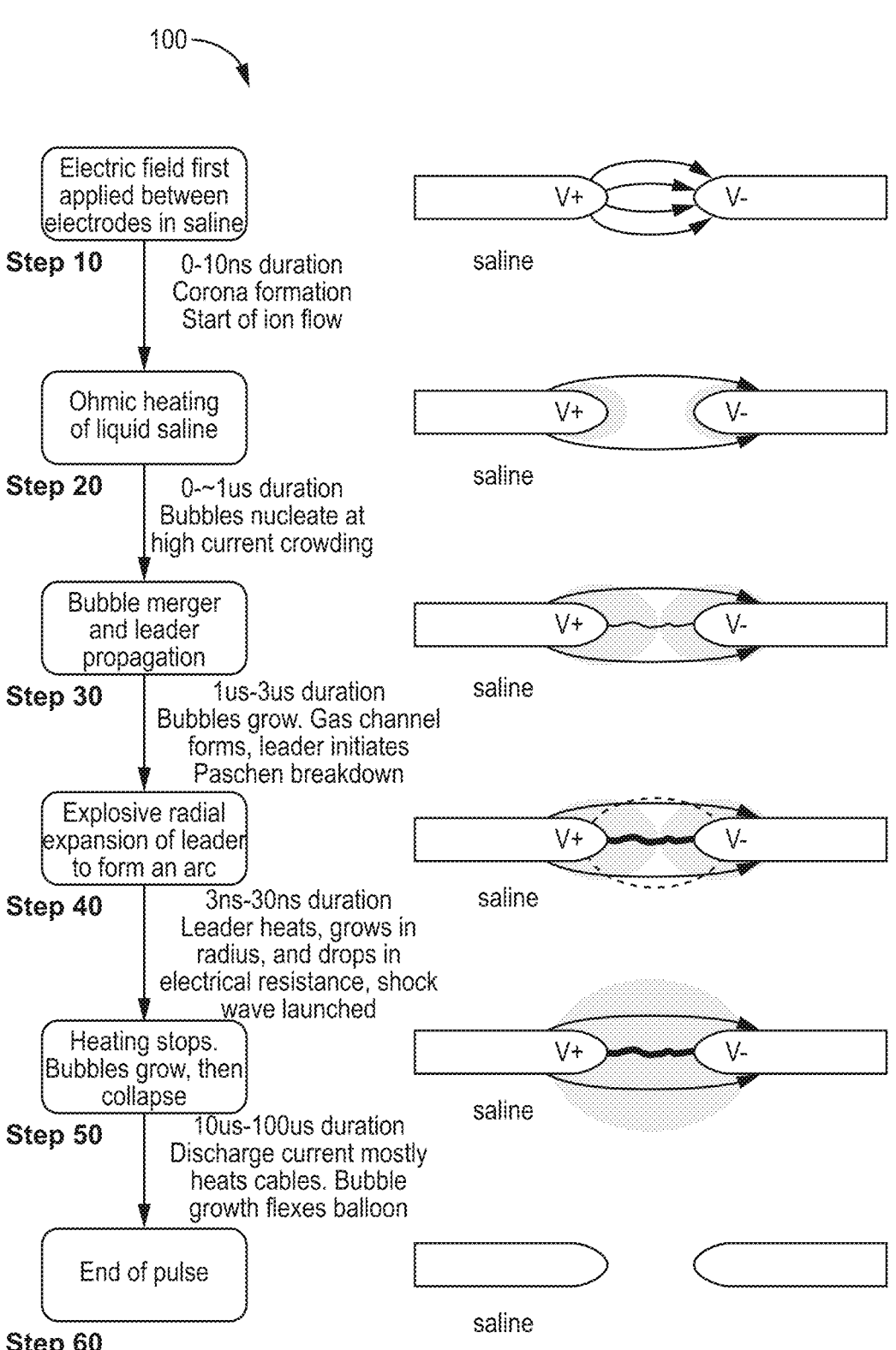
FIG. 4 illustrates the sequence of events whereby a current pulse through electrodes produces flow and pressure waves.

An initial shock wave generated by known lithotripsy balloon systems results from a multi-step process 100, with basic steps 10-60, as shown in FIG. 4. In the first step 10, two electrodes, E1 and E2 in contact with saline, an ionically conductive fluid, have a substantial voltage applied between them by an external power source. Quickly after the voltage is applied, corona discharges originate from the surfaces of the electrodes and an ionic current flows (shown as arrows) between the electrodes E1 to E2 through the saline.

Once the ionic currents are established, there is a relatively long time, 0.3 us to 1 ms depending on the fluid and the electrode geometry and the voltage, where the fluid (saline) heats. The current crowding is generally (but not necessarily) highest at the electrodes E1, E2, so the fluid will tend to boil at the electrodes E1, E2 first as seen in step 20. As saline is mostly water, it obeys the boiling characteristics of other prompt boiling systems, such as bubble jet print heads; water will locally boil spontaneously in a time frame of microseconds or less at 350° C. or more. FIG. 4 shows a typical case of boiling initiating at nearly the same time at both electrodes E1, E2 and the resulting bubbles growing at nearly the same rate therefrom.

The steam pockets produced by local boiling are initially at high internal pressure, so they expand quickly. Steps 20-40 of FIG. 4 shows the steam pockets or bubbles expanding, resulting in their merger into a contiguous gas pocket connecting the two electrodes. A leader, a microscopically thin streamer of ions and electrons in the gas, shown in steps 30-50, can form through the saline steam connecting the electrodes when there is a continuous gas path between the electrodes, and when the pressure, temperature, voltage, and electrode spacing satisfy Paschen's law, which says that the voltage $V_B$ required to initiate breakdown in a gas with static pressure $p_g$ across an interelectrode distance $d_e$ satisfies $$V_B = \frac{B \ p_g \ d_e}{\ln(A \ p_g \ d_e) - \ln\left[\ln\left(1 + 1/\gamma_{se}\right)\right]}$$

where A and B are constants for a gas composition, and $\gamma_{se}$ is a secondary electron emission coefficient. Generally, the leader is able to form for a sufficiently high electric field strength and a sufficiently low gas pressure. It is less favorable to initiate a discharge in liquid saline, since the average time between collisions for ions in solution is so short that the acceleration experienced by the ions in the electric field is insufficient to generate additional secondary electrons and ions during subsequent collisions.

When the leader first forms, see step 30, it is conceptually an ion channel of small radius connecting the two electrodes. Electrons flow to the anode, and positive ions in the channel flow to the cathode. Despite the ion channel having a high conductivity, it has a relatively high electrical resistance when it first forms due to its small radius. Examples of the initial leader resistance for this process are in the range of a kilo ohm to an ohm.

The electric field from the voltage applied across the electrodes drives current through the leader as shown in steps 40 and 50 of FIG. 4. Because of the high current density with the high voltage difference, the leader heats quickly, expanding radially as it heats, which results in reduction of the resistance of the leader. In roughly 10 ns to 30 ns, as in step 40, the resistance of the leader drops below the series resistance of the conductors in the catheter transporting the drive current from the external pulse generator. Once the leader has expanded so as to have a low impedance, most of the ohmic heating produced by current from the generator goes into heating the conductors in the catheter which are operatively connected with the electrodes and a voltage or power source.

Figure 5:
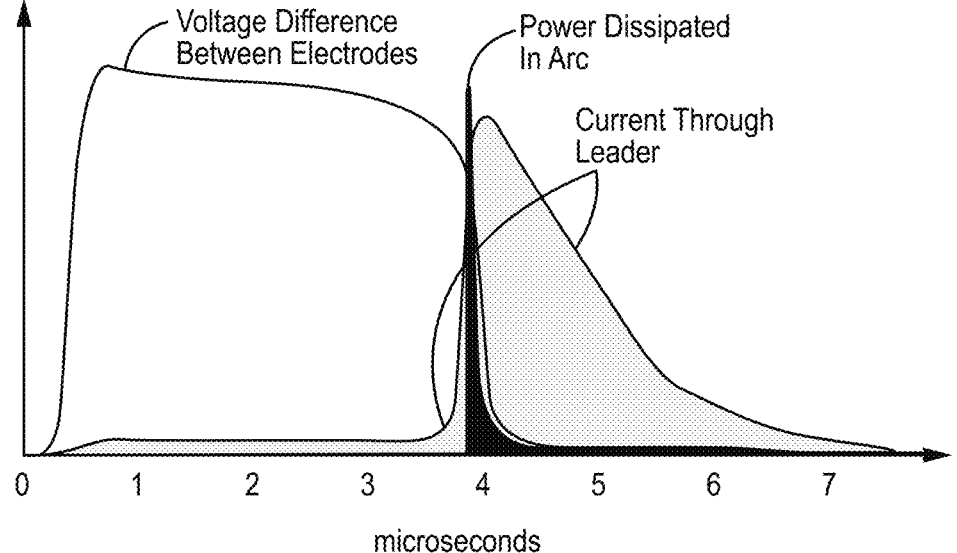
FIG. 5 illustrates a typical timing of the current and voltage through the electrodes.

FIG. 5 illustrates the drop in impedance of the leader as it develops into an arc, as in step 40 of FIG. 3, causing the power dissipated in the arc to peak sharply while the voltage and current between the electrodes are both relatively high. The current reaches a peak and the voltage drops, both very rapidly, indicating that an arc between the electrodes is present. The peak of the power dissipated in the arc indicates the relatively short time interval during which all the useful work of heating the growing leader into an arc is performed.

Figure 6:
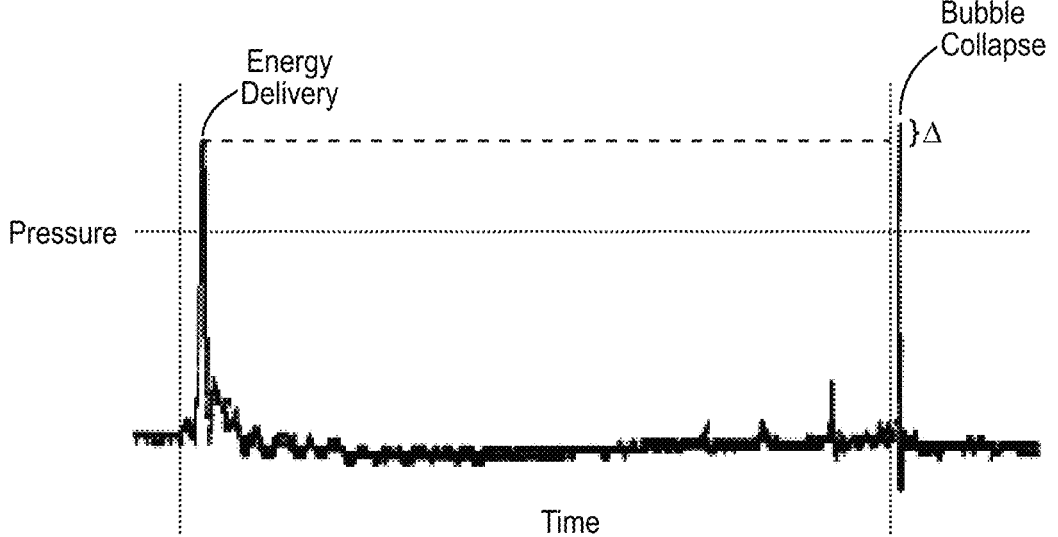
FIG. 6 illustrates a typical sequence of energy production peaks during bubble formation and collapse.

FIG. 6 illustrates the pressure waves produced by the process described in FIGS. 4 and 5 as pressure over time. The initial pressure magnitude peak is a hydrophone measurement of the shock wave that has propagated, produced as energy is delivered to the electrodes, a bubble has formed, and the leader through the bubble has expanded into an arc. The second pressure magnitude peak corresponds with the collapsing of the formed bubble to produce a cavitation shock wave. It is noteworthy that the initial pressure peak is less than the second, or bubble collapse, pressure peak as indicated by pressure differential Δ.

The ability of the waves in these regimes to treat plaques is generally discussed in the art as being monotonic in the pressures experienced by the plaque. Our present understanding of plaque treatment is that one or more of the following processes contribute to varying degrees:

1. Yield or creep of the atheromatous material under radial, circumferential, and axial forces produced by nearly-static balloon inflations of up to 20 atm.
2. Yield or creep of the atheromatous material under radial, circumferential, and axial forces produced by flow displacements of the balloon, which may momentarily exceed the nearly-static pressurized displacements.
3. Tensile and shear forces during the tensile phase of the shock wave passing through the calcified material, causing crack propagation in the calcified material.
4. Conversion of the peak pressure in a shock wave to tensile force by transmission and or reflection of the shock wave at acoustic mismatches in the plaque (such as the surface between fatty tissue and calcifications). This is probably the dominant treatment mechanism.

5. Tensile forces, like the previously mentioned conversion of a peak pressure wave to a peak tensile wave on reflection, creating cavitation, which in turn generates subsequent shock waves due to cavitation collapse, which in turn distributes additional tensile forces.

6. Swelling of shock-induced cracks by capillary flow into the cracks, in a manner similar to fracking to break up rocky formations for oil extraction.

7. Complimentary combinations of the above effects, such as a flow event inducing flexing and liquid flow into calcification cracks newly manufactured by a shock event.

In view of the above mechanisms, optimizing lithoplasty balloon systems and related treatment methods and outcomes involves a balance of the following concepts:

1. A system sufficiently reliable and robust that it does not harm the patient. This is known in the art.

2. A system that is compact enough to be translated through nearly-closed blood vessels. This is known in the art.

3. A balloon, and method to inflate the balloon inflation with saline and indicator, so that nearly static treatment can be applied, and so treatment efficacy can be measured in terms of the final blood vessel open diameter. This is known in the art.

4. Electrical (or other, e.g., laser or ultrasound) steam-bubble generation within the balloon, along with a reduced balloon inflation configuration, enabling a rapid flexing of the balloon surface and generation of a flow wave. This is not known in the art.

5. Launching a shock wave with the highest peak pressure and lowest tensile wave pressure. This equates to maximizing the electrical energy expended when the arc initiates, and optimizing the length and orientation of the arc. This is not known in the art.

6. Positioning the source of the shock wave as close as possible to the plaque, to reduce the extent that the peak shock pressure decays with distance between the source and the plaque. Mechanisms for achieving this as described herein are not known in the art.

7. Minimizing the thermal heating produced by treatment. Mechanisms for achieving some or all of the above objectives as described herein, with reduced or minimized thermal heating are not known in the art.

8. Delays between treatment pulses can allow capillary flow into cracks created by previous pulses, speeding up overall treatment. This is not known in the art.

It is known to the artisan that shock waves propagate in a similar manner regardless of the mechanism that generates them. The peak pressure of a strong shock wave at a radial distance r from the initial point source blast is proportional to the energy of the initial blast $E_0$, and to the inverse cube of the radius from the point source:

$$p_{max}(r) = k\frac{E_0}{r^3}$$

See Hans Bethe, Klaus Fuchs, Joseph Hirshfelder, John Magee, Rudolph Peierls, and John von Neumann, *Blast Wave*, Martino Publishing, 2013, p. 49, Eq.2.48.

At intermediate distances from the source, the shock wave slows down from its initial supersonic velocity, and the spatial thickness of the wave from expands. At these intermediate distances, the pressure dependence becomes approximately $$p_{max,point}(r) = k\left(\frac{\sqrt[3]{2E_0}}{r}\right)^{1.16}$$

If the blast source is a line of length $L_{arc}$, and $r < 3\,L_{arc}$, and 'R is in the plane that bisects the line, then the dependence of pressure on range r becomes $$p_{max,line}(r) = k\left(\frac{\sqrt[3]{2E_0}}{r}\right)^{0.5}$$

Cole, *Underwater Explosions*, Princeton University Press, 1948, pp. 122-7.

Optimizing the peak pressure experienced by the targeted plaque therefore requires: (1) depositing as much energy as is practical in the initial times or portion of the discharge; and (2) minimizing the distance between the discharge and the targeted plaque.

Thus, a linear arc of length $L_{arc}$ will generate a shock wave whose intensity varies with respect to the orientation of the arc. In the axial, or longitudinal, direction, a linear blast source will produce less peak pressure than a point source of equal initial energy, and in the radial direction the peak pressure will be greater, at least for distances from the source that are on the order of $L_{arc}$. In the radial direction, the peak pressure experienced by a plaque a distance r from the center of a linear arc will have the form $$p_{max\text{-}line}(r) = k_{line}\frac{E_0}{r^n}$$

where $0.5 \le n \le 3$. For $r >> L_{arc}$, n=appx 1.16; the linear arc acts like a point source. For very short distances, $r << L_{arc}$, n=appx 1.16. For short distances up to: r=appx $L_{arc}$, n=appx 0.5; the shock wave does not decay as quickly. Relatively long arcs oriented to preferentially broadcast towards the plaques will, therefore, be more efficient at converting the electrical energy associated with the blast to pressure (and tension) effects in the targeted and at least partially calcified plaques.

Subsequent to the arc stabilizing to a low impedance 'steady' state, it does not matter much to the treatment if the voltage pulse continues is quickly shut off by active control, or if it sags over time as the storage capacitors driving the pulse discharge their stored energy.

Based on the above understanding of the causal sequence produced by the voltage pulsed applied to the electrodes, at least the following concepts emerge:

A. The energy in a shock wave produced within a fluid-filled balloon is primarily determined by the energy dissipated in the growth of the leader as it becomes a stable arc. For a fixed distance between electrodes, the energy dissipated in the growth of the leader to form an arc is determined primarily by the applied voltage, electrode distance and the catheter cable impedance.

a. Longer arcs can release more energy. A long leader has a higher initial resistance, and so can convert more of the voltage and current to heat.

b. Lower impedance catheter cabling can supply more energy to the leader during its growth phase, releasing more energy.

c. Higher voltage lets the leader form at a higher pressure, it increases the rate of heating of the leader, and it releases more energy.

B. The heat dissipated in forming the discharge between the electrodes is dominated by ionic conduction through the saline prior to forming the saline-steam path between the electrodes and its subsequent Townsend breakdown. As all paths through the saline fluid connecting the electrodes will conduct current in parallel, the paths sampling large portions of the balloon's saline volume will slowly heat, adding to tissue heating without contributing to boiling.

a. The volume of saline that participates in ionic conduction prior to arc formation should be constrained or minimized, and preferably, to a channel connecting the electrodes in the immediate vicinity of the electrodes.

C. A long arc preferentially drives shock waves normal to the axis of the arc. To the extent that treatment is being performed in the shock regime, it should be aided by orienting the arc so that the plaque is in that normal direction.

Moreover, some of the above embodiments and concepts act to enable others. For example, if the gap between two electrodes in saline is increased, the ionic resistance between the electrodes increases and the average ionic current density between the electrodes decreases. As a result, the amount of energy dissipated by the pulse generator in heating saline in the balloon to reach boiling increases non-linearly with electrode spacing. To achieve the desirable longer arcs, it becomes desirable to limit the saline participating in the ionic conduction to a small channel connecting the electrodes. In this manner, the heating energy required increases only linearly with gap.

Creating a long arc in saline is not a simple matter of moving the electrodes apart and increasing the voltage. The following examples clarify the issues involved.

Figure 7A:
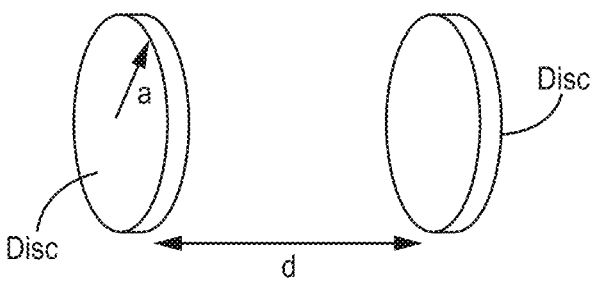
FIG. 7A provides two exemplary discs representing electrodes spaced a distance apart with geometries for the electrodes and ionic current confinement.

In FIG. 7A, two conducting disks, representing exemplary electrodes within a fluid medium, of radius a are separated by d in a medium of conductivity σ. The ionic resistance between the disks is $$R_{disks} = \frac{d}{\pi\, a^2 \sigma}$$

Figure 7B:
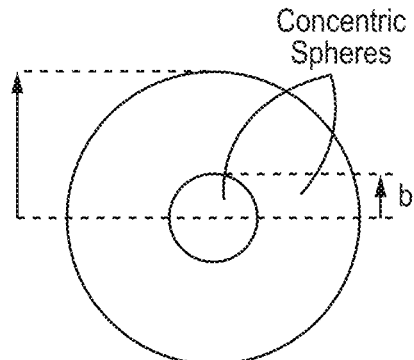
FIG. 7B provides concentric conductive spheres representing electrodes.

In FIG. 7B, conducting concentric spheres of radii a and b are again separated by a medium of conductivity σ. The ionic resistance between the spheres is $$R_{spheres} = \frac{a-b}{4\pi ab\sigma}$$

Figure 7C:
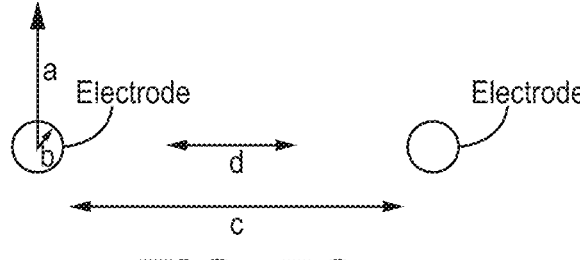
FIG. 7C provides spaced-apart conductive spheres representing electrodes and related geometries.

Approximate the resistance of half-sphere electrodes of radius b within a balloon of radius a separated by c=d+2(a−b)

as the sum of $R_{disks}$ and 4 $R_{spheres}$ (current only goes through half the 'sphere' at each electrode, so the resistance there is doubled, and this occurs at both electrodes) shown in FIG. 7C:

$$R_{electrodes} \sim \frac{d}{\pi a^2 \sigma}\left(1 + \frac{a(a-b)}{bd}\right)$$

The volume of medium of conductivity σ carrying current is $$V_{fluid} = \pi a^2 d + \frac{4}{3}\pi(a^3 - b^3)$$

A voltage $V_0$ applied between the electrodes dissipates power $$V_0^2/R_{electrodes}.$$

If the medium has heat capacity Cp and density ρ, the average rate of temperature rise of the medium is $$\left.\frac{dT}{dt}\right|_{ave} = \frac{V_0^2}{R_{electrodes}V_{fluid}\rho Cp} = \frac{V_0^2}{\rho Cp}\frac{\sigma}{\left(d+a\left(\frac{a}{b}-1\right)\right)\left(d+\frac{4(a^3-b^3)}{3a^2}\right)}$$

Consider three limiting case geometries of the exemplar of FIG. 7C. In the first case, a is large compared to the electrode radius b. If the separation of the electrodes is also less than a, the heating rate in this unconfined case becomes $$\left.\frac{dT}{dt}\right|_{ave-unconfined} = \frac{V_0^2}{\rho Cp}\frac{3\sigma b}{4a^3}$$

and the resistance becomes $$R_{unconfined} \sim \frac{1}{\pi b\sigma}$$

In the second case, a~b; the medium is confined to a cylinder between the electrodes that is about the same area normal to the current flow as the electrodes. In this confined case the heating rate becomes $$\left.\frac{dT}{dt}\right|_{ave-unconfined} = \frac{V_0^2}{\rho Cp}\frac{\sigma}{d^2}$$

and the resistance becomes $$R_{confined} \sim \frac{d}{\pi a^2 \sigma}$$

The confined case heats up on average faster by a factor of 4 $a^3$/(3 b $d^2$). The confined case dissipates less power by a factor b d/$a^2$. For example, the confined case of electrodes with a radius b=0.05 mm separated by d=0.5 mm driving current through a fluid channel between them also of radius 0.05 mm will heat the fluid on average 6,800 times faster while using 0.2% of the power compared to the unconfined case where the balloon with interior radius a=4 mm limits the ionic current from electrodes of the same size and spacing.

A third limiting case is when the distance between the electrodes approaches the diameter of the electrodes; in this case the current crowding regions near the electrode surfaces overlap, producing a thermal efficiency between the confined and unconfined cases.

The merits of a confined or constrained ionic current channel leading, in turn, to longer arcs between the electrodes are not obvious in view of prior art designs primarily because of the shorter arc lengths of those designs.

To reduce the amount of heat dissipated in the saline during the boiling phase, the ionic currents should be confined to the extent possible to a narrow channel connecting the electrodes. This also reduces the fraction of the energy stored at high voltage in the power supply that is expended on heating rather than arc generation.

Partially collapsing the balloon around the electrode pair(s) acts to form that narrow channel of fluid between and the spaced-apart electrodes in an electrode pair. Other mechanisms to confine or constrain fluid around the electrodes are provided infra.

Long arcs (those greater than about 0.5 mm) are impractical within an inflated balloon without some additional mechanism to limit the saline volume the ionic current can access. Generally, this is because the heating rate is increased linearly with the saline conductivity and creating long arcs without appropriate fluid constraining strategies will result in harmful overheating of the fluid during treatment.

As the skilled artisan will now recognize, constraining or confining the fluid to a smaller, narrower channel or volume around or between the electrodes is a technique that may be implemented with, and enables, longer arcs (greater than about 0.5 mm) and/or shorter arcs, i.e., those less than 0.5 mm with safe levels of heat generation. The embodiments described below will have beneficial effects for gaps between spaced-apart electrodes, and the arcs generated therebetween, that have a length between 0.1 mm and 15 mm.

Figure 8:
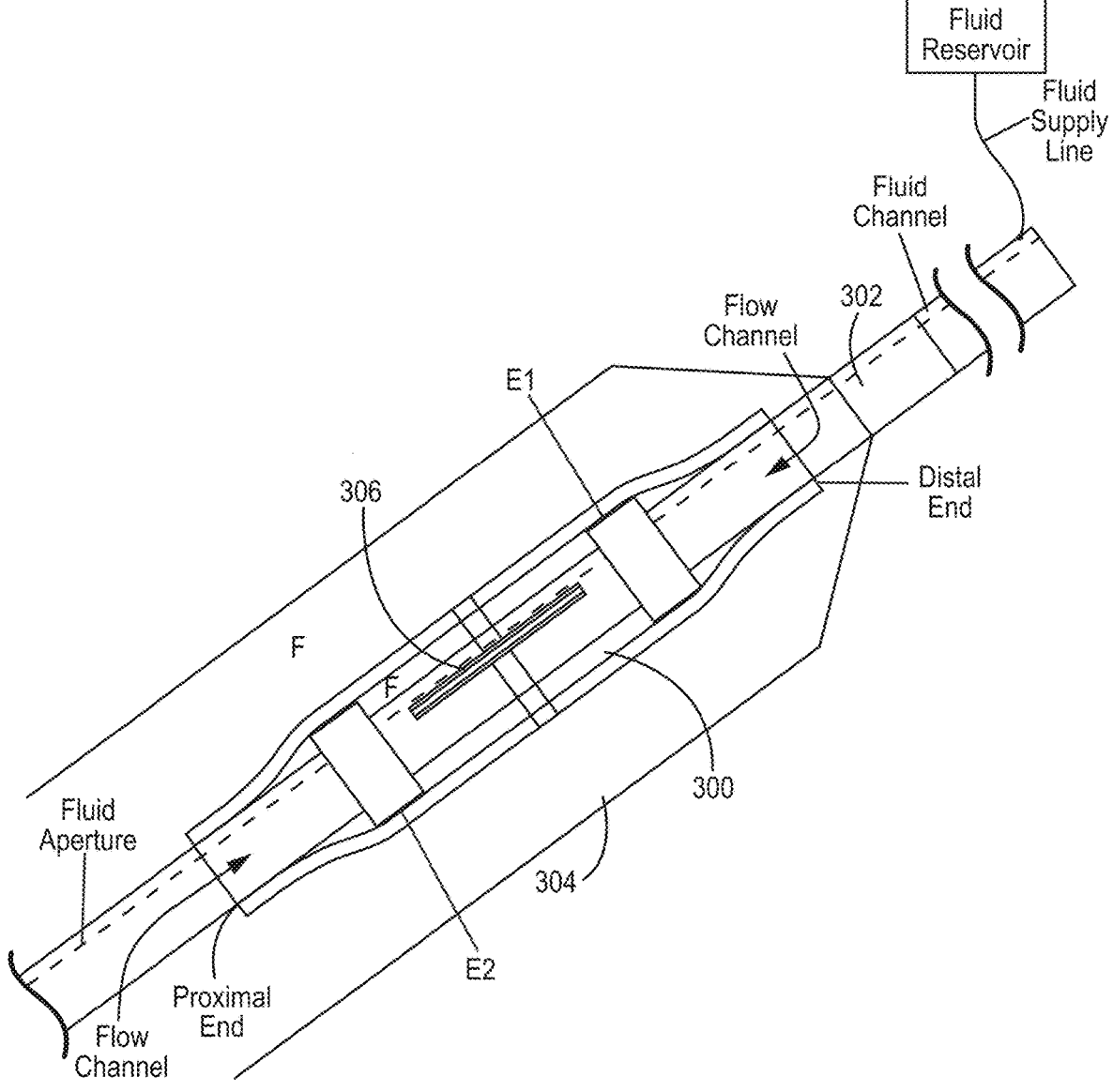
FIG. 8 illustrates a side cutaway view of one embodiment of the present invention.

FIG. 8 provides an example of an exemplary flow and pressure wave generator comprising two spaced-apart electrodes E1, E2 disposed within a fluid constraining or confining structure, shown as exemplary sleeve 300, that provides a narrow channel of fluid F between the electrodes E1, E2. An elongate catheter or member 302 carries the two exemplary electrodes E1, E2 encased within a sleeve that may comprise polymer, e.g., silicone. The sleeve may, in turn, be encapsulated within an inflatable balloon 304 that is sealed to form a water tight interior and comprising fluid F, e.g., saline when at least partially inflated, wherein the inflatable balloon 304 comprises a plurality of inflated configurations, each inflated configuration comprising a different fluid pressure. Each inflated configuration of the inflatable balloon 304 comprises a volume that is larger than the volume of the sleeve 300. Inflatable balloon 300 may, as well known to the artisan, be in fluid communication with a fluid channel via a fluid supply line that is disposed within or along elongate catheter or member 302 and which is, at a proximal end, in communication with a fluid reservoir for inflating and deflating the inflatable balloon through an aperture (which may be valved) in catheter within the interior of the inflatable balloon and which is in fluid communication with a fluid reservoir via a fluid supply line and fluid channel.

Sleeve 300 may be inflatable, but comprises a maximum inflated diameter that is less than the diameter of the inflated balloon 304 so that sleeve 300 in an inflated configuration that narrowly constrains the amount of volume of fluid between the electrodes E1, E2 relative to the amount or volume of fluid within the balloon. In some embodiments, the maximum inflated diameter of the sleeve 300 is 2× or less than of the maximum inflated diameter of the balloon 304. In other embodiments, the maximum inflated diameter of the sleeve 300 is 3× or less than the maximum inflated diameter of the balloon 304. In other embodiments, the maximum inflated diameter of the sleeve 300 is 5× or less than that of the maximum inflated diameter of the balloon 304. In other embodiments, the maximum inflated diameter of the sleeve 300 is 10× or less than of the maximum inflated diameter of the balloon 304.

In addition, the inflated volume of sleeve 300 is less than the inflated volume of the balloon 304. In some embodiments, the maximum inflated volume of the sleeve 300 is 2× or less than of the maximum inflated volume of the balloon 304. In other embodiments, the maximum inflated volume of the sleeve 300 is 3× or less than the maximum inflated volume of the balloon 304. In other embodiments, the maximum inflated volume of the sleeve 300 is 5× or less than that of the maximum inflated volume of the balloon 304. In other embodiments, the maximum inflated volume of the sleeve 300 is 10× or less than of the maximum inflated volume of the balloon 304. In other embodiments, the maximum inflated volume of the balloon 304 is 1.5× or greater than the maximum inflated volume of the sleeve 300.

An exemplary elongate catheter or member 302 diameter may be 1.5 mm (0.20-0.40 in), the exemplary electrode E1, E2 radial thickness may be 0.2 mm (8 mils) (0.002-0.004 in), and an exemplary sleeve 300 thickness may be 0.05 mm (2 mils) (0.0005-0.003 in). Other thicknesses may also be used and are within the scope of the present disclosure and inventions described herein. The conductive wires connecting the electrodes E1, E2 to the power supply or voltage pulse generator are present but not shown but are as known to the artisan and as, e.g., described herein.

An optional laser-cut slot(s) or groove(s) 306 is shown disposed along elongate catheter or member 302 and within the interior of sleeve 300. This optional slot or groove 306. The optional slot or groove acts in its closed or neutral state to isolate ionic current inside the sleeve. Once a boiling event is initiated, the rise in pressure inside the sleeve opens the slot, allowing non-destructive flow out of the sleeve. Between events, saline refills the interior of the sleeve. The response of this embodiment will follow the resistance and time response of the previously calculated confined case.

The exemplary sleeve 300 of FIG. 8 comprises a proximal and a distal end which at least partially surround the elongate catheter or member 302 and which are in at least partial fluid communication with the fluid F of the encapsulating balloon when in an inflated configuration. This allows the fluid of the encapsulating balloon to enter into the exemplary sleeve and provide fluid F into the gap between the two electrodes. Portions of the proximal and/or distal ends of the sleeve 300 may be adhered to and/or tacked to the catheter or member 302 to secure the sleeve 300 in position around the insulated portions of electrodes E1, E2, wherein the sleeve 300 is spaced apart from the uninsulated portions of electrodes E1, E2. Alternatively, portions of the sleeve 300 may be adhered to insulated portions of one or both of the electrodes E1, E2. Preferably, the sleeve 300 comprises silicone which may be placed around the electrodes E1, E2 as shown. Fluid F may be allowed to move from the encapsulating balloon into the sleeve through, e.g., one or more flow channels provided between the elongate catheter or member 302 and a proximal and/or distal end of the sleeve and into the gap between the electrodes E1, E2 via fluid communication with the proximal and/or distal ends of the sleeve 300. Flow channels may be separately defined structures such as a tube or conduit, result as a consequence of an interior surface of the proximal and distal ends of the sleeve 300 being spaced from an outer surface of elongate catheter or member 302.

Applicant has discovered that sleeve 300 may be disposed on or along an outer surface of the flow and pressure wave generators discussed herein and that arcing between spaced-apart electrodes of the flow and pressure wave generators does not adversely affect or damage the sleeve 300. In some embodiments, sleeve 300 may be disposed along a surface of the spaced-apart electrodes of the flow and pressure wave generators discussed infra. These embodiments of the sleeve 300 are applicable to all flow and pressure wave generator embodiments discussed herein, preferably wherein the sleeve 300 comprises silicone.

In some of the embodiments the sleeve 300 may be sealed at the proximal and distal ends and amenable to either active or passive fluid inflow. In a passively filled sleeve 300 embodiment, one or more apertures, slits, holes and the like may be provided at one or more points along the sleeve 300 to allow fluid to flow from the encapsulating balloon into the interior of the sleeve 300.

In alternative embodiments, sleeve 300 may be in fluid communication with a fluid channel disposed within central catheter, wherein the fluid channel is in fluid communication at its proximal end with a fluid reservoir. An aperture, which may be valved, may be disposed through catheter, within the sleeve, and in fluid communication with the fluid channel and the interior of sleeve 300. Fluid channel may be a separate sleeve fluid channel or may be a common fluid channel used for both the sleeve and the inflatable balloon. Alternatively, fluid channel may ride on an outer surface of catheter or member 302, wherein the balloon is sealed around the fluid channel and catheter outer surface. This active inflation and deflation mechanism is well known to the artisan, is also described above in connection with the inflatable balloon 304 and is not shown.

In still another alternative embodiment, the encapsulating inflatable balloon 304 may not be required or provided, such that the sleeve 300 provides the desired narrow channel of fluid F between the electrodes E1 and E2, with inflating and deflating of the sleeve 300 achieved by the fluid reservoir, fluid channel and aperture flow channel described above.

Figure 9:
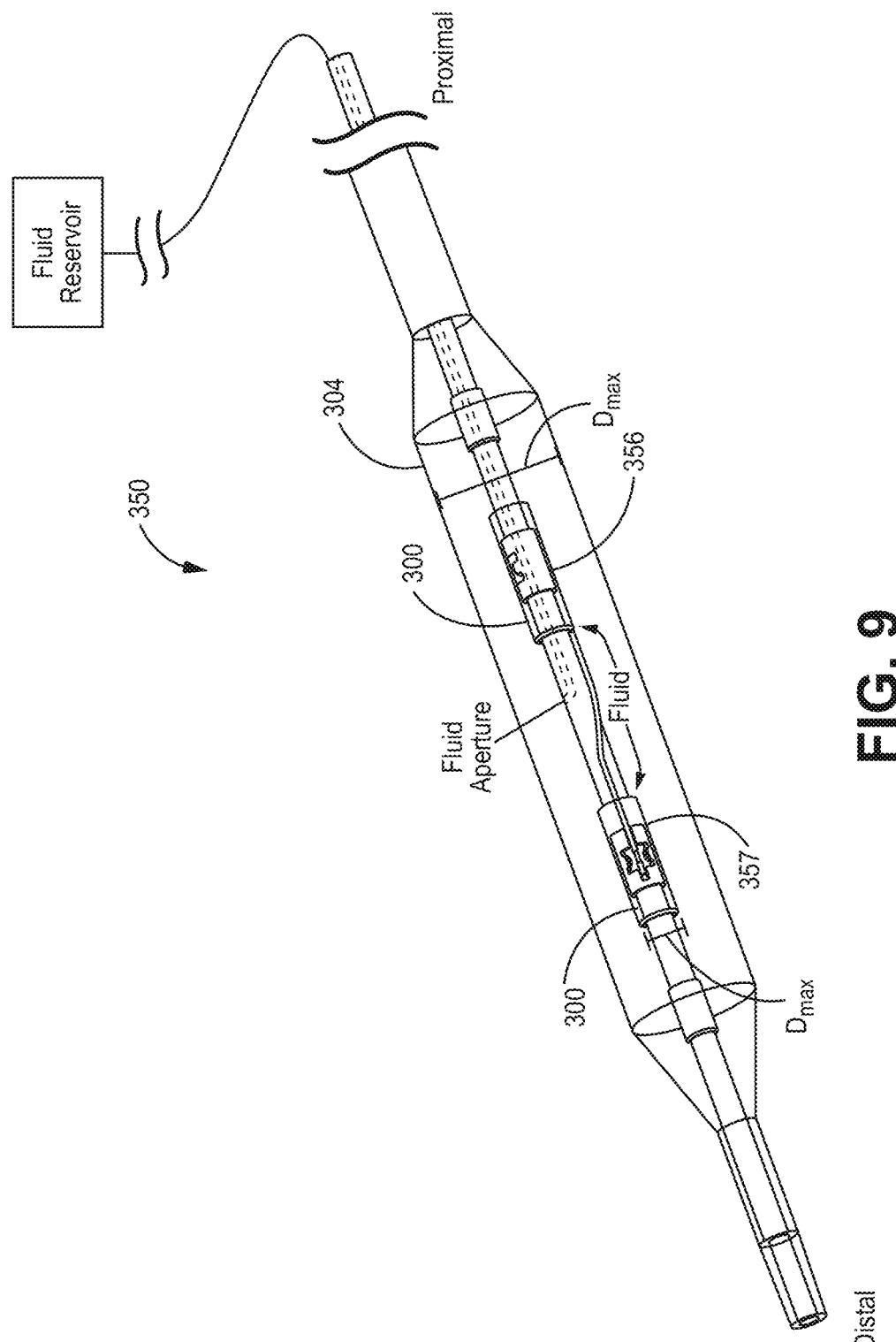
FIG. 9 illustrates a side cutaway view of one embodiment of the present invention.

Turning to FIG. 9, an exemplary intravascular lithotripsy device 350 is provided. Elongate catheter or member 302 is provided with an encapsulating balloon 304 disposed around catheter or member 302, defining a balloon interior capable of being inflated and/or deflated with a fluid F such as saline and, therefore, balloon 304 is sealed at both proximal and distal ends. Two flow and pressure wave generators 352, 353 comprising spaced-apart electrodes (the structure of which is discussed further infra) are disposed along an elongate catheter or member 352 in axially spaced-apart relation with each other. Flow and pressure wave generators 356 and 357 are connected electrically by one or more wire conductors W and with a voltage pulse generator (not shown). Each flow and pressure wave generator 356, 357 is surrounded by exemplary sleeve 300, which is described in various embodiments in relation to FIG. 10. As also described in FIG. 10, encapsulating balloon 304 surrounds the sleeves 300 and flow and pressure wave generators 356, 357. Fluid reservoir is shown in fluid communication with the interior of balloon 304 through fluid supply line and fluid aperture.

As noted above, if a partially collapsed balloon is used to confine the ionic current by providing a narrow fluid channel between the electrodes, it is preferred to constrain the balloon's motion or position to create a protective distance between the arc as it forms and the balloon.

Figure 10:
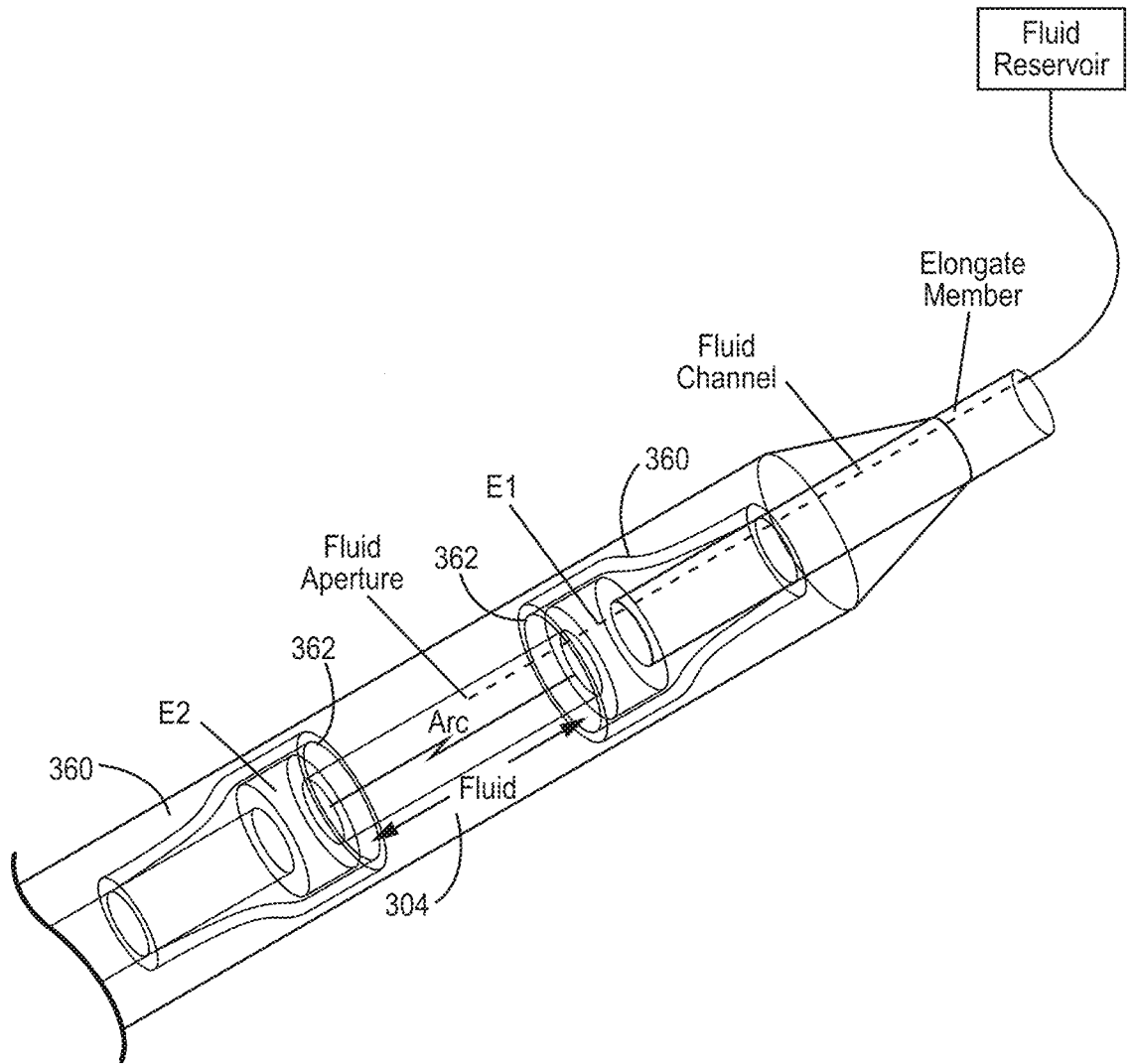
FIG. 10 illustrates a side cutaway view of one embodiment of the present invention.

FIG. 10 shows a partial sleeve 360 over each electrode E1, E2 and comprising a standoff 362 that limits the distance of the partially collapsed balloon's inflated configuration relative to each electrode E1, E2 and any resultant arc therebetween. Standoff 362 is shown as circular and disposed at an open end of each partial sleeve 360 and comprising a diameter that is larger than a diameter of the relevant electrode and wherein standoff 362 is positioned at a location that is axially spaced from the relevant electrode and into the gap between the two electrodes E1, E2. Standoff 362 may comprise any shape so long as the immediately preceding elements are satisfied. In this way, the standoff 362 and partial sleeve 360 create a barrier to a partially collapsed balloon relative to the electrodes E1, E2 and resultant arc. Partial sleeves 360 may be attached to the catheter or elongate member 302 and/or to insulated portions of its respective electrode E1, E2 to maintain the correct location.

Standoff 362 may also be used in certain embodiments described in connection with FIGS. 8 and 9 to ensure that the sleeve 300 is kept at a safe distance from the uninsulated electrodes and an electrical arc generated therebetween. In these embodiment, standoff 362 may be connected to the interior of the sleeve 300 or connected to an outer surface of the elongate catheter or member 302. Partial sleeve 360 is surrounded by encapsulating inflatable balloon 304 the interior of which is in fluid communication with a fluid reservoir via a fluid supply line, fluid channel and aperture disposed through catheter or member 302 and within balloon's interior.

Figure 11:
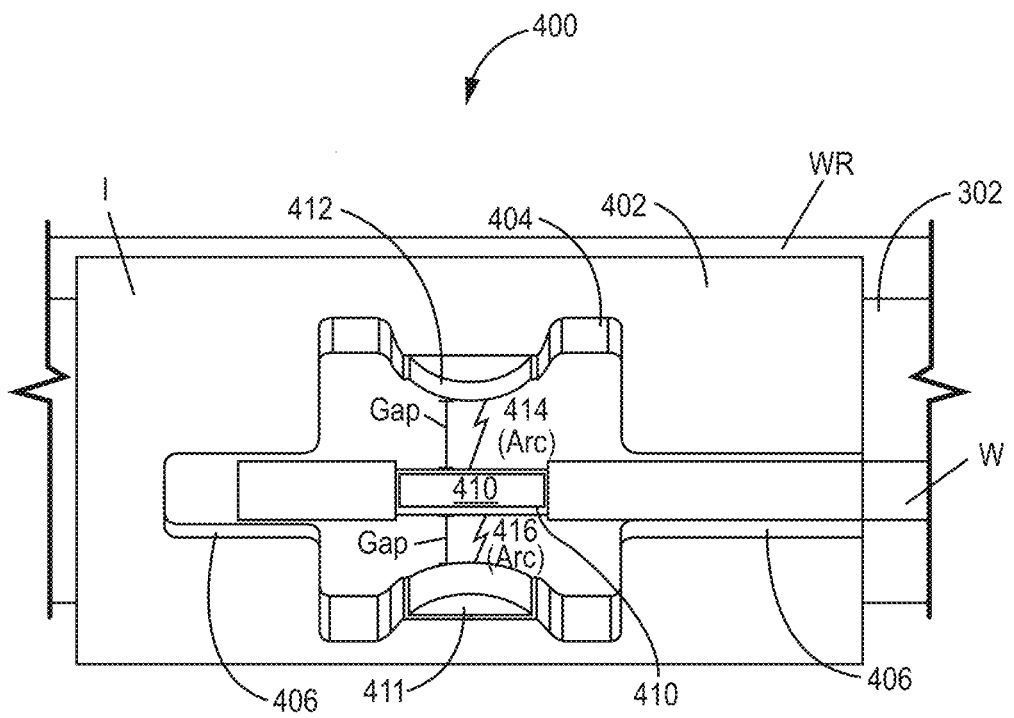
FIG. 11 illustrates a side cutaway view of one embodiment of the present invention.

FIG. 11 illustrates an embodiment of a flow and pressure wave generator 400. Flow and pressure wave generator 400 comprises a support or body portion 402 that is conductive but is primarily covered with an insulating material I. Support portion 402 may be attached to an elongated catheter or member 302. Support portion 402 comprises a cutout 404 and a channel 406 that is in communication with the cutout 404. Channel 406 allows a wire conductor W to extend along the support portion 402 and cutout 404 and provides a secured receiving structure for wire conductor W which is connected to a voltage pulse generator (not shown but described herein). A return conductor WR is also illustrated for connection to the voltage pulse generator to complete the circuit.

The wire conductor W is primarily covered with insulation and comprises a stripped portion devoid of insulation with exposed wire and that is disposed within the cutout 404 and that is proximal to a distal-most end of the stripped portion. The distal-most insulated portion of wire conductor W and a portion of insulated wire conductor proximal to stripped portion are both received within channel 406 on opposing sides of the cutout 404. Stripped portion defines a first electrode 410 of flow and pressure wave generator 400.

The cutout 404 embodiment shown comprises two arcuate or convex structures that are not covered by insulation on opposing sides of cutout 404. The two arcuate or convex structures each define a second electrode 411 and a third electrode 412 within flow and pressure wave generator 400. Electrode 410 is spaced radially from electrode 411 and also spaced radially on an opposing side from electrode 412, creating gaps therebetween as a result.

First, second and third electrodes 410, 411 and 412 are all preferably at the same radial position relative to an outer surface of the catheter member 302. Stated differently, the positions and/or locations of electrodes 410, 411 and 412 are preferably co-radial.

In other embodiments, one or more than one of electrodes 410, 411, 412 may be at a different radial position, i.e., not co-radial with the other electrodes. In these embodiments, one or more of the electrodes 410, 411, 412 may be disposed radially below or radially above the other electrode(s) 410, 411, 412.

As illustrated, flow and pressure wave generator 400 comprises two potential arc generating regions as illustrated by the arc 414 between electrode 410 and electrode 412, and the arc 416 between electrode 410 and electrode 411 that is present when the voltage pulse generator (not shown but as described above) provides sufficient voltage to the first electrode 410.

The arc generating region 414, 416 that is actuated may be influenced by the relative size or surface area of the arcuate electrodes 411, 412, and/or the relative size of the gaps between first electrode 410 and second and third electrodes 411, 412.

The surface areas of electrodes 410, 411 and 412 may be substantially equal. In other embodiments, one or more of electrodes 410, 411 and 412 may comprise unequal surface areas, e.g., one or two electrodes may have a greater surface area than the other electrodes.

Figure 12:
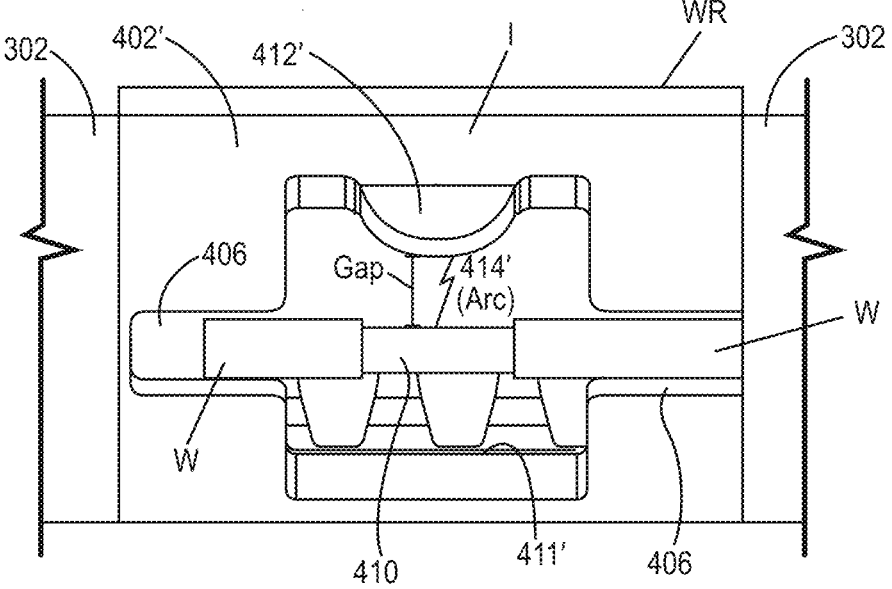
FIG. 12 illustrates a side cutaway view of one embodiment of the present invention.

As shown in FIG. 12, an alternative flow and pressure wave generator 400' is illustrated and which is a modified version of the flow and pressure wave generator of 400. Flow and pressure wave generator 400' comprises a support portion 402' that is conductive but is primarily covered with an insulating material I. Support portion 402' may be attached to an elongated catheter or member 302. Support portion 402' comprises a cutout 404' and a channel 406' that is in communication with the cutout 404'. Channel 406' allows a wire conductor W to extend along the support portion 402' and cutout 404' and provides a secured receiving structure for wire conductor W which is connected to a voltage pulse generator (not shown but described herein). A return conductor WR is also illustrated for connection to the voltage pulse generator to complete the circuit.

The wire conductor W is primarily covered with insulation and comprises a stripped portion devoid of insulation with exposed wire and that is disposed within the cutout 404 and that is proximal to a distal-most end of the stripped portion. The distal-most insulated portion of wire conductor W and a portion of insulated wire conductor proximal to stripped portion are both received within channel 406 on opposing sides of the cutout 404. Stripped portion defines a first electrode 410 of flow and pressure wave generator 400.

Figure 14:
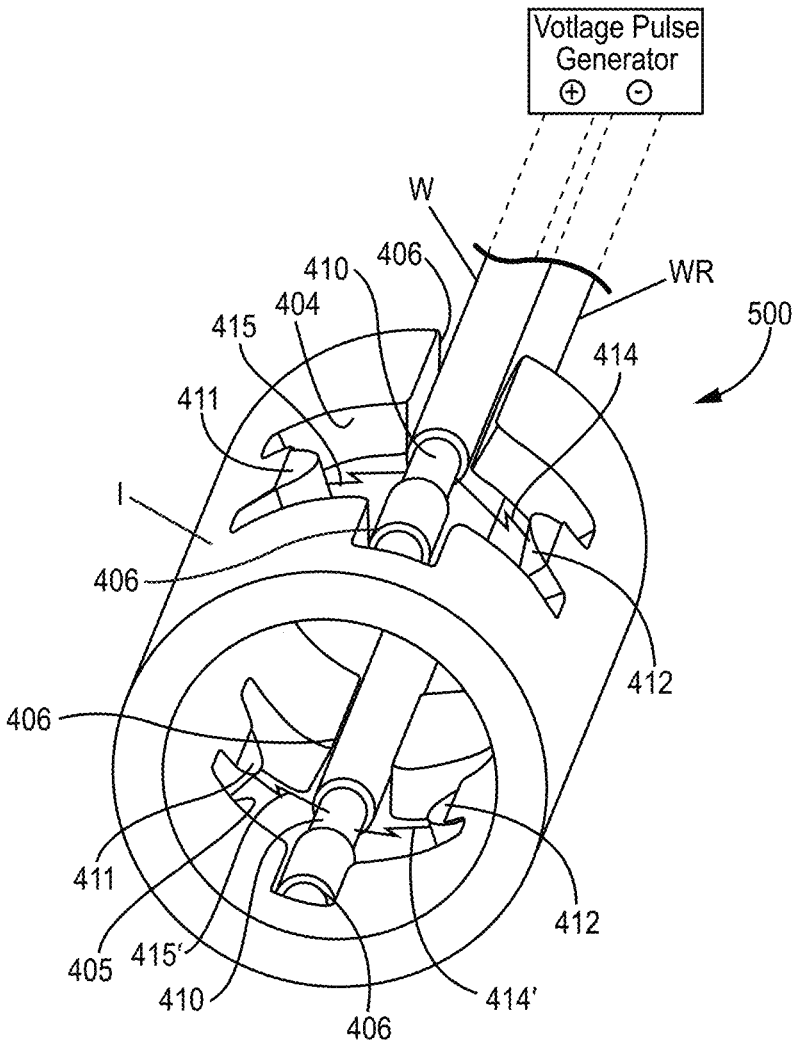
FIG. 14 illustrates a side perspective cutaway view of one embodiment of the present invention.

The cutout 404' shown in FIG. 14 comprises a single arcuate or convex structure that is not covered by insulation on one side of cutout 404'. The arcuate or convex structures defines a second electrode 412' spaced radially from electrode 410 and, creating a gap therebetween as a result.

First and second electrodes 410 and 412' are both preferably at the same radial position relative to an outer surface of the catheter member 302. Stated differently, the positions and/or locations of electrodes 410 and 412' are preferably co-radial.

In other embodiments, one electrode 410 and 412' may be at a different radial position than the other electrode, i.e., electrodes 410 and 412' may not be co-radial. In these embodiments, one or more of the electrodes 410 or 412' may be disposed radially below or radially above the other electrode(s) 410 or 412'

As illustrated, flow and pressure wave generator 400' may comprise one arc generating region as illustrated by the arc 414' between electrode 410 and electrode 412' that is present when the voltage pulse generator (not shown but as described above) provides sufficient voltage to the first electrode 410. Alternatively, a third electrode 411' may be provided along the flat region as shown and, therefore, this embodiment comprises two arc generating regions.

The surface areas of electrodes 410 and 412' may be substantially equal. In other embodiments, one or more of electrodes 410 and 412' may comprise unequal surface areas, e.g., one or two electrodes may have a greater surface area than the other electrodes.

In each of the embodiments of FIGS. 11 and 12, the arcuate or convex shape of electrodes defined by cutout 404, 404' is merely exemplary. Other shapes may be used and will now present themselves to the skilled artisan, all of which are within the scope of the present embodiment.

Figure 13:
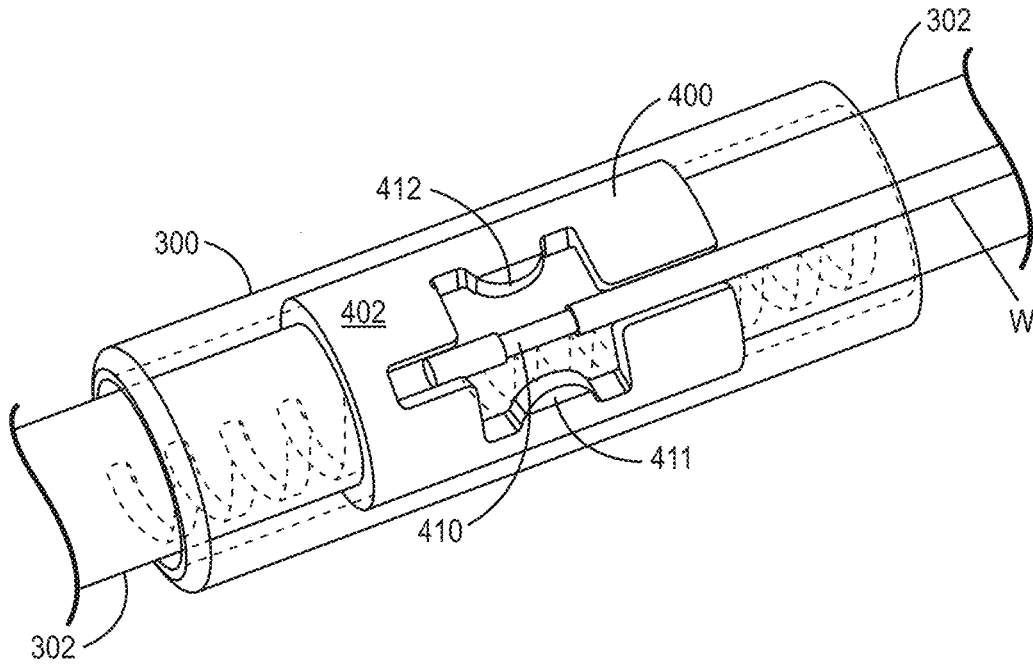
FIG. 13 illustrates a side perspective cutaway view of one embodiment of the present invention.

Turning now to FIG. 13, the exemplary flow and pressure wave generators 400, 400' of FIGS. 11 and 12 may be disposed within a fluid constraining sleeve 300 as described in connection with FIGS. 8 and 9 to obtain the described longer arcs and related benefits. An exemplary embodiment of this fluid-constraining arrangement is illustrated in FIG. 13 and does not require an encapsulating balloon in the case where, as described supra, the sleeve 300 is sealed to provide a water-tight enclosure for fluid. Sleeve 300 may be prefilled prior to insertion into the subject vessel or may be actively filled using a fluid channel through or along elongate catheter or member 302 and which is in fluid communication with a fluid reservoir (not shown but as well known in the art and described herein).

Accordingly, all flow and pressure wave generators may comprise embodiments with a sleeve 300 to constrain the fluid into a narrow channel between the electrode pairs as described herein and may or may not require an encapsulating balloon.

FIG. 14 illustrates an alternate embodiment of a flow and pressure wave generator 500, similar to that of flow and pressure wave generator 400, but with first and second cutouts 404, 405 formed or defined within support portion 402, wherein the cutouts 404, 405 are radially spaced from each other. Each of first and second cutouts 404, 405 may, as shown, comprise a first electrode 410 and second and third electrodes 411 and 412 as described in connection with FIG. 11. Each electrical conductor W, WR is connected with the voltage pulse generator as shown.

An exemplary current flow for the device of FIG. 14 is now provided. First, a voltage pulse of sufficient magnitude is send from voltage pulse generator through wire conductor W, creating an arc 414 between first electrode 410 and, e.g., third electrode 412. Initial arc 414 is created at the first cutout 404.

After initial arc 414 is created at the first cutout 404 between first and third electrodes 411, 412, current flows through conductive support member 402 to the second cutout 405 which has the same electrode configuration as cutout 404. Thus current flows from conductive support member 402 to the third electrode 412 (as shown), of the second cutout 405 and an arc 414' may be generated between the third electrode 412 and the first electrode 410 of the second cutout 405.

Alternatively, the current flow may be reversed around the support element 402 if the initial arc 415 is created at the first cutout 404 between first electrode 410 and the second electrode 411. In this case current will flow from the second electrode 411 through the conductive support portion 402 to the second electrode 411 of the second cutout 405. An arc 415' may be generated between the second electrode and the first electrode 411, 410 of the second cutout.

In both cases, once the second arc, either 414' or 415', is generated, the current flows to the low power or ground side of the voltage pulse generator via the return wire conductor WR as shown.

There are also channels 406 defined in the support portion 402 for receiving wire conductor W and the wire return conductor WR and associated stripped and exposed portion (forming a first electrode 410). In this manner, radially spaced-apart arcs and resultant pressure waves may be created within a single flow and pressure wave generator. These channels 406 aid in reducing crossing profile when present in any embodiment described herein.

FIG. 14 shows the first and second cutouts 404 and 405 at substantially opposite radial positions, i.e., spaced radially apart by approximately 180 degrees. This is merely exemplary and alternative radial spacings may be provided. In addition, more than one cutout, or two or more cutouts may be provided with associated electrode pairings such as electrodes 410, 411 and 412. Accordingly, two, three or more cutouts may be provided to produce, e.g., pressure waves from radial locations that are, e.g., 120 degrees spaced from each other around the support portion 402.

Figure 15A:
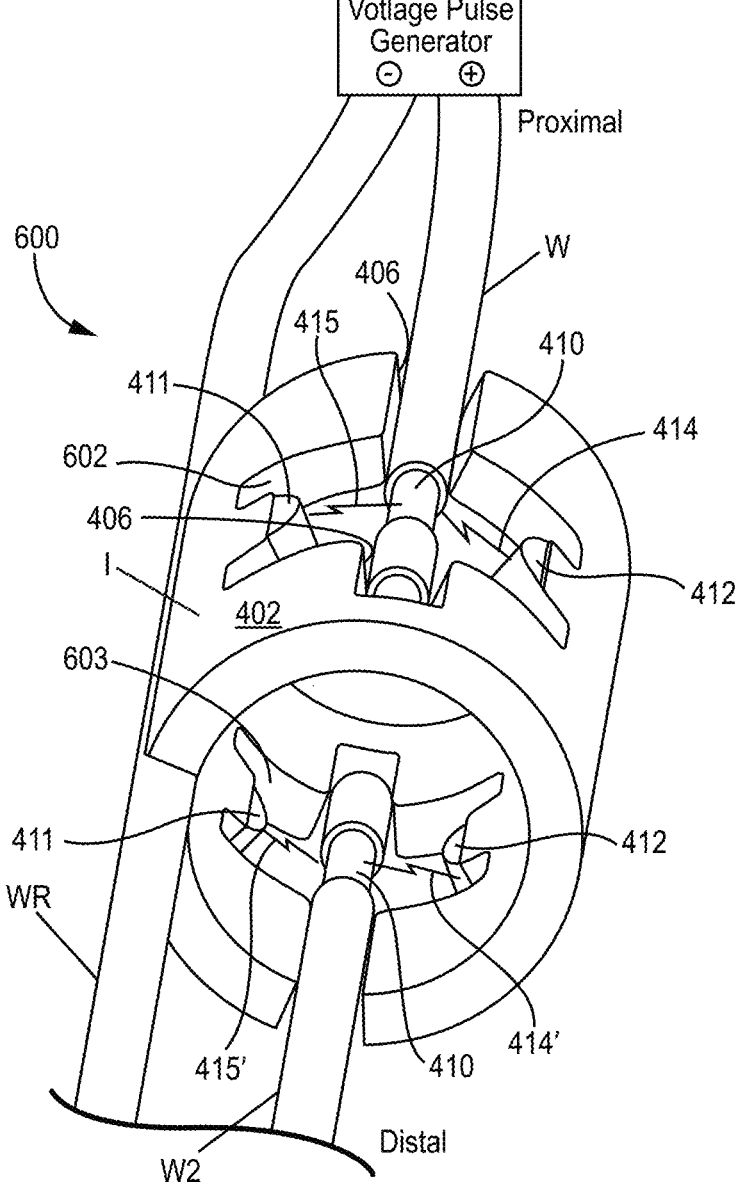
FIG. 15A illustrates a perspective cutaway view of one embodiment of the present invention.
Figure 15B:
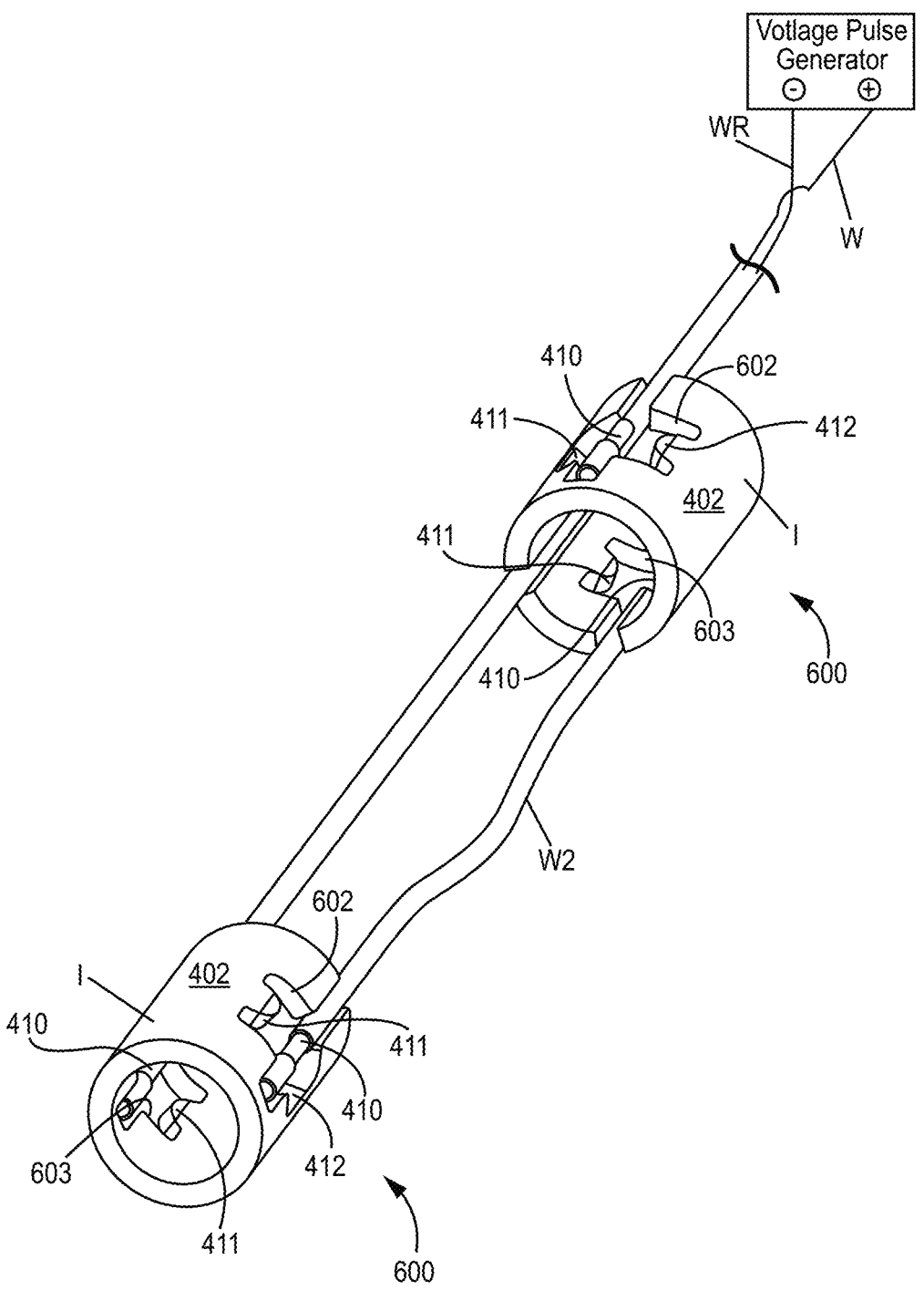
FIG. 15B a perspective cutaway view of one embodiment of the present invention.

Turning now to FIGS. 15A and 15B, an alternative flow and pressure wave generator 600 is provided. Here, the support portion 402 defines a first cutout 602 and a second cutout 603. As described above, the support portion 402 is conductive but insulated except for the two uninsulated portions defining a second electrode 411 and a third electrode 412 as those elements are also described supra. The insulated wire conductor W connected with the high power side of the voltage pulse generator extends through channel 106 disposed in, and in fluid communication with, the first cutout 602 and comprises a stripped portion that defines a first electrode 411 as described herein. First electrode 410 is spaced radially from, and on the same radial plane as, second and third electrodes 411, 412, creating gaps therebetween. The distal end of insulated wire conductor terminates at a distal portion of channel 405 in the first cutout 603.

The second cutout 603 comprises the same structure as that of first cutout 602, except that the wire conductor W comprises a second wire that is insulated and with an stripped exposed or uninsulated portion that defines a first electrode 410 of the second cutout 602, wherein the proximal insulated end of the second insulated wire conductor terminates at a proximal portion of channel 406 in the second cutout 603. Second cutout 603 also comprises portions that are uninsulated to define second and third electrodes 411, 412 and that extend toward the first electrode 410 of the second cutout 603. First electrode 410 of the second cutout 603 is spaced radially from, and is co-radial with, the second and third electrodes 411, 412 of the second cutout 603.

Flow and pressure wave generator 600 is thus configured to accommodate one or more of the support portions with cutouts and defined electrode pairs as described and shown in FIG. 17A. The second insulated wire conductor W2 may simply return to the low power side of the voltage pulse generator. Alternatively, second insulated wire conductor W2 may connect with another support portion with cutouts and defined electrode pairs in a series connection.

FIG. 15B illustrates such a series connection comprising a first proximal support portion 402 with first and second cutouts 602, 603 and the first, second and third electrodes 410, 411, 412 disposed and/or defined by or within each of the cutouts 602, 603, and a second distal support portion 402 with first and second cutouts 602, 603 and the first, second and third electrodes 410, 411, 412 disposed and/or defined by or within each of the cutouts 602, 603.

As best seen in FIG. 15A, for each of the support portions 402 connected in series, arcs generated between the first and second electrodes 410, 411 of the first cutouts 602 are designated as 415 and the arcs between first and third electrodes 410, 412 of the first cutouts 602 are designated as 414. And, for each of the support portions 402 connected in series, arcs generated between the first and second electrodes 410, 411 of the second cutouts 603 are designated as 415' and the arcs between first and third electrodes 410, 412 of the second cutouts 603 are designated as 414'.

Current flow in FIG. 15A is the same as that described in connection with FIG. 16. Current flow in FIG. 15B may proceed as follows: First, a voltage pulse of sufficient magnitude is send from voltage pulse generator through wire conductor W, creating an arc 414 between first electrode 410 and, e.g., the second electrode 411. Initial arc 415 is created at the first cutout 602 of the proximal or first support portion 402.

After initial arc 415 is created at the first cutout 602 between the first and second electrodes 410, 411, current flows through conductive support member 402 to the second cutout 603 which has the same electrode configuration as the first cutout 603. Thus current flows from conductive support member 402 to the second electrode 412 (as shown), of the second cutout 603 and an arc 415' may be generated between the second electrode 411 and the first electrode 410 of the second cutout 603 of the first or proximal support portion 402.

The first electrode 410 of second cutout 603 of the first or proximal support portion 402 comprises conductive insulated wire W2 which is operatively engaged with the first cutout 602 of the second or distal support portion 402. Current may thus flow from the first electrode 410 of the first cutout 602 to the third electrode 412 of the first cutout 602 and may generate an arc therebetween. Current may then flow through the second or distal support portion 402 to reach the second electrode 411 of the second cutout 603 of the distal support portion 402, and an arc may be generated between the second electrode and the first electrode 411 of the second cutout 603 and second or distal support portion 402. First electrode 411 of the second cutout 603 also serves as the return conductive wire WR, connecting to the voltage pulse generator to complete the circuit.

Each of the flow and pressure wave generators 600 are thus capable of generating one or more than one arc and resultant pressure wave for each sufficient voltage pulse. In the case described in FIG. 15B, the proximal and distal flow and pressure wave generator 600 will each generate two successive, and radially spaced apart, arcs and pressure waves for each sufficient voltage pulse. In addition, the pressure waves generated by the two flow and pressure wave generators will be axially or longitudinally spaced apart.

Figure 16:
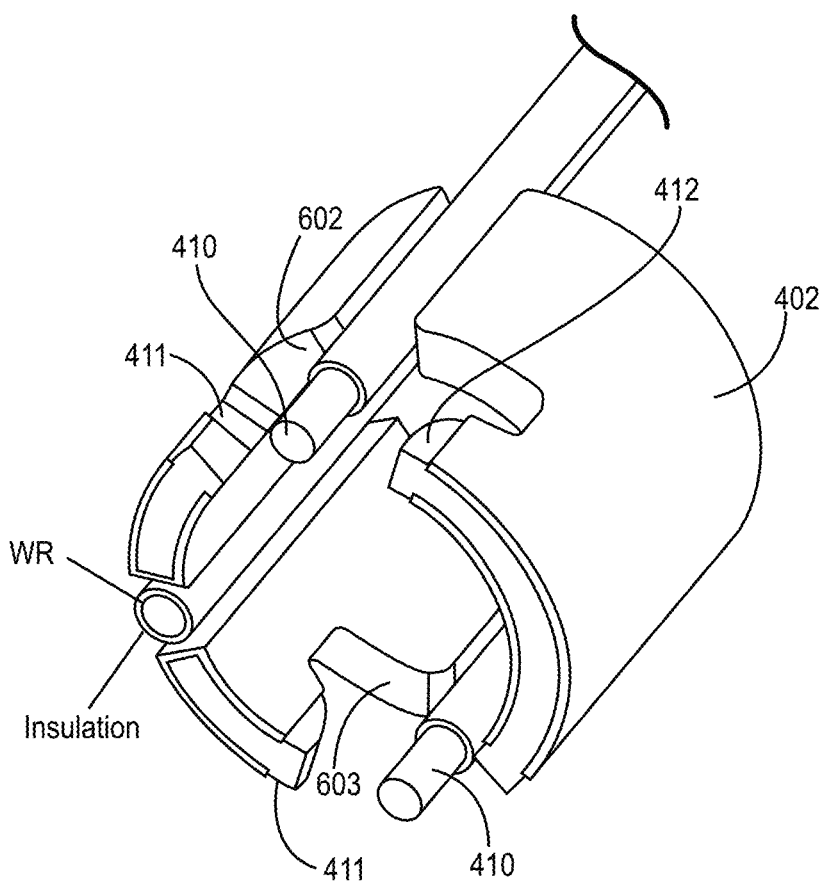
FIG. 16 illustrates a perspective cutaway view of one embodiment of the present invention.

FIG. 16 is a cross sectional view of the flow and pressure wave generator of FIGS. 15A and 15B and further illustrates the embodiment wherein the electrodes 410, 411 and 412 are all co-radially positioned around the support portion 402.

Figure 17:
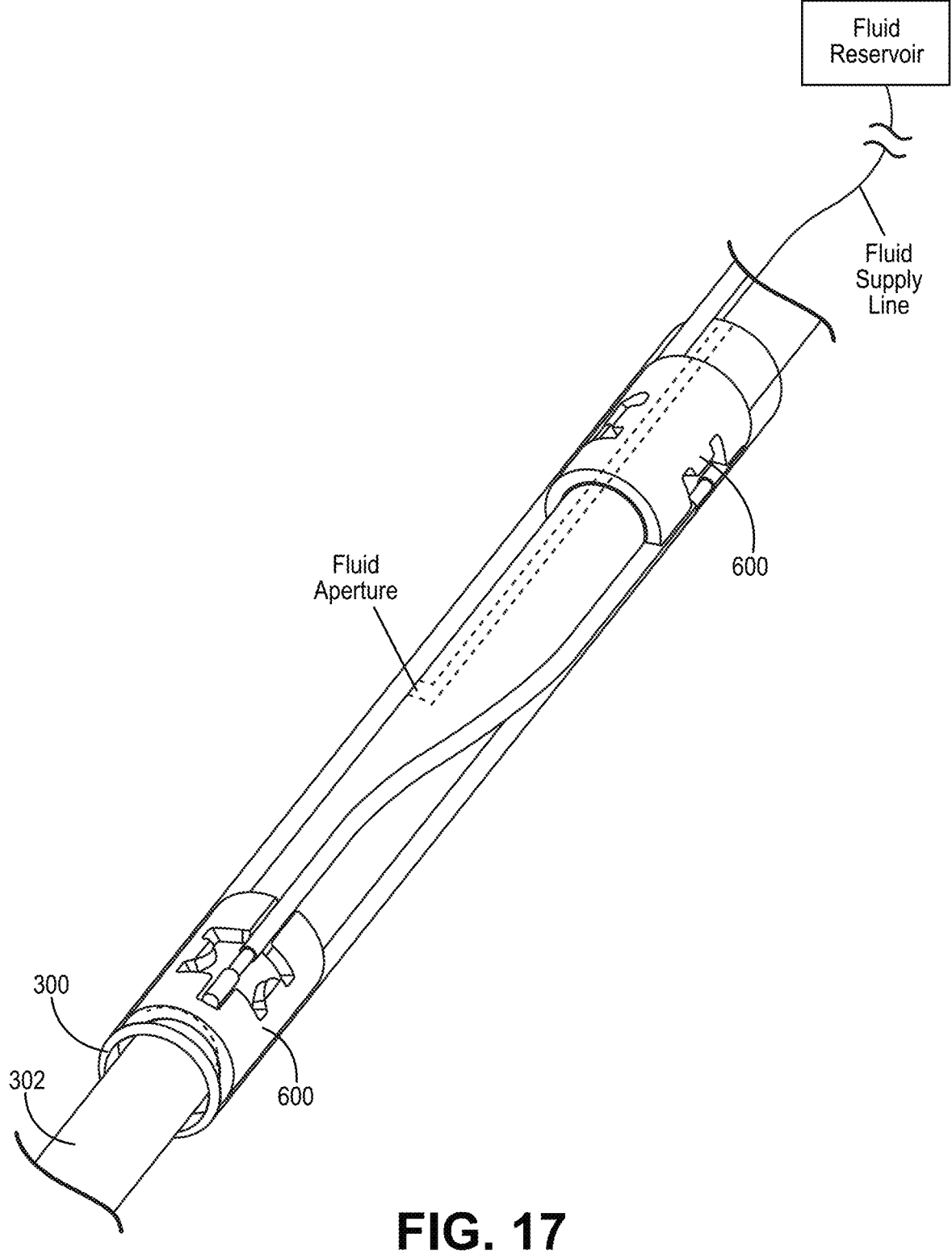
FIG. 17 illustrates a perspective cutaway view of one embodiment of the present invention.
Figure 18:
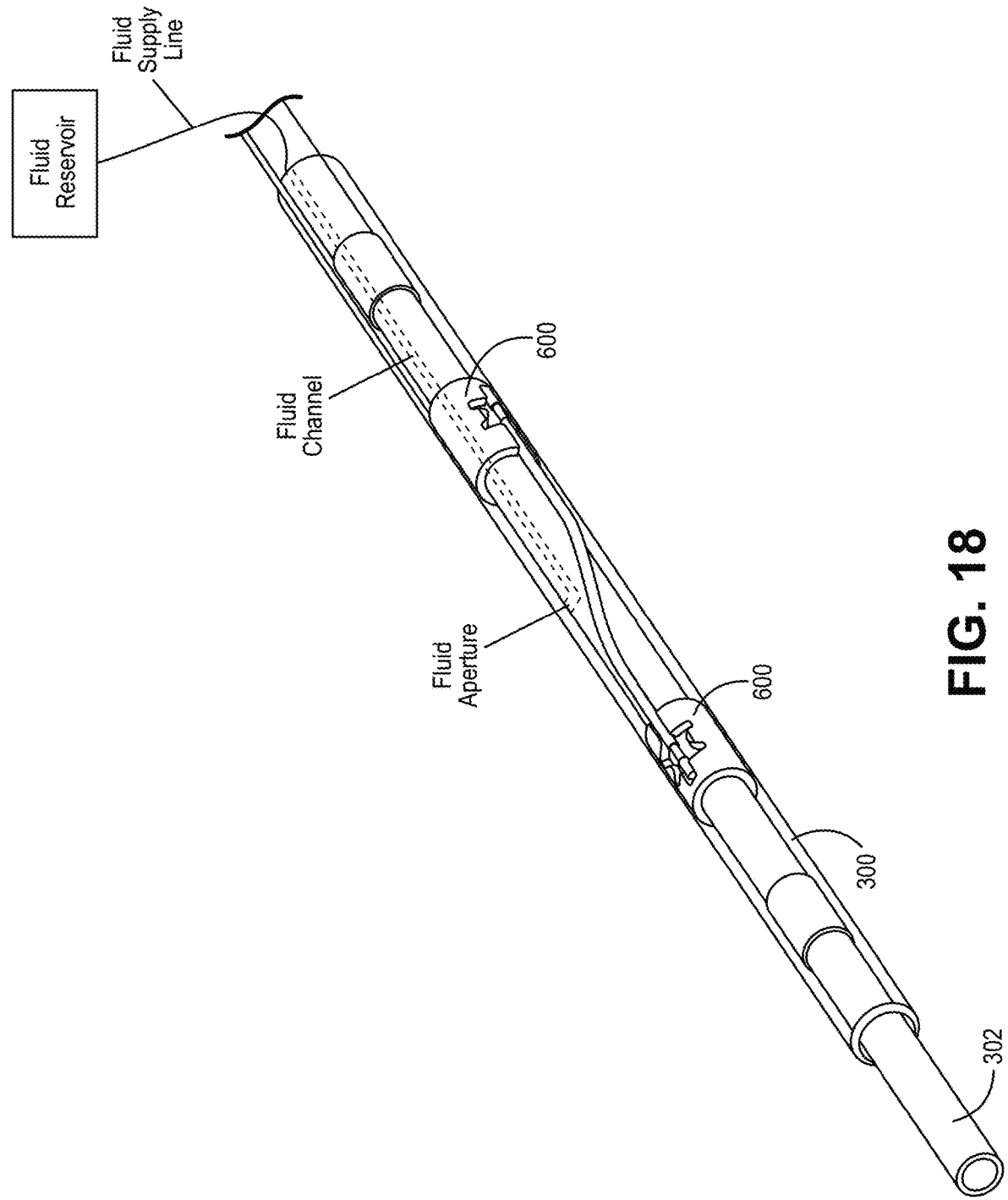
FIG. 18 illustrates a perspective cutaway view of one embodiment of the present invention.

FIGS. 17 and 18 illustrate the flow and pressure wave generator of FIGS. 15A and 15B wherein the individual flow and pressure wave generators 600 are encased within a single sleeve 300 as describe above. In alternate embodiments, a single sleeve 300 may be used to surround each of the individual flow and pressure wave generators 600. Sleeve(s) 300 may, as described above, be used with, or without, an encapsulating balloon and may be actively or passively inflated or deflated. As shown, the sleeve 300 interior is in fluid communication with fluid reservoir via a fluid supply line, a fluid channel and an aperture through catheter or member 302 disposed within interior of sleeve 300.

Figure 19:
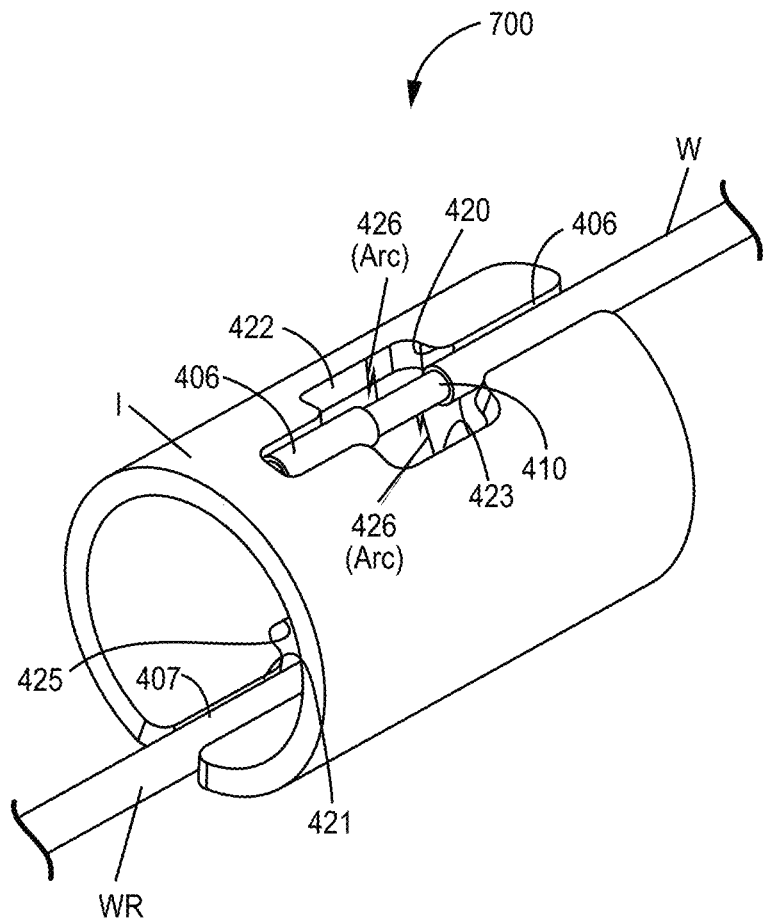
FIG. 19 illustrates a perspective cutaway view of one embodiment of the present invention.

FIG. 19 is another embodiment of a flow and pressure wave generator 700, and an embodiment similar to those described above, but the cutout portion does not comprise arcuate or convex structures that are not insulated to form electrodes. Instead at least a portion of the edges of the body of support portion 402 defining the cutout are not insulated. A single cutout, e.g., 420 as shown, or radially spaced apart cutouts 420, 421 as shown may be provided.

Flow and pressure wave generator 700 comprises a support portion 418 that is conductive but is primarily covered with an insulating material I. Support portion 418 may be attached to an elongated catheter or member (not shown but as described herein). Support portion 418 comprises a first cutout 420 and a second cutout 421 that are substantially identical in shape and a first channel 406 and a second channel 407 that is in communication with the cutout 404'. Channels 406 allows wire conductor W to extend along the support portion 418 and first cutout 420, and channel 407 allows wire return conductor WR to extend along the support portion 418 and second cutout 421. Each channel 406, 407 provides a secured receiving structure for wire conductor W, WR, respectively, each of which is connected to a voltage pulse generator (not shown but described herein).

The artisan will understand that WR may in fact return directly to the voltage pulse generator to complete the circuit, but will also readily understand that WR may lead to another flow and pressure wave generator 600 spaced away from the first flow and pressure wave generator, wherein the flow and pressure wave generators are arranged in series electrical connection, with a wire conductor return to the voltage pulse generator after a last flow and pressure wave generator 600 in a series of two or more flow and pressure wave generators 600, similar to the electrical configuration of FIG. 17B.

The wire conductors W, WR are, as described herein, each primarily covered with insulation and comprises a stripped portion devoid of insulation with exposed wire and that is disposed within the first cutout 420 (W) and second cutout 421 (WR), the exposed wire is disposed between insulated portions of wire conductors W, WR. Portions of insulated wire conductor W that are proximal and distal to stripped portion are both received within channel 406 defined along opposing sides of the cutout 420. Similarly, portions of insulated wire conductor WR that are proximal and distal to stripped portion are both received within channel 407 defined along opposing sides of the cutout 421. Stripped electrodes 425 each define a first electrode in the first cutout 420 and the second cutout 421.

The first cutout 420 comprises at least one uninsulated region along the edge E of the cutout 420. This at least one uninsulated region forms at least a second spaced-apart electrode 423 relative to the first electrode 410, with a gap therebetween. A second uninsulated region may be formed on an opposing side of cutout by removing insulation from the edge of the cutout 420, thereby defining a third spaced-apart electrode 425 relative to first electrode 410, with a gap therebetween.

The second cutout 421 may comprise the same structural features as that of the first cutout 420.

All electrodes 410, 423, 425 of flow and pressure wave generator 700 are preferably co-radial, but one or more of the electrodes may not be co-radial with the other electrodes.

Figure 20:
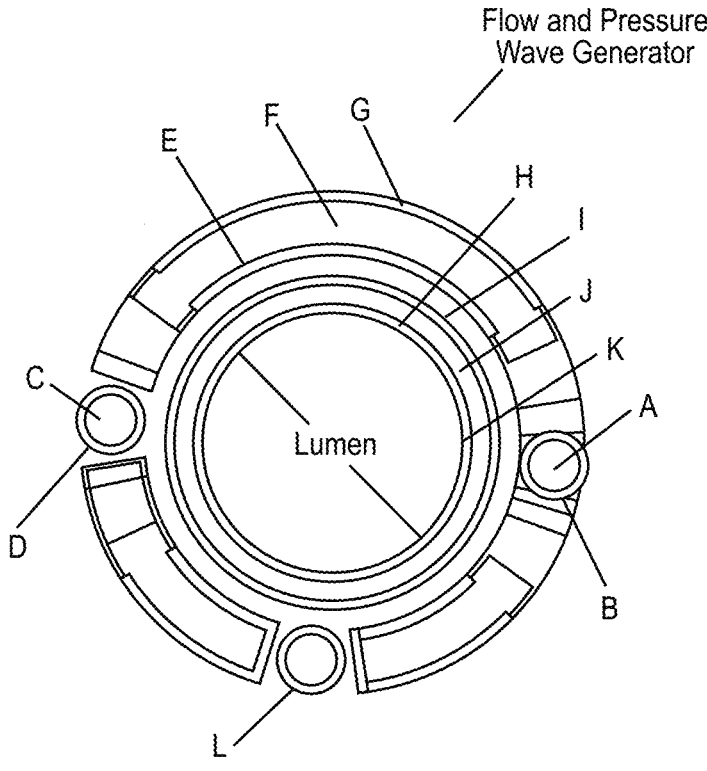
FIG. 20 illustrates a cross-sectional view of one embodiment of the present invention.
Figure 21:
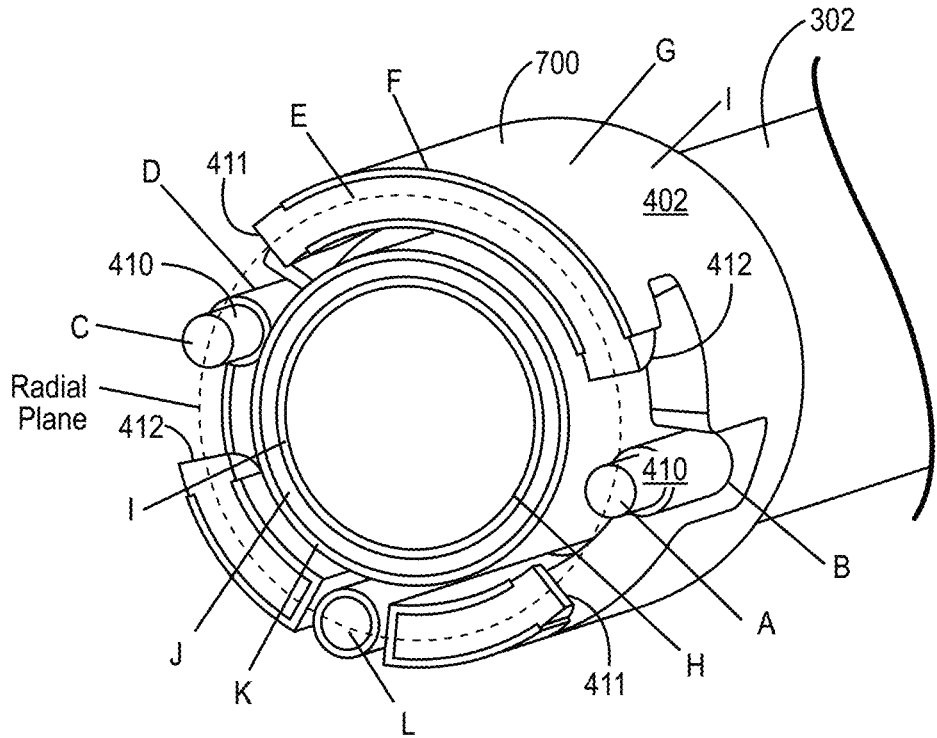
FIG. 21 illustrates a cross-sectional view of one embodiment of the present invention.

Turning now to FIGS. 20 and 21, a cross-section is taken through an exemplary flow and pressure wave generator to illustrate exemplary construction and layering of materials.

Members A and C are anode/cathode core elements.

B is an insulative layer on member A.

D is an insulative layer on member C.

As best seen in FIG. 21, members A and C each comprise the stripped portion defining first electrode 410 as described herein and is disposed in spaced-away relation with second electrode 411 and third electrode 412. Each of members A and C and related second and third electrodes 411, 412 are disposed in first and second cutouts as described herein.

E is an anode/cathode core element.

F is an insulative layer on member E that can resist high temperatures such as polyimide.

G is an anode/cathode core element, and is a non-continuous conductive support sleeve member.

H is a support member, e.g., elongate catheter or member 302, consisting of 3 elements: I, J and K.

IN is the inner layer of the support member consisting of an electrically insulative material with low friction to facilitate travel over a guidewire.

J is the middle layer of the support member consisting of a mechanical support feature such as a braid or coil or similar.

K is the outer layer of the support member consisting of an electrically insulative material that can resist high temperatures such as polyimide.

L is a ground wire that extend to another non-continuous conductive support sleeve member and is not attached to member G.

Lumen is defined as illustrated for receipt of elongate catheter or member 302 as described herein.

Generally, embodiments of the present invention comprise methods and devices for generating flow and pressure waves, traveling at subsonic and sonic and/or supersonic, for disrupting or cracking calcified regions within a blood vessel, though the disruptive effects of the generated flow and pressure waves may extend to partially or non-calcified occluding material. More specifically, with reference to FIGS. 22-33, an exemplary and alternative embodiment 1100 comprises an elongated member or carrier 1102 such as a catheter with a known inflatable angioplasty balloon 1104 mounted on or near the distal end 1103 of the elongated carrier 1102 which in certain embodiments may comprise a laser cut polyimide tube. The distal end 1105 of the balloon 1104 may be sealed against or around the elongated carrier 1102 to create a watertight barrier and further comprises a fluid inflating/deflating channel 1106 in fluid communication with the interior of the balloon 1104 and in fluid communication with a fluid-containing reservoir (not shown) that is located external to the patient, and as is well-known in the art, for inflating the balloon 1104 with fluid F and deflating balloon 1104. A guide wire lumen (not shown but as is well-known in the art) configured to allow translation of a guide wire extends through the elongated carrier and distally out therefrom, an arrangement also well known to the skilled artisan.

It is to be understood that the various embodiments of the present invention are also effective within a fluid-filled environment, e.g., a bodily cavity and/or a blood vessel, i.e., without requiring a fluid-filled balloon. The various embodiments are described in relation to a fluid-filled balloon, but will also apply to an elongated catheter disposed within a fluid-filled environment wherein the flow and pressure wave generators described infra may be disposed along the elongated carrier within the fluid-filled environment and with or without sleeve 300. All such embodiments are within the scope of the present invention.

Therefore, at least one flow and pressure wave generator 1200 is provided, wherein each flow and pressure wave generator comprises two conductive features spaced apart by a gap defined therebetween. In some embodiments, two flow and pressure wave generators 1200, 1200' may be provided. In still other embodiments, more than one flow and pressure wave generator, i.e., two or more, may be provided.

If a single flow and pressure wave generator 1200 is provided, it may be substantially axially centered within the balloon 1104. In other embodiments, the single flow and pressure wave generator 1200 may be biased to the proximal or to the distal end of the balloon's interior.

When two or more flow and pressure wave generators are provided, 1200, 1200', adjacent flow and pressure wave generators, e.g., 1200, 1200', may be spaced axially apart from each other, wherein the resultant gaps defined by each flow and pressure wave generator 1200, 1200', are axially spaced apart from each other. In cases wherein three or more flow and pressure wave generators are provided, the resultant gap between adjacent subsonic pressure wave generators may be substantially equal, or one or more spark gaps may be longer or shorter than for other flow and pressure wave generators.

As described supra, a fluid constraining sleeve 1300 may be provided around one or more of the flow and pressure wave generators 1200, 1200' to aid in lengthening the gap between electrodes in a pair of electrodes.

With continued reference to FIGS. 22-33, a first, proximal, flow and pressure wave generator 1200 may comprise a proximal electrode 1201 and an axially spaced apart distal electrode 1202, defining a gap therebetween. Next, a second, more distal, flow and pressure wave generator 1200' may comprise a proximal ring electrode 1203 and an axially spaced apart distal ring electrode 1204, also defining a gap therebetween. As will be discussed further, the distal ring electrode 1202 of flow and pressure wave generator 1200 and the proximal ring electrode 1203 of flow and pressure wave generator 200' may be in electrical communication with each other to enable current to flow therebetween.

For all embodiments described herein, initially the saline filling the balloon acts as a resistive heater, and the applied voltage generates an ionic current that ohmically heats the saline. The saline heats up the fastest where the current crowding is the strongest. In the cases shown, the current crowding is strongest at the electrodes. It is possible, as discussed supra, to baffle the saline with insulating features so that the highest current crowding appears at intermediate positions between the electrodes; this special case is of interest both for reducing electrode blast damage and for constraining the volume of saline participating in ionic conduction (so there is less waste heat).

As will be understood by skilled artisan, the electrical communication may comprise initial electrical connection with a proximal-most electrode to the "high" power side of a voltage pulse generator, or a distal-most electrode to the high power side of the voltage pulse generator, or an intermediate electrode disposed between proximal and distal electrodes may be connected with the high power side of the voltage pulse generator. First, e.g., with a proximal electrode electrically coupled or in electrical communication with a "high" power side of a circuit and power source connected therein, and a distal electrode electrically coupled or in electrical communication with a "ground" or "return" side of the circuit and power source connected therein. Second, a distal electrode may be electrically coupled or in electrical communication with a "high" power side of a circuit and power source while a proximal electrode may be electrically coupled or in electrical communication with a ground or return side of the circuit and power source. Similarly, an intermediately positioned electrode may be electrically coupled or in electrical communication with a "high" power side of a circuit and power source while another electrode is electrically coupled or in electrical communication with a ground or return side of the circuit and power source. In each case, once the flow and pressure wave generator(s) is/are actuated and arc(s) are generated, the circuit is completed and current will flow through the circuit.

At least one of the flow and pressure wave generators, e.g., 1200 may be in direct electrical connection and communication with an externally located power source or power source 1300, wherein the power source may be configured to provide voltage pulses of a predetermined magnitude and pulse length along an electrical conductor to a proximal ring electrode of a proximal-most flow and pressure wave generator 200. Alternatively, the voltage pulses may be delivered without a predetermined magnitude or pulse length. In some embodiments, a collapsing field in an inductor, e.g., a well-known car ignition mechanism), or decaying voltage from a capacitor may be employed, neither of which comprise or require a predetermined voltage or pulse length; instead, they comprise a predetermined stored energy level that will be expended during the pulse in the saline, the cables, the resulting Townsend discharge, in EMI, and in flow.

Each flow and pressure wave generator 1200, 1200', etc., comprises a pair of spaced-apart electrodes. Electrode pairs 1201, 1202 and 1203, 1204 are shown in axially spaced-apart disposition and mounted around the elongated carrier 1102, e.g., by crimping or other attachment means and are immersed within the fluid F in the inflated balloon 1104. Accordingly, gaps are defined between electrode pair 1201 and 1202, and between electrode pair 1203 and 1204, wherein electrodes 1202 and 1203 are in operative electrical communication or connection. As discussed above, the gaps may be of equivalent length or may comprise differing lengths. In some embodiments, a single flow and pressure wave generator 1200 may be provided, while in other embodiments, more than one flow and pressure wave generator 1200, 1200', etc., may be provided.

Thus, in some embodiments, first and proximal-most electrode 1201 may be electrically coupled or in electrical communication or connection, via an electrical conductor, with a power source, e.g., the power source 1300, that is configured for supplying voltage pulses to the electrode pair(s) comprising the flow and pressure wave generator(s) 1200. The distal-most electrode, e.g., 1204, may also be electrically coupled or in electrical communication or connection, via a second electrical conductor, with the power source, 1300. The electrodes 1201, 1202, 1203, 1204, including body B and/or support portion may comprise ring-shapes or partial ring-shapes as illustrated. Other forms or shapes of electrodes or support portions thereof will present themselves to the artisan and are within the scope of the presently described inventions.

The fluid F within the inflated balloon 1104 is ionically conductive, e.g., saline. Saline is prescribed, as opposed to other ionically conductive fluids, to mitigate side effects should a balloon rupture. As described supra, application of a few volts between the spaced-apart ring electrodes in each electrode pair 1201, 1202 and 1203, 1204 comprising the flow and pressure wave generators 200 and 200' will initiate ionic current flow in the saline. The shorted paths between the electrodes will experience relatively lower resistance to ionic current flow; since the local dissipated power varies as the voltage difference squared divided by the resistance, these shorted paths will heat up the fastest. Depending on the electrode geometry, electric field lines connecting the electrodes can pass through minimally just the small amount of saline in the gap between the electrodes, and maximally all of the saline in the balloon. As this saline-heating phase has little or no treatment benefit, it is preferential to minimize the volume of saline experiencing the electric fields from the voltage applied to the electrodes.

If the voltage applied is sufficient to locally heat the liquid saline above approximately 350 deg C., the saline will promptly boil. For the exemplary flow and pressure wave generators 200, 200' shown in FIG. 22, the current crowding at the electrodes dictates that boiling will be initiated adjacent to the electrodes. The boiling phase transition causes the liquid saline involved to expand to about 1000× its fluid volume (less if the balloon is pressurized, more if the balloon is at less than 1 atmosphere). This initiates the flow generation, generally increasing the volume occupied by the balloon as the steam expands.

If the two electrodes of an exemplary flow and pressure wave generator described herein become connected by a contiguous gaseous path, a different phenomenon appears. The contiguous gas path can be formed by the expansion of one boiling event, or by merging bubble fronts from two or more boiling events. The contiguous gaseous path allows a Townsend discharge to take place. More precisely, if the pressure in the gas, the gap, the gas chemistry, and the voltage satisfy Paschen's law, then electrons and ions in the gas experience enough acceleration in the electric field during their mean free paths between collisions to generate additional ions and electrons in those collisions, creating an ion avalanche capable of carrying very high currents. The initial ion channel connecting the electrodes is termed the leader; once formed, it grows quickly radially as the ion and electron density (and temperature) increase.

Prior to the Townsend discharge, the electrical resistance between the electrodes of a flow and pressure wave generator is dominated by the ionic conductivity of the saline, and generally is in the range of 50 ohm to 50 Kohm. Once the leader has formed and has expanded radially has much as the voltage generator can support, the resistance between the electrodes drops to substantially less than an ohm; the current from the power source becomes limited predominantly by the cabling between the power source and the flow and pressure wave generator.

Thus, upon application of sufficient voltage generated by the power source 1300 to the proximal-most electrode, e.g., 1201, via a conductor in electrical connection or communication between the power source 1300 and electrode 1201, may cause current to flow between electrode 201 and electrode 1202, potentially resulting in a Townsend discharge across the defined gap between electrodes 1201, 1202. A return conductor in operative electrical connection or communication with electrode 1202 completes the circuit back to the power source 1300. In this manner, the circuit resistance may change significantly during the discharge between electrodes 1201, 1202 in an embodiment having a single electrode pair comprising a single flow and pressure wave generator 1200.

Figure 22:
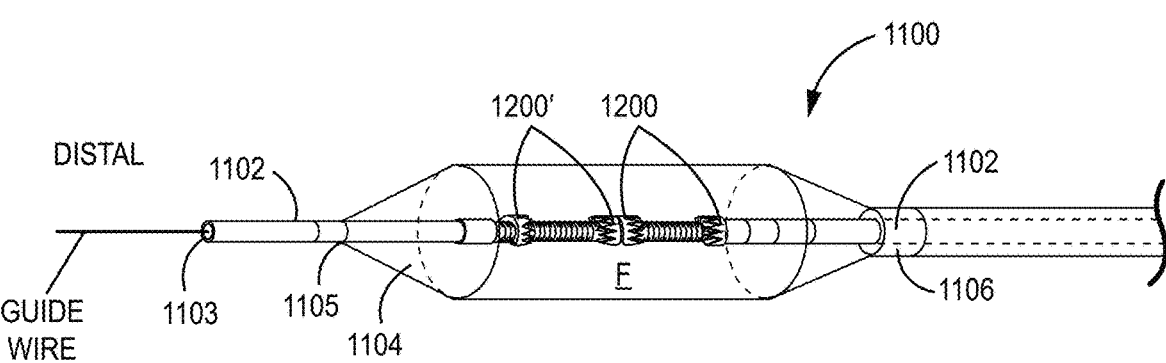
FIG. 22 illustrates a perspective cutaway view of one embodiment of the present invention.

FIG. 22 illustrates the fluid-filled balloon 1104 in an inflated state wherein a conductive fluid F such as saline fills the balloon's interior space, with the spaced-apart electrodes 1201, 1202 and 1203, 1204 disposed therein and immersed in fluid F. Electrodes 1201, 1202, 1203 and 1204 are arranged generally symmetrically around the elongated carrier 102 and generally symmetrically along a center line of the inflated balloon 1104.

Figures 26, 27:
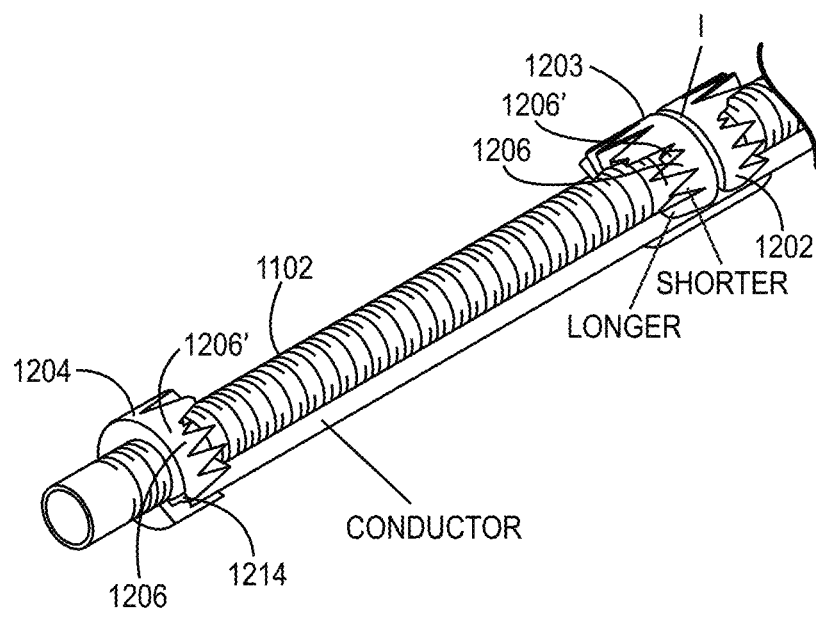
FIG. 26 illustrates a perspective cutaway view of one embodiment of the present invention.
FIG. 27 illustrates a perspective cutaway view of one embodiment of the present invention.
Figure 28:
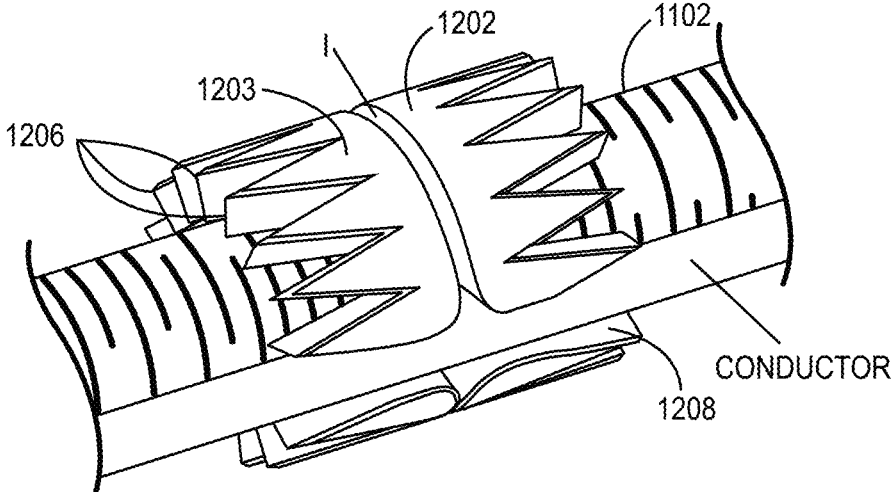
FIG. 28 illustrates a perspective cutaway view of one embodiment of the present invention.

However, in a preferred embodiment, as shown in at least FIGS. 27 and 28, a channel or groove 1208 may be defined through or along the electrodes along a longitudinal plane to allow the insulated conductor(s) to be disposed at least partially therein so as to reduce crossing profile of the system. Thus, the channel 1208 may be formed by carving out a portion of the electrode wherein the electrode does extend circumferentially around the elongated carrier 1102. Alternatively, as illustrated in at least FIG. 28B, channel or groove 1208 may comprise a void or space between two spaced-apart ends of the electrode, wherein the electrode extends partially circumferentially around the elongated carrier 1102 and wherein the conductor may extend along the outer surface of elongated carrier 1102. With the exception of the interruption of the channel 208 in the ring electrode(s), the preferred structure is symmetrical as discussed above, though asymmetrical electrode(s) may also be employed.

FIGS. 22-33 illustrate possible arrangements and embodiments of the spaced-apart electrodes that form each electrode pair as well as the conductive wire connections thereto.

FIG. 223 thus illustrates the elongated carrier 1102, which may comprise a laser cut tube and may comprise polyimide or other material. Two exemplary flow and pressure wave generators 1200, 1200' are shown in axially spaced-apart relation relative to each other along the elongated carrier 1102. Each flow and pressure wave generator, e.g., 1200, 1200', comprise spaced-apart exemplary ring electrodes, respectively 1201, 1202 and 1203, 1204, each defining a gap between the relevant spaced-apart electrodes of a predetermined length, that is the spacing distance between the spaced-apart electrodes 1201 to 1202, and 1203 to 1204. The distal electrode, e.g., 1202, of the proximal flow and pressure wave generator 1200 and the proximal electrode 1203 of the distal flow and pressure wave generator 1200' are shown in relatively close disposition forming an interface I therebetween, the interface defining and comprising an electrical communication between the two electrodes defining the interface I.

The various forms and types of electrical connections between these intermediary ring electrodes 1202, 1203 defining an interface I are described further herein, but generally comprise a physical or operative electrical connection between surfaces of the two intermediary electrodes that may comprise a touching relationship, a weld bead, or a jumper wire or other conductive interconnection element, or mechanism, between the two intermediary ring electrodes 1202, 1203, or other conducting connection. The skilled artisan will readily recognize alternative mechanisms for creating the required electrical connection between the intermediary electrodes, 1202, 1203 i.e., between adjacent flow and pressure wave generators 1200, 1200', each of which is within the scope of the present invention. In this arrangement, the two or more flow and pressure wave generators 1200, 1200', etc., may be electrically connected in what effectively becomes a series circuit. The number of flow and pressure wave generators used in certain embodiments may be one, or two, or more than two.

Figure 25:
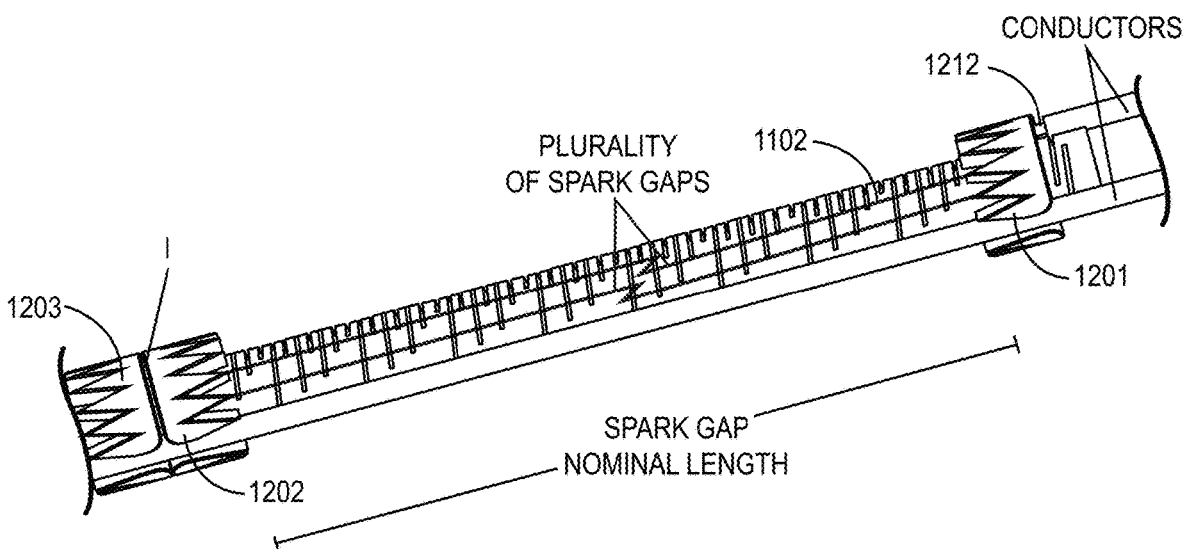
FIG. 25 illustrates a side cutaway view of one embodiment of the present invention.

As discussed further herein, the electrodes described herein are exemplary, other electrodes shapes and structures are within the scope of the present invention. In certain embodiments, and as discussed further infra, at least one of the electrodes in an electrode pair comprising a flow and pressure wave generator may comprise a plurality of aligned points or extensions that extend toward the gap defined between the electrode pair. This is best illustrated by FIG. 25 wherein each electrode 1201 and 1202 comprise a plurality of points or extensions 1201 that are aligned radially with each other and define a plurality of individual gaps capable of generating arcs or sparks therebetween. As illustrated, these plurality of individual gaps are distributed around at least part of the circumference of the elongated member 1102.

Still further, certain embodiments may comprise a plurality of electrode pairs, at least one electrode pair comprising a proximal-most electrode in wired, or other, electrical communication with the power source 1300. In some embodiments, more than one electrode pair in the plurality may comprise a proximal-most electrode in wired, or other, electrical communication with the power source 1300, wherein at least one of the electrode pairs in the plurality may be separately and individually energized by the power source 1300. Thus, certain embodiments may comprise a parallel connection arrangement of at least some electrode pairs, or may comprise a combination of series connected sets of electrode pairs with one or more sets of electrode pairs comprising a parallel connection back to power source.

The skilled artisan will recognize that the reference to an operative electrical connection or communication with a proximal-most electrode of an electrode pair and the power source 1300 is merely illustrative. It is within the scope of the present invention to simply switch the operative electrical connection to be between a distal-most electrode of an electrode pair and the power source 1300.

In certain configurations, individual flow and pressure wave generators, 1200, 1200' may be controlled regarding the magnitude of voltage applied, the magnitude of current flow resulting in an arc between the electrodes comprising the flow and pressure wave generators, the time duration of current flow and arcing between the electrodes comprising the flow and pressure wave generators, the current in the primary of a discharge inductor, the charge in a discharge capacitor and/or the initiation time of the current flow or arcing between the electrodes comprising the flow and pressure wave generators.

Catheter and Electrodes

As provided above, an exemplary laser-etched polyimide tube 1102 as shown in FIGS. 24-27 may be provided with ring electrodes 1201, 1202 and 1203, 1204, wherein the electrodes are attached to the tube 1102, with insulated wires connecting the electrodes back to the external voltage pulse generator/power supply 1300.

In the two-wire configuration shown, the gap between the electrodes may be decreased by opening the distance between the two adjacent center, intermediary electrodes (1202 and 1203) in the electrode pairs while electrically connecting them with an additional wire.

FIGS. 30A and 30B provides an exemplary ring electrode E having a body portion B defining a central aperture A configured to securely engage the catheter 1102, channel 208, a front surface defining a plurality of points 1206 and a flat rear surface. FIG. 30A illustrates an uncorroded set of electrode points or extensions 1206. FIG. 230B provides an electrode point or extension 1206' that illustrates exemplary effects of corrosion on one of the points caused by arcing between adjacent ring electrodes. One or more of the remaining points 1206 may engage to generate the arc across the gap between electrodes in an electrode pair if the corrosion renders the electrode point or extension 1206' less apt to participate in ionization and arcing.

The electrode points or extensions 1206 may comprise a substantially triangular profile as illustrated, but this is merely exemplary. Consequently, other profiles are also contemplated. The underlying functionality of the electrode points 1206 is to enable arcs to initiate from different locations on the electrode. Therefore, any shape that extends away from the main body B of the electrode generally toward the distal-most electrode in an electrode pair, and generally toward the spark gap defined therebetween, comprising a flow and pressure wave generator will be sufficient. The tip regions of adjacent ones of the plurality of electrode points are in certain embodiments, spaced radially apart from each other.

Multiple points 1206 on the exemplary electrodes facing the spark gap region defined between electrodes, e.g., 1201, 1202, allow electrical breakdown streamers to initiate from several different locations or points 1206 disposed on and/or around the electrode body B, so viable electrode points or extensions 1206 remain when some are corroded by the arc. This extends the effectiveness and life of the electrode and reduce the voltage required to initiate an arc. In addition, the path of the arc may comprise debris, so originating arcs from different locations, i.e., points 1206, on the electrode(s) body B aids in reducing the debris, making it less likely that a short is formed. In this way, the environment surrounding the electrodes and within the spark gap therebetween is maintained as uniformly as possible throughout the treatment session comprising a plurality of pulses.

Figure 24:
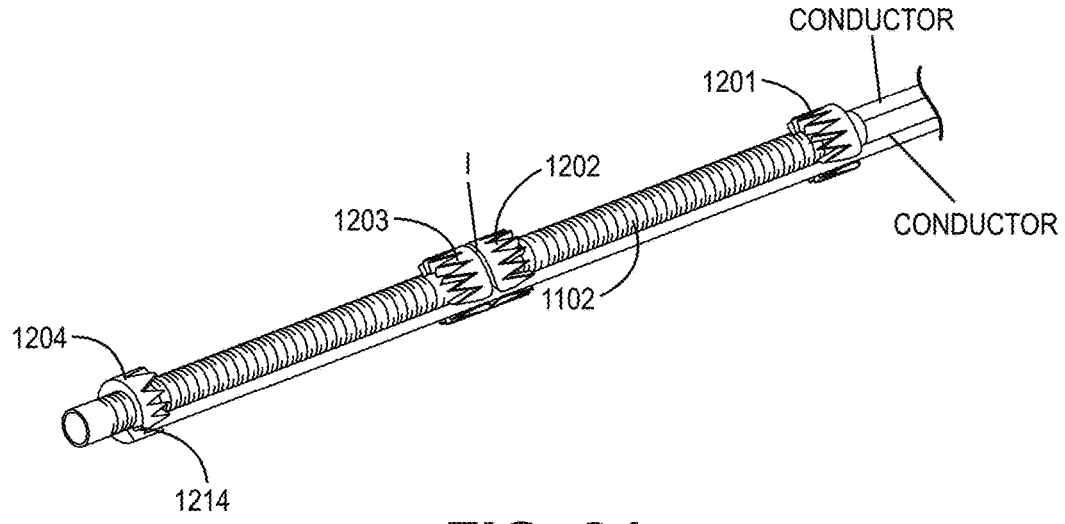
FIG. 24 illustrates a perspective cutaway view of one embodiment of the present invention.

Accordingly, as illustrated in the Figures, and as the skilled artisan will readily understand, the uncorroded point(s) 1206 involved in electrical arcs, begin to corrode as electrical arcing proceeds. As shown in FIGS. 26 and 30B electrode points 206 may corrode to shorten to form degraded or corroded points 1206' during repeated arcing events. In turn, as will be understood and illustrated, the spark gap between corroding, or corroded, points 1206' will lengthen, creating a greater length of fluid and distance, and resistance, therebetween. Thus, the current flow streamers may continually seek out a shorter, less resistant, spark gap formed or defined by, or between one or more uncorroded points 1206 that are longer in length that corroded point(s) 1206'. Relatedly, in some embodiments, as best shown in FIG. 24, one or more of the uncorroded points 1206 may have a length that is longer than one or more of the other points 1206, as measured by the point(s) 1206 relative length of extension toward the spark gap. The longer point(s) 1206 thus comprise a spark gap length that is shorter, and less resistant, than the spark gap length of other point(s) 1206 that are shorter, or the spark gap length of points 1206' that are corroded and, therefore, shortened to define a longer spark gap length therebetween. FIG. 14 shows an exemplary set of points 1206 wherein one point 1206 is "longer" than an adjacent "shorter" point 1206 and a still shorter point 1206' that has been shortened by corrosion by electrical arcing. As the skilled artisan will readily understand, current flow streamers may preferably seek out a shorter, less resistant, spark gap, i.e., a spark gap comprising one or more "longer" points 1206.

As shown in FIGS. 25 and 26, the extensions or point(s) 1206 of the electrode pairs, e.g., 1201, 1202 may be configured to define a plurality of spark or arc gaps therebetween, each spark gap in the plurality corresponding with a pair of opposing extensions or points 206 that are radially and longitudinally aligned between the exemplary spaced-apart electrodes 1201, 1202. In this manner, as one spark gap lengthens due to corrosion as described herein, the current streamer formation may move to another pair of longitudinally aligned opposing extensions or points 1206 that are uncorroded and, therefore, in some embodiments, defining a spark gap that is shorter than the spark gap that has lengthened due to corrosion of the relevant opposing extensions or points 1206. In addition, and as shown, the extensions or points 1206 of the electrode pairs, e.g., 1201, 1202, are radially spaced apart from each other around the relevant electrode 201 and/or 1202. Accordingly, and as further described herein, the corresponding spark gaps therebetween are also radially spaced apart. As a result, a first electrical arc, and the corresponding first pressure wave generated by the first electrical arc, across a first spark gap may occur at a first radial location around the electrodes 1201, 1202 and around elongated member or carrier 1102. A subsequent electrical arc, and its generated pressure wave, may occur at a second radial location around exemplary electrodes 1201, 1202 and that is spaced apart from the first radial location.

The electrodes, including exemplary electrodes 1201, 1202, 1203, 1204, may be metal or semiconductor, and can be plated with a secondary alloy. The base metal may comprise copper or beryllium copper. The plating may comprise platinum, gold, tungsten, osmium, silver, titanium, nickel, or other electrochemically low-activity metal. Carbon surfaces such as graphite, graphene, and diamond may also be used. Still further, stainless steel and steel alloys may be used.

The connection between electrode pairs, e.g., 1201, 1202 and 1203, 1204, may be achieved in many embodiments. As discussed above and as shown at least in FIG. 10, in one embodiment, the two intermediary electrodes, e.g., 1202 and 1203, may be placed in a physically touching relationship wherein the electrical connection effectively comprises a short between the touching electrodes 1202, 1203, allowing current to flow therebetween. The electrodes 1201, 1202, 1203, 1204 may comprise a rear surface (shown in FIG. 28B) that may be substantially flattened, wherein the rear surfaces of intermediary ring electrodes 1202, 1203 may be in a physically touching engagement. Alternatively, the rear surfaces of exemplary intermediary electrodes 1202, 1203 may be spaced apart as further discussed here. Still more alternatively, the rear surfaces of the intermediary ring electrodes may comprise complementary shapes, e.g., one convex and the other concave, wherein one rear surface fits within the other rear surface to comprise a fuller physically touching engagement between the intermediary ring electrodes, e.g., 1202, 1203. The rear surface which may be relatively flattened comprises the side opposite the plurality of points 206 which form and define a front surface of each exemplary ring electrode 1201, 1202, 1203 and 1204.

As shown in FIG. 28, rear surfaces of intermediary electrodes 1202, 1203 may be configured in an adjacent but spaced, apart and non-touching engagement, wherein a jumper conductive wire is disposed between the intermediary electrodes 1202, 1203 across interface I, or a welded bead may interconnect the electrodes 1202, 1203 at the interface I. Alternative means to achieve the required electrical connection at the interface I between intermediary electrodes 1202, 1203 may appear to the skilled artisan, each such electrical connection means is within the scope of the present invention.

Alternative electrode embodiments comprise at least some non-ring electrodes attached or mounted or connected with the elongated catheter 1102, wherein pairs of the non-ring electrodes are arranged in spaced-apart configurations to form flow and pressure wave generators as described above in connection with the ring electrode embodiments. Ring and non-ring electrodes may be combined in a given system.

As discussed supra, a fluid containing sleeve 300 may be provided on any of the flow and pressure wave generators of FIGS. 22-33 to assist in providing longer gaps between electrodes.

In certain embodiments, selected individual points or extensions 1206 may be specifically energized with individual wired connection(s) and/or individual points 1206 may be de-energized in order to ensure they do not participate in current flow, for at least a period of time and/or during treatment of a certain region of the subject vessel.

In other embodiments, the points 1206 may be selectively and intentionally degraded (or not degraded) based on material selection and/or relative length of the tip of certain of the points 1206 relative to the other points 1206.

Wiring/Cabling

The disposable catheter assembly may comprise two or more insulated conductors connecting the system of electrodes, electrode pair(s) and/or flow and pressure wave generator(s) to the power supply. A typical excitation pulse is 200 A @ 4 KV for a developed arc, where the conductors dominate the load, requiring a load impedance of 20 ohms. The round trip cable length in the disposable catheter is approximately 10 feet, so the maximum resistance of the cable is an ohm/foot for each trace, which is typical for 40 ga copper wire. Additional cable flexibility can result with using multiple strands of finer bonding wire with the same cumulative cross sectional area as the 40 ga wire.

The Figures illustrate electrical conductors comprising insulation that are operatively connected with the power source 1300 and wherein one of the electrical conductors is in electrical communication with the proximal-most electrode 1201, an electrical structure well-known to the artisan. FIG. 27 provides an exemplary connection embodiment wherein an end portion of insulated conductor is stripped of insulation exposing a length of distal conductor portion 1212 that is operatively connected with electrode 1201. A similar connection mechanism may be employed for the connection between the other electrical conductor and the distal-most electrode, e.g., element 1204.

Figure 29:
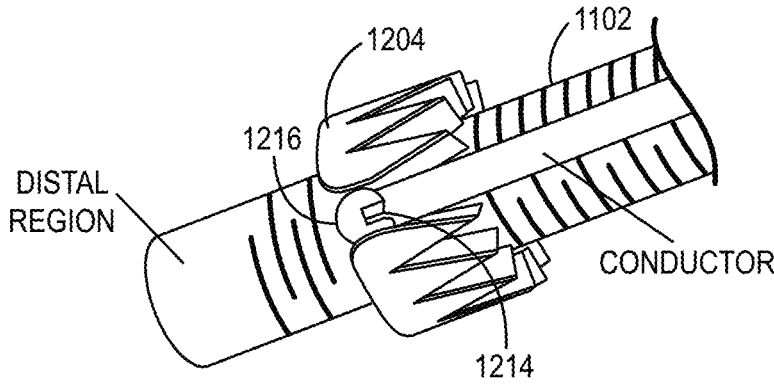
FIG. 29 illustrates a perspective cutaway view of one embodiment of the present invention.
Figure 32:
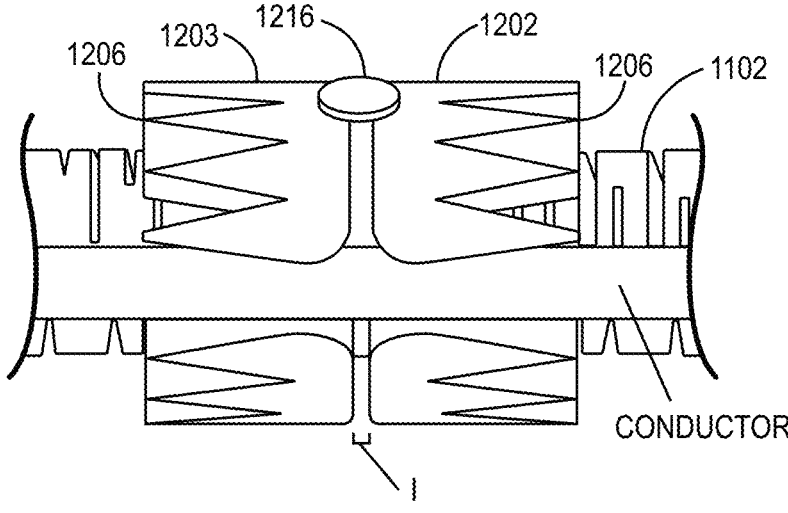
FIG. 32 illustrates a side cutaway view of one embodiment of the present invention.
Figure 33:
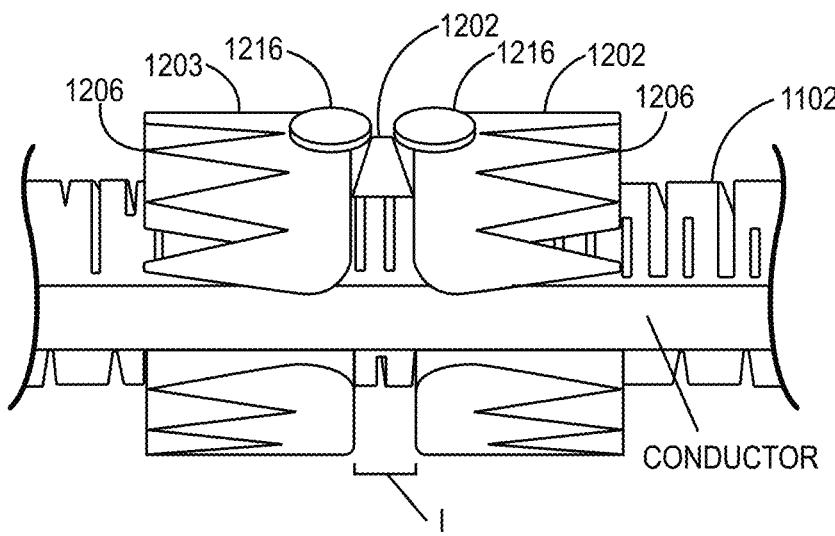
FIG. 33 illustrates a side cutaway view of one embodiment of the present invention.

Alternatively, a conductor may comprise a distal conductor portion 1214 that is stripped of insulation and that is connected with the relevant ring electrode by a weld bead 1216 as shown in FIG. 29. Any of the electrical conductors may be connected to the relevant ring electrode in this manner.

In order to minimize outer diameter and crossing profile of the system, the electrical conductors may be run within a lumen defined in catheter 1102, wherein the distal conductor portion is operatively connected with the relevant electrode through an aperture in the catheter 102 and/or via a weld bead as described above.

Alternatively and as shown in the Figures, the electrodes 1201, 1202, 1203, 1204, may comprise a channel or groove 1208 sized for the electrical conductor(s) to reside within. The channel 1208 may provide the connection point for one or more of the electrodes as is shown in, e.g., FIGS. 27 and 28. Channel 1208 may allow the electrical conductor(s) to slide there along to accommodate changes in the attitude of the catheter 1102 during advancement of the exemplary device 1100 through a patient's vasculature.

Still more alternatively, a longitudinal channel or a spiral or other shaped channel may be defined in the wall of elongated catheter 1102. The conductor(s) may be at least partially disposed in the channel to assist in minimizing crossing profile of the system.

Power Supply/Pulse Generator

In some embodiments, a capacitor bank may be provided and may be charged during an exemplary 1-minute off period, followed by a short or connection of the capacitors to the electrodes for the discharge and arc generation. The charging period may be less than 1-minute in preferred embodiments. In other embodiments, a current may be established in a transformer primary, wherein that current is halted to generate a large voltage across the secondary.

As noted, the charging period may be much less than 1 minute as a pulse may be delivered to the electrodes at least once a second. The pulse rate may be limited with sensed temperature of the conductive fluid F and/or balloon material so that the temperature of surrounding tissue is not increased beyond a predetermined threshold, e.g., 1 degree C. of temperature increase for cardiac tissue. The temperature may be monitored using a temperature sensor mounted along the outside surface of the catheter 102 within the conductive fluid F and/or on an inner surface of the balloon, or other location. The temperature sensor may be in operative communication with an externally located processor having operational communication with the predetermined heat threshold(s) and wherein an alert is provided via a display or other mean. In some embodiments, the voltage pulses may be locked out, with no further pulses allowed. In other embodiments, no further voltage pulses are allowed when the predetermined heat threshold is met or exceeded, but the voltage pulses may proceed when the sensed temperature drops below the predetermined heat threshold.

The capacitor bank may be charged from either direction and FETs or triggered spark gaps are controlled to allow the capacitor banks to discharge between the electrodes in an H-bridge configuration. In some embodiments, the current sign may be configured to flip. Phase shaping may be executed to reduce EMI in some embodiments. In some embodiments, both the current and voltage may be monitored to inform what the voltage setting should be for the next pulse delivery. In some embodiments, the voltage may be terminated on a pulse-by-pulse basis and in other embodiments the voltage is not terminated on a pulse-by-pulse basis. Similarly, the electrical arc across a given set of electrodes comprising a flow and pressure wave generator may be terminated on a pulse-by-pulse basis in some embodiments, while in other embodiments, said electrical arc may not be terminated on a pulse-by-pulse basis.

Part of the treatment results from the pressure and tensile phases of the shock wave propagating through the lesion. The peak pressure scales as the energy deposited in the shock wave, and the inverse cube of the distance from the Townsend discharge to the treatment site (for a short length discharge). As the radial distance between discharge and treatment site is not precisely controlled, high precision in the control of voltage and current is not required. The current may flip sign between pulses, droop or exponentially decay during the pulse, and ring or oscillate during the pulse. The flow portion of treatment is optimized by initially deflating the balloon somewhat (so that it can expand with the gas bubble evolution) and by boiling the most water; the time evolution of the flow is a few tens of microseconds. The pressure portion of treatment is optimized by applying electrical energy to the Townsend discharge while its impedance is high, a condition that lasts for a few tens of nanoseconds.

The current and voltage output may be monitored for proper operation. Measuring opens or shorts may produce a prompt or alert to change a catheter assembly for a new catheter assembly. Monitoring the DC impedance between the electrodes, e.g., 201 and 202, and the patient allows catheter insulation leaks to be sensed and corrected. As further described herein, monitoring the DC resistance between the electrodes may provide a temperature monitor. Still further, if the vessel is successfully being opened by treatment, the DC resistance between the electrodes decreases because of the larger cross section of saline conducting between the electrodes. It is further understood that as gas is produced from the arcs, the resistance will change.

Further, sensing and/or monitoring the conductivity of the conducting fluid F within the balloon alone, or comparing same with the conductivity of fluid, e.g., blood, outside of the balloon provides alternative mechanisms for determining whether the balloon has been compromised, e.g., a rupture or tear.

The patient's heart rhythm may be monitored, and that these pulses are synchronized to an inactive phase. That synchronization precludes some standard methods, such as a spark gap that closes when the capacitor bank reaches a target voltage. Relatedly, the balloon 104 will expand and contract with a characteristic time and frequency. Voltage pulses may be timed to take advantage of the natural expansion/contraction cycle and frequency. For example, voltage pulses may be timed to the natural expansion of the balloon and/or to the natural contraction of the balloon. The force of the flow and pressure waves will impact the target tissue and/or occluding material, e.g., calcification, at slightly different angles depending on the balloon's expansion state, because, inter alia, the flow and pressure wave generators position will change with expansion/contraction of the balloon.

Temperature Sensor

As discussed above, certain embodiments may comprise a small temperature sensor embedded near the electrodes and/or within the conductive fluid F which may increase the treatment pulse rate up to the limit of a safe rise in tissue temperature—generally local tissue temperature should not be increased more than about 1 degree C. Heat diffusion on the order of 5 mm from the electrodes is required for the heat to be convected by blood circulation. The thermal diffusion time for water at in conduits of relevant radius range is (5 mm)2/k=167 seconds. However, a 0.5 J pulse raises a 5 mm radius sphere of water approximately 0.23 degrees C., so a 1-pulse/spark-per-minute rate may be increased to 2-pulses/sparks-per minute in certain embodiments.

The temperature sensor may be optical fiber based, or a micro-thermocouple. Since saline increases conductivity with temperature, the current produced by a DC bias applied to the electrodes will increase monotonically with temperature, allowing the temperature of the warmest region to be measured directly. As described above, a predetermined heat or temperature increase threshold may be provided with subsequent alerts and/or corrective or remedial actions implemented by programmed instructions implemented by a processor.

Balloon and Inflation Liquid

Angioplasty balloons are developed and nuanced. Embodiments of the present invention comprise standard angioplasty balloons and related, and known, basic inflation/deflation mechanisms. A typical balloon length may be 12 mm and may be used with 0.14-0.35 in guide wires. The inflated balloon size may comprise about 90% of the nominal vessel size.

Varying the salinity of the water used to inflate the balloon has an impact on the ionic current density prior to boiling; a high saline concentration lowers the resistance, thereby increasing the power density deposited for a constant drive voltage. If the ionic current paths are not constrained to the vicinity of the electrodes, but are allowed to penetrate the bulk of the balloon interior, so much current can be consumed heating a large amount of water that boiling does not take place after even a few Joules have been expended.

Figure 23:
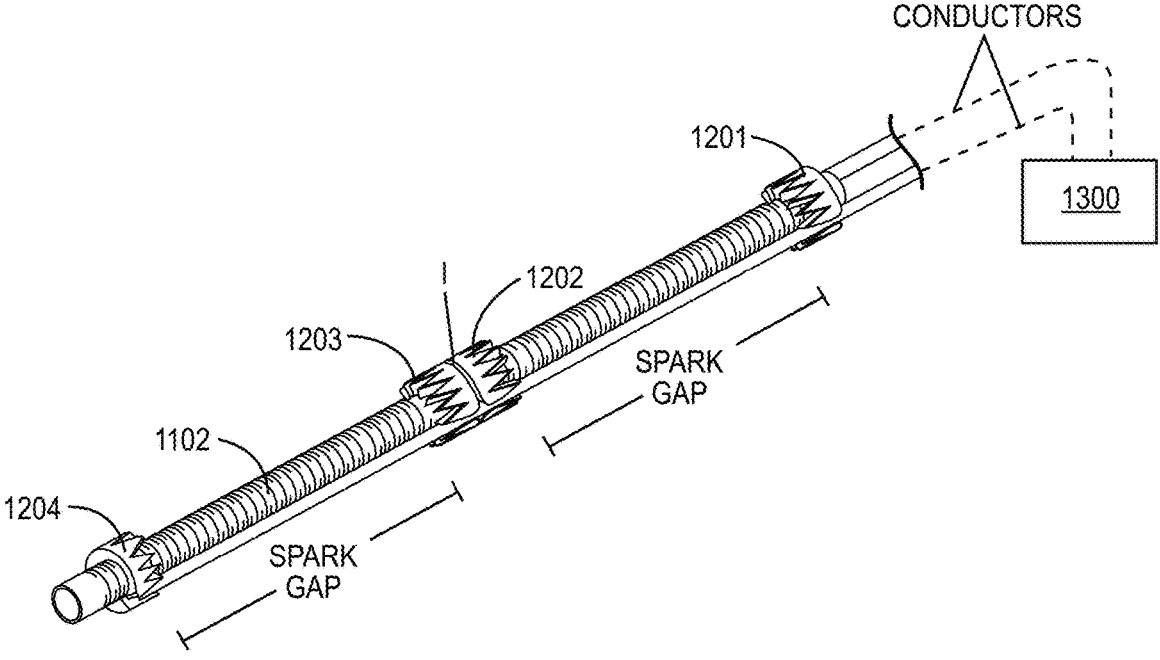
FIG. 23 illustrates a perspective cutaway view of one embodiment of the present invention.

With reference to at least FIG. 23, the voltage pulse generated by the power source or voltage pulse generator 1300 generates streamers in the steam formed from the fluid F interposed between, e.g., the proximal electrode 1201 and the next more distal electrode 1202 that comprise a flow and pressure wave generator 1200. As described above, the distal-most ring electrode is also operatively connected with the power source 1300. Sufficient voltage applied to the proximal electrode 1201 results in streamers and ultimately current flowing between the two electrodes of the electrode pair 1201, 1202, generating an arc and a resultant flow and pressure wave as a bubble forms and expands in the fluid F. That bubble will generally collapse, producing another flow and pressure wave as the bubble shrinks to nearly a point, bouncing to produce a second growing bubble.

We note here that the flow wave generated may travel at subsonic speeds while the pressure wave may travel at sonic and/or supersonic speeds.

The distance between electrodes of an electrode pair, e.g., 1201, 1202 may be relatively long, e.g., 5 mm or longer. In this case, the generated bubble and resulting pressure wave may comprise cylindrical shapes, with the end portions of each more spherical in shape.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

Having described the invention, we claim:

1. An intravascular lithotripsy system comprising:
an elongate member defining a lumen;
a first set of two spaced-apart electrodes with a gap therebetween attached to the elongate member;
a voltage pulse generator in electrical communication with the first set of two spaced-apart electrodes;
an inflatable sleeve surrounding the at least one of the two spaced-apart electrodes and comprising a proximal end, a distal end, at least one inflated volume and at least one inflated diameter, the proximal end and the distal end of the sleeve both operatively attached to the elongate member, the inflatable sleeve being configured to be inflated with a fluid;
an inflatable balloon that is configured to surround the inflatable sleeve, wherein the inflatable balloon is configured to be inflated with the fluid and comprising at least one inflated volume, wherein an inflated volume of the inflatable balloon comprises a volume that is at least two times greater than the at least one inflated volume of the inflatable sleeve that is surrounded by the balloon, wherein the inflatable sleeve is surrounded by the fluid within the inflatable balloon; and a fluid reservoir comprising the fluid and in fluid communication with an interior of the inflatable sleeve, wherein the interior of the inflatable sleeve is in fluid communication with the fluid within the inflated balloon and is configured to be inflated by passive or diffusive inflation with fluid from within the inflatable balloon, or by active inflation with the fluid from the fluid reservoir.

2. The system of claim 1, wherein the inflatable balloon comprises at least one inflated diameter and wherein the inflatable sleeve comprises at least one inflated diameter, wherein an inflated diameter of the inflatable balloon is at least two times greater than an inflated diameter of the inflated diameter of the inflatable sleeve.

3. The system of claim 1, further comprising:
a fluid reservoir comprising the fluid and in fluid communication with an interior of the inflatable balloon, wherein the inflatable balloon is configured to be inflated
and/or deflated by active inflation from, or deflation of the fluid into, the fluid reservoir.

4. The system of claim 1, wherein the inflatable sleeve comprises at least one flow channel disposed between an outer surface of the elongate member and the proximal end and/or distal end of the sleeve for fluid communication of the fluid between the interior of the inflatable balloon and the interior of the inflatable sleeve.

5. The system of claim 1, wherein the inflatable sleeve comprises one or more apertures through the sleeve.

6. The system of claim 1, wherein the inflatable sleeve constrains the volume of the fluid within the inflatable sleeve to a channel that fills the gap between the two spaced-apart electrodes, and wherein the inflatable sleeve does not touch the inflatable balloon when the inflatable sleeve and inflatable balloon are both inflated with the fluid.

7. The system of claim 1, wherein the gap between the first set of the two spaced-apart electrodes comprises a first gap between a first electrode and a second electrode; and
a third electrode spaced away from the first electrode and in electrical communication with the voltage pulse generator, and comprising a second gap between the first electrode and the third electrode, and wherein the inflatable sleeve constrains the volume of fluid to a channel that fills the first and second gaps.

8. The system of claim 7, wherein the first gap between the first electrode and the second electrodes is within a range of 0.1 mm to 15 mm.

9. The system of claim 1, wherein the gap between the electrodes is within a range of 0.1 mm to 15 mm.

10. The system of claim 1, wherein the sleeve comprises a polymer.

11. The system of claim 1, wherein the sleeve comprises silicone.

12. The system of claim 1, further comprising a second set of two spaced-apart electrodes in electrical communication with the voltage pulse generator.

13. The system of claim 12, wherein the two spaced-apart electrodes are disposed within the inflatable sleeve.

14. The system of claim 12, further comprising another inflatable sleeve, each of the inflatable sleeve and the another inflatable sleeves defining a channel of fluid located within the inflatable balloon and operatively attached to the elongate member, and wherein the first set of two spaced-apart electrodes is disposed within the inflatable sleeve and wherein the second set of the two spaced-apart electrodes is disposed within the another inflatable sleeve, wherein the first and second sets of two spaced-apart electrodes are spaced longitudinally apart from each other.

15. The system of claim 1, wherein the inflatable sleeve is disposed against an insulated outer surface of each electrode of the first set of two spaced-apart electrodes.

16. The system of claim 1, wherein the sleeve is configured to be actively inflated with fluid from a fluid reservoir.

17. An intravascular lithotripsy system comprising:
an elongate member defining a lumen;
two spaced-apart electrodes configured to be in electrical communication with a voltage pulse generator that is configured to apply voltage to one of the two spaced-apart electrodes and generate an arc therebetween, the arc launching a shock wave with a high peak wave pressure and a low tensile wave pressure and maximize electrical energy expended when the arc is initiated;
a first fluid fillable member surrounding the two spaced-apart electrodes, the first fluid fillable member comprising a proximal end and a distal end, wherein the proximal end and the distal end is sealed to an outer surface of the elongate member, configured such that a fluid within the first fluid fillable member in an inflated configuration is constrained to a channel surrounding the two spaced-apart electrodes; and
a fluid reservoir in fluid communication with an interior of the first fluid fillable member.

18. The system of claim 17, wherein the first fluid fillable member constrains a volume of fluid to the channel that fills a gap between the two spaced-apart electrodes, the channel being a narrow channel.

19. The system of claim 18, wherein the gap between electrodes is within a range of 0.1 mm to 15 mm.

20. The system of claim 17, further comprising a third spaced-apart electrodes with a first gap between a first electrode of the two spaced-apart electrodes and a second electrode of the two spaced-apart electrodes and a second gap between the first electrode and a third electrode, and wherein the first fluid fillable member constrains a volume of fluid to the channel that fills the first and second gaps.

21. The system of claim 20, wherein the first gap between the first electrode and the second electrodes is within a range of 0.1 mm to 15 mm.

22. The system of claim 17, wherein the first fluid fillable member comprises a polymer.

23. The system of claim 17, wherein the first fluid fillable member comprises silicone.

24. The system of claim 17, further comprising a third electrode and a fourth electrode spaced-apart from the third electrode, wherein the third electrode and the fourth electrode are longitudinally spaced apart from the two spaced-apart electrodes.

25. The system of claim 24, wherein the two spaced-apart electrodes, the third electrode and the fourth electrode are disposed within a first fluid fillable member.

26. The system of claim 24, further comprising a second fluid fillable member, and wherein the two spaced-apart electrodes are disposed within the first fluid fillable member and wherein the third electrode and the fourth electrode are disposed within the second fluid fillable member, wherein each of the first fluid fillable members are in fluid communication with the fluid reservoir.

27. An intravascular lithotripsy system comprising:
an elongate member defining a lumen;
two spaced-apart electrodes attached to the elongate member and configured to electrically communicate with a voltage pulse generator;
wherein the voltage pulse generator is configured to apply voltage to one of the two spaced-apart electrodes and generate an arc therebetween that launches a shock-wave with a high peak wave pressure and a low tensile wave pressure and maximize electrical energy expended when the arc is initiated;
an inflatable balloon surrounding the two spaced-apart electrodes, the inflatable balloon sealed to the elongate member to form an interior; and
a fluid reservoir in fluid communication with the interior of the inflatable balloon,
wherein the inflatable balloon is deflated to a deflated configuration configured to constrain the fluid within the interior of the balloon to a narrow channel of fluid around the two spaced-apart electrodes before application of voltage to one of the two spaced-apart electrodes and maintained in the deflated configuration as the arc is generated,
wherein the balloon's position is constrained such that the deflated configuration of the balloon is distanced from the arc generated between the spaced-apart electrodes.

28. The system of claim 27, wherein the inflatable balloon in the deflated configuration constrains a volume of fluid to the narrow channel that fills a gap between the two spaced-apart electrodes.

29. The system of claim 28, wherein the gap between the electrodes is within a range of 0.1 mm to 15 mm.

30. The system of claim 27, further comprising a third electrode with a first gap between a first electrode and a second electrode and a second gap between the first electrode and a third electrode, and wherein the inflatable balloon in the deflated configuration constrains a volume of fluid to the narrow channel that fills the first and second gaps.

31. The system of claim 30, wherein the first gap between the first electrode and the second electrodes is within a range of 0.1 mm to 15 mm.

32. An intravascular lithotripsy device, comprising:
an elongate member defining a lumen;
a pressure wave generator attached to the elongate member comprising a wire and a ring electrode, wherein the pressure wave generator is configured for electrical communication with a voltage pulse generator that is configured to apply voltage to one of the wire and the ring and generate an arc therebetween, the arc launching a shockwave with a high peak wave pressure and a low tensile wave pressure and maximize electrical energy expended when the arc is initiated; and
a fluid-fillable enclosure surrounding the pressure wave generator, wherein the fluid-fillable enclosure is configured for fluid communication with a fluid reservoir,
wherein when the fluid-fillable enclosure is in a fluid-filled configuration, the fluid-fillable enclosure is configured such that fluid within the fluid-fillable enclosure at least partially fills a gap between the wire and the ring electrode, and
when the fluid-fillable enclosure is in the fluid-filled configuration, the fluid-fillable enclosure is at least partially disposed against an outer surface of the ring electrode.

* * * * *